(12) United States Patent
Herzog et al.

(10) Patent No.: US 8,236,933 B2
(45) Date of Patent: Aug. 7, 2012

(54) MODIFIED ANIMAL LACKING FUNCTIONAL PYY GENE, MONOCLONAL ANTIBODIES THAT BIND PYY ISOFORMS AND USES THEREFOR

(75) Inventors: Herbert Herzog, Bondi (AU); Charles Mackay, Vaucluse (AU)

(73) Assignee: Garvan Institute of Medical Research, Darlinghurst, NSW (AU)

( * ) Notice: Subject to any disclaimer, the term of this patent is extended or adjusted under 35 U.S.C. 154(b) by 894 days.

(21) Appl. No.: 11/911,300

(22) PCT Filed: Apr. 13, 2006

(86) PCT No.: PCT/AU2006/000503
§ 371 (c)(1),
(2), (4) Date: Jul. 21, 2008

(87) PCT Pub. No.: WO2006/108234
PCT Pub. Date: Oct. 19, 2006

(65) Prior Publication Data
US 2010/0143934 A1    Jun. 10, 2010

(30) Foreign Application Priority Data

Apr. 13, 2005  (AU) ................................ 2005901846
Mar. 14, 2006  (AU) ................................ 2006901306

(51) Int. Cl.
C07K 16/26 (2006.01)
G01N 33/53 (2006.01)
G01N 33/74 (2006.01)
C12N 5/12 (2006.01)

(52) U.S. Cl. .................. 530/388.22; 435/7.1; 435/326; 435/331; 435/346

(58) Field of Classification Search .................. None
See application file for complete search history.

(56) References Cited

U.S. PATENT DOCUMENTS 5,955,354 A * 9/1999 Williams et al. ............ 435/320.1
2004/0228846 A1* 11/2004 Pang et al. ................... 424/93.7

FOREIGN PATENT DOCUMENTS

WO    WO 00/047219     * 8/2000
WO    2005/110454      * 11/2005

OTHER PUBLICATIONS

Eberlein 1989 (Peptides 10:797-803).*
Grandt 1994 (Regulatory Peptides 51:151-159).*
Batterham, R.L., "Inhibition of Food Intake in Obese Subjects by Peptide $YY_{3-36}$," The New England Journal of Medicine, Sep. 4, 2003, p. 941-948, vol. 349, No. 10.
Boey, D., et al., "Peptide YY ablation in mice leads to the development of hyperinsulinaemia and obesity," Diagetologia, Apr. 21, 2006, p. 1360-1370, vol. 49.
"Human PYY (3-36) RIA Kit," 1997-2003, [online] [Retrieved on Sep. 28, 2005] Retrieved from the internet URL:http://www.lincoresearch.com/protocols/frames/prot_pyy-67hk.html.
"Human PYY EIA Kit," CosmoBio Co., LTD., Date unknown, [online] [Retrieved on Apr. 23, 2008] Retrieved from the internet URL:http://search.cosmobio.co.jp/cosmo_search_p/search_gate2/docs/YII_/YK080EX.20071031.pdf.
Hung, C-C., "Studies of the Peptide YY and Neuropeptide Y2 Receptor Genes in Relation to Human Obesity and Obesity-Related Traits," Diabetes, Sep. 2004, p. 2461-2466, vol. 53.
"Peptide YY 3-36," Date unknown, [online] [Retrieved on Feb. 15, 2008] Retrieved from the internet URL:http://www.phoenixpeptide.com/catalog/pnxfoget.php?id=pnxnews_000000213&title=Compound&sum=Function.
Schonhoff, S., "Energy Homeostasis and Gastrointestinal Endocrine Differentiation Do Not Require the Anorectic Hormone Peptide YY," Molecular and Cellular Biology, May 2005, p. 4189-4199.
Young, A., "Obesity: A Peptide YY-Deficient, But Not Peptide YY-Resistant, State," Endocrinology, Jan. 2006, p. 1-2, vol. 147, No. 1.

* cited by examiner

*Primary Examiner* — Daniel E Kolker
(74) *Attorney, Agent, or Firm* — Fenwick & West LLP

(57) ABSTRACT

The present invention provides transgenic animals having a reduced level of expression of peptide YY (PYY) and drug screening platforms using the transgenic animals for identifying agonists and antagonists of PYY. The present invention further provides monoclonal antibodies that bind specifically to full-length PYY[1-36] or the processed form thereof i.e., PYY[3-36] and to diagnostic and drug screening platforms using the monoclonal antibodies. The invention has particular utility for the diagnosis of a predisposition or risk of a subject becoming obese, developing one or more pathologies associated with obesity, or developing a disease/disorder of bone tissue.

19 Claims, 39 Drawing Sheets

Fat Diet

Wild Type | PYY⁻

Male

Female

MODIFIED ANIMAL LACKING FUNCTIONAL PYY GENE, MONOCLONAL ANTIBODIES THAT BIND PYY ISOFORMS AND USES THEREFOR

This application is the National Stage of International Application No. PCT/AU2006/000503, published in English under PCT Article 21(2), filed Apr. 13, 2006, which claims priority to Australian Patent Application No. 2005901846, filed Apr. 13, 2005, and Australian Patent Application No. 2006901306, filed Mar. 14, 2006, each of which are incorporated by reference in their entirety.

FIELD OF THE INVENTION

The present invention relates generally to the productions of transgenic animals having a reduced level of expression of peptide YY (PYY) or a variant thereof and uses therefor to identify a compound that mimic the effect(s) of PYY or variant thereof in a human or a non-human animal. The present invention further relates to a method for producing a monoclonal antibody that binds to full-length PYY[1-36] or the processed form thereof i.e., PYY[3-36] and to such monoclonal antibodies per se and their use to diagnose a predisposition or risk of a subject becoming obese or overweight or developing a disorder of bone tissue.

BACKGROUND OF THE INVENTION

General

This specification contains nucleotide and amino acid sequence information prepared using PatentIn Version 3.3. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (e.g. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts that are incorporated by reference:

Sambrook, Fritsch & Maniatis, Molecular Cloning: A Laboratory Manual, Cold Spring Harbor Laboratories, New York, Second Edition (1989), whole of Vols I, II, and III;
DNA Cloning: A Practical Approach, Vols. I and II (D. N. Glover, ed., 1985), IRL Press, Oxford, whole of text;
Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
Nucleic Acid Hybridization: A Practical Approach (B. D. Hames & S. J. Higgins, eds., 1985) IRL Press, Oxford, whole of text;
Animal Cell Culture: Practical Approach, Third Edition (John R. W. Masters, ed., 2000), ISBN 0199637970, whole of text;
Immobilized Cells and Enzymes: A Practical Approach (1986) IRL Press, Oxford, whole of text;
Perbal, B., A Practical Guide to Molecular Cloning (1984);
Methods In Enzymology (S. Colowick and N. Kaplan, eds., Academic Press, Inc.), whole of series;
J. F. Ramalho Ortigão, "The Chemistry of Peptide Synthesis" In: Knowledge database of Access to Virtual Laboratory website (Interactiva, Germany);
Handbook of Experimental Immunology, Vols. I-IV (D. M. Weir and C. C. Blackwell, eds., 1986, Blackwell Scientific Publications).

DESCRIPTION OF THE RELATED ART

1. Obesity

The incidence of obesity has increased dramatically throughout the world, most notably over the last 3 decades. By the year 2000, a total of 38.8 million American adults or 30% of the population of that country were classified as obese (i.e., having a body mass index score of at least 30 kg/m$^2$) (Mokdad et al., *JAMA* 286:1195-1200, 2001). Obesity is associated with or thought to cause a number of diseases or disorders, and estimates attribute approximately 280,000 deaths each year in the United States to obesity related disorders (The Merck Manual of Diagnosis & Therapy, Beers & Brakow, 17th edition, Published by Merck Research Labs, Section 1, Chapter 5, Nutritional Disorders, Obesity (1999).

Obesity is a risk factor for developing many obesity-related complications, from non-fatal debilitating conditions, such as, for example, osteoarthritis and respiratory disorders, to life-threatening chronic disorders, such as, for example, hypertension, type 2 diabetes, stroke, cardiovascular disease, some forms of cancer and stroke. As the number of subjects that are obese is increasing (in the US alone the incidence of obesity increased one third in the last decade), the need to develop new and effective strategies in controlling obesity and obesity-related complications is becoming increasingly important. Upper body obesity is the strongest risk factor known for diabetes mellitus type 2, and is a strong risk factor for cardiovascular disease. Obesity is also a recognized risk factor for hypertension, atherosclerosis, congestive heart failure, stroke, gallbladder disease, osteoarthritis, sleep apnoea, reproductive disorders such as polycystic ovarian syndrome, cancers of the breast, prostate, and colon, and increased incidence of complications of general anaesthesia (see, e.g., Kopelman, *Nature* 404, 635-43, 2000). It reduces life span and carries a serious risk of co-morbidities as described above, as well as disorders such as infections, varicose veins, acanthosis nigricans, eczema, exercise intolerance, insulin resistance, hypertension hypercholesterolemia, cholelithiasis, orthopaedic injury, and thromboembolic disease (Rissanen et al., *Brit. Med. J* 301, 835-837, 1990). Obesity is also a risk factor for the group of conditions called insulin resistance syndrome, or "Syndrome X".

However, despite the high prevalence of obesity and many advances in our understanding of how it develops, current therapeutic strategies have persistently failed to achieve long-term success (Crowley et al., *Nat. Rev. Drug Disc.* 1: 276-286, 2002). Moreover, of the subjects that do lose weight, approximately 90 to 95 percent of subsequently regain their lost weight (Rosenbaum et al., *N. Engl. J. Med.* 337:396-407 1997).

Currently there are only two therapeutic drugs approved by the FDA for the long term treatment of obesity. One of these compounds, orlistat, is a pancreatic lipase inhibitor that acts by blocking fat absorption into the body. However, the use of this drug is also accompanied by the unpleasant side effects of the passage of undigested fat from the body.

Another drug commonly used for the treatment of obesity is sibutramine, an appetite suppressant. Sibutramine is a β-phenethylamine that selectively inhibits the reuptake of noradrenaline and serotonin in the brain. Unfortunately, the use of sibutramine is also associated with elevated blood pressure and increased heart rate. As a result of these side effects dosage of sibutramine is limited to a level that is below the most efficacious dose.

Compounds for the short term treatment of obesity include, appetite suppressants, such as amphetamine derivatives. However, these compounds are highly addictive. Furthermore, subjects respond differently to these weight-loss medications, with some losing more weight than others and some not losing any weight whatsoever.

Accordingly, it is clear that there is a need in the art for new diagnostics for identifying obesity or a propensity for obesity in human populations. There is also a need for effective therapeutics for obesity, preferably therapeutic compounds with reduced side effects and/or that are useful for treating a diverse population of subjects.

As a response to this demand for new diagnostic methods and therapeutic agents, the pharmaceutical industry has turned its attention to identifying reagents and methods for assessing obesity, and to identifying the molecular mechanisms involved in the production or onset of obesity. For example, the complete congenital absence of the adipocyte-derived hormone leptin leads to hyperphagia and obesity in both humans and rodents. Both the obesity and the hyperphagia may be reversed by the administration of recombinant leptin (Farooqi et al., *N. Engl. J. Med.*, 341: 879-884, 1999). However, severe leptin deficiency is not a common cause of obesity in humans and leptin supplementation in the majority of subjects tested has little or no effect on fat mass (Heymsfield et al., *JAMA* 282: 1568-1575, 1999). As a consequence, recombinant leptin does not appear to be a useful therapeutic for the treatment of obesity in the population at large.

Non-human animal models have aided in our understanding of the molecular mechanisms underlying obesity in humans. However, while our understanding of these mechanisms has rapidly increased, there is still insufficient knowledge to produce a therapeutic for the treatment of obesity, particularly, for the long-term treatment in this disorder. Accordingly, animal models of obesity, particularly, those that develop glucose intolerance are highly desirable. Such models have utility in determining appropriate targets for the therapy of a wide range of disorders associated with aberrant glucose metabolism and/or obesity and for determining the efficacy or specificity of therapeutics.

2. The Role of PYY in Obesity

PYY is a neuropeptide of 36 amino acids in length belonging to the NPY family of neuropeptides. Full-length PYY i.e., PYY[1-36], binds to all Y receptors i.e., Y-Y1 through Y-Y7, to activate the many pathways in which those receptors are involved.

The full-length neuropeptide is enzymatically processed to remove the first two amino acids, thereby producing PYY[3-36]. In contrast to full-length PYY, PYY[3-36] is specific for presynaptic inhibitory Y-Y2 receptors and possibly Y-Y5 receptors. Functionally, peripherally-administered PYY[3-36] acts as a satiety signal to inhibit food intake, at least in humans and rodents. PYY[3-36] is released into the circulation after eating and physiologically inhibits food intake. Obese and lean subjects are equally sensitive to this effect, however it has been shown that fasting levels of PYY are reduced in obese subjects. Intranasal administration of PYY [3-36] is known for the treatment of obesity.

Le Roux et al., *Endocrine Abstracts* 7, P42, 2004 investigated postprandial PYY responses and satiety responses using a visual analogue scale (VAS) to test meals of increasing calorie content in lean and obese subjects. They also infused volunteers with multiple doses of PYY to test the effect on satiety. The authors showed that lean and obese subjects had a rise in PYY in response to increasing calories. Obese subjects however, had inappropriately low levels of satiety and an attenuated PYY response at each calorie level, suggesting that a doubling in the meal calorie content was required to achieve equivalent PYY levels to those observed in lean subjects. Infusions of increasing doses of PYY produced a graded inhibition of appetite and food intake. The authors concluded that obese individuals have a functional PYY deficiency and reduced satiety and that lower postprandial PYY levels in obesity might result in an increase in food intake of approximately 10%.

Roth et al., *J Clin Endocrinol Metab.* 90, 6386-6391, 2005 also suggest that decreased PYY levels could predispose juvenile subjects to becoming obese and that that low pretreatment PYY levels that increase during weight loss may be a predictor of maintained weight loss in juvenile subjects.

3. Bone Remodeling and Disorders/Diseases of Bone Tissue

Living bone tissue is continuously being replenished by the processes of resorption and deposition of bone matrix and minerals. This process, termed bone remodeling, is largely accomplished by two cell populations, osteoclasts and osteoblasts. Osteoclasts are recruited from bone marrow or circulation to the bone surface where they break down pre-existing bone matrix and minerals (i.e. bone resorption). The bone matrix and minerals are subsequently replaced by osteoblasts that are recruited from bone marrow to the site of bone resorption.

Changes in the numbers of osteoclasts or osteoblasts or the activity of either of these cell types has been associated with a variety of diseases, such as, for example, osteomalacia, hyperostosis and osteoporosis, including involutional osteoporosis, post-menopausal osteoporosis, senile osteoporosis and steroid (glucocorticoid osteoporosis). Each of these diseases is characterized by low bone mass and structural deterioration of the bone tissue resulting in bone fragility and an increased risk of fracture, especially of the hip, spine and wrist.

The most common of the bone diseases, osteoporosis, is a systemic skeletal disease, characterized by low bone mass and deterioration of bone tissue, with a consequent increase in bone fragility and susceptibility to fracture. It is the most common type of metabolic bone disease in the U.S., and the condition has been estimated to affect approximately 10 million people in the United States alone. In addition to those suffering from diagnosed osteoporosis, it is estimated that up to 3 to 4 times this number may have low bone mass placing them at an increased risk of bone fracture. Osteoporosis causes more than 1.5 million fractures each year, including 700,000 vertebral fractures, 300,000 hip and 250,000 wrist fractures annually, the treatment of which is estimated to cost approximately US$ 17 billion per annum.

In addition to the well-known bone diseases a variety of other conditions are characterized by a need to enhance bone formation. For example, it would be desirable to enhance bone formation and repair in order to treat a common bone fracture. Augmentation of bone formation and/or repair would also be of particular use in the treatment of bone segmental defects, periodontal defects, metastatic bone disease, and osteolytic bone disease (such as, for example, myeloma).

Whilst there has been significant progress in identification and characterization of putative therapeutics for the treatment of bone diseases, and in particular osteoporosis, there still exists a need for new therapeutics for the treatment of these diseases. Moreover, there exists a need for a model of the human condition that allows researchers to assess the efficacy of new compounds not only on bone remodeling, but also other processes of the body.

Currently, therapeutics are merely screened by determining the effect of the putative therapeutic compound on bone formation in an animal, assays that are performed over extended periods of time (i.e. 1 to 8 months depending on the choice of model organism). Alternatively compounds are tested in cell culture, to determine the effect of compounds of bone cell proliferation, an assay that does not consider the effect of the compound on other processes in the body. Accordingly, a more rapid assay for the identification of compounds capable of modulating bone formation would greatly expedite the identification of new lead compounds. In particular, an in vivo assay that facilitates not only determining the effects of a compound on bone formation but also other systems and organs in a subject is particularly desirable.

4. The Role of Neuropeptide Signaling in Bone Remodeling

There is no established correlation between levels of PYY [1-36] and/or PYY[3-36] and bone remodeling.

In contrast, US Patent Publication No. 20040053864 (Mar. 18, 2004) disclosed a correlation between neuropeptide Y levels and bone density in rodents. In particular, the disclosure demonstrated that direct administration of neuropeptide Y into the brains of wild type rats causes a decrease in bone volume and bone mass as compared with control, PBS-treated mice. The specification suggested that modulation of neuropeptide Y signaling can be used to modulate bone mass, and therefore bone disease characterized by increased or decreased bone mass relative to that of corresponding non-diseased bone.

International Patent Application No. PCT/AU2003/001227 (WO2005/026342) disclosed several Y receptor knockout mice exhibiting consistent large increases in bone formation and cancellous bone volume. In particular, the specific ablation of Y-Y1 or Y2 receptors, or the ablation of combinations of Y1 and Y2 receptors, Y1 and Y4 receptors, Y2 and Y4 receptors, or Y1 and Y2 receptor and Y4 receptors produced increases in cancellous bone volume, trabecular thickness and trabecular number. The specification taught that modulation of the level of expression or the activity of a Y receptor or a combination of Y receptors modulates the activity of osteoblasts resulting in the production of more bone matrix and an increased mineral apposition rate (i.e. an increase in bone remodeling). Additionally, WO2005/026342 showed that ablation of Y-Y4 receptor expression dramatically altered the sensitivity of an animal subject to a modulator of bone remodeling. The disclosure also showed that the ablation of Y-Y2 receptor expression produces a greater effect on bone remodeling and bone growth in male subjects compared to female subjects (i.e. a greater enhancement of bone remodeling or bone growth in male subjects compared to female subjects).

The WO2005/026342 disclosure provided several assay methods for determining modulators of neuropeptide Y receptor associated bone remodeling or bone formation, which methods generally involved determining the level of neuropeptide Y receptor expression and/or activity in the presence of a candidate compounds and then determining bone remodeling or bone growth. In some embodiments, such assays employed a read-out which involved binding a PYY ligand to determine Y receptor activity, however there was no mention in the disclosure of assays for determining the level of PYY, or the role of PYY in bone remodeling or bone formation. In fact, saturating levels of PYY would be employed in such assays to ensure that binding to substantially all active Y receptors in the assay sample.

5. Antibodies Against PYY

Polyclonal antibodies have been identified that bind both the full-length PYY i.e., PYY[1-36] and PYY[3-36] with approximately equal affinity (Phoenix Pharmaceuticals, Inc; Cosmo Bio Co. Ltd). These antibodies are sold in kit form, which are disclosed for use in RIA or chemiluminescence-based immunoassays. To achieve any specificity for PYY[1-36] or PYY[3-36] it is necessary to incorporate a labeled PYY[1-36] or PYY[3-36] tracer at non-saturating levels to compete for binding of the unlabeled PYY[1-36] or PYY[3-36] present in the sample. This competition is required because the antibodies are non-specific in their binding. This means that assay samples will contain different amounts of both PYY[1-36] and PYY[3-36] and, as a consequence, it is difficult to produce a linear standard curve over a wide concentration range, especially when there are large amounts of unlabelled PYY[1-36] in the sample or the amount of unlabelled PYY[3-36] is very low. This makes quantitation difficult.

SUMMARY OF THE INVENTION

In work leading up to the present invention the present inventors sought to produce a mouse model that developed obesity, preferably, obesity associated with glucose intolerance. This model was developed for use in studying glucose clearance, fat metabolism, insulin secretion and adiposity in this disorder. The inventors produced a mouse with a disrupted precursor peptide YY (prePYY) locus that was incapable of expressing functional PYY protein. As exemplified herein, mice lacking functional PYY expression develop a progressive form of obesity, presenting in young mice (e.g., of 14 weeks of age or less) as increased fasting and glucose induced levels of serum insulin, elevated basal levels of free fatty acids and triglycerides, elevated levels of corticosterone, reduced levels of thyroid hormone (T4) and increased liver weight with little or no increase in adiposity or glucose intolerance. These phenotypes are indicative of a pre-obese disorder, i.e., several changes are indicative of obesity, however, mice do not have increased adiposity or glucose intolerance. However, as the mice age (e.g., to 20 weeks of age) they develop increased body weight, increased body fat, increased fat mass and glucose intolerance. The age of onset of increased adiposity (e.g., increased body fat and increased fat mass) and/or glucose intolerance was reduced by feeding prePYY knockout mice on a diet high in fat.

The data provided herein also demonstrate that PYY knockout mice exhibit consistent large increases in bone mineral density and bone mineral content. The ablation of PYY expression produces a greater effect on bone remodeling and/or bone growth in male subjects compared to female subjects.

Accordingly, the present invention provides a genetically modified non-human animal in which the expression of precursor peptide YY (PYY) or a derivative thereof is reduced or prevented by targeted disruption of an endogenous PYY-encoding gene. In a preferred embodiment, the present invention provides a genetically modified non-human animal in which the expression of precursor peptide YY (i.e., prePYY) or a derivative thereof e.g., PYY[1-36] or PYY[3-36] is reduced or prevented. Preferably, the genetically modified non-human animal of the present invention comprises one or more additional modifications to its genome e.g., an additional modification selected from the group consisting of knockout of an NPY-encoding gene, knockout of one or more Y receptor-encoding genes, knockout of a leptin-encoding gene and knockout of a pancreatic polypeptide (PP)-encoding gene and combinations thereof. Alternatively, or in addition, the reduced or prevented PYY expression of the genetically modified non-human animal is in a genetic background that confers an obesity or diabetes syndrome on an animal having functional PYY expression.

For the purposes of nomenclature only, the sequence of mouse prePYY is set forth in SEQ ID NO: 2.

By "genetically modified" is meant that a non-human animal comprises a change in its cellular nucleic acid that prevents or reduces the expression of precursor peptide YY (prePYY) or a derivative thereof. For example, the genetically modified animal comprises a mutation in the gene encoding prePYY or a regulatory sequence encoding said gene thereby reducing expression of the gene. Alternatively, the mutation prevents or reduces the translation of a form of prePYY, e.g., a prePYY derivative. Suitable methods for genetically modifying a non-human animal to reduce or inhibit expression of a prePYY or a derivative thereof will be apparent to the skilled artisan and/or described herein.

As used herein, the term "non-human animal" shall be taken to refer to any animal (other than a human) that expresses a prePYY or a derivative of a prePYY or a peptide with a high degree of sequence identity to a derivative of prePYY (e.g., at least about 80% or 90% or 95% amino acid identity) in its native state (i.e., when it is not genetically modified. Preferably, the non-human animal is a model organism, such as, for example, a fish (e.g., *Danio rerio*), a bird (e.g., a chicken), a rodent (e.g., a mouse or a rat), a sheep, a pig, an ovine (i.e., a cow), a goat or a non-human primate (e.g., a chimpanzee). In a preferred embodiment, the non-human animal is a non-human mammal, more preferably, a rodent and even more preferably, a mouse.

Preferably, a genetically modified non-human animal in which the expression of precursor peptide YY (prePYY) or a derivative thereof is reduced or prevented comprises or exhibits any one or more of the following phenotypes:
(i) an increased fasting serum insulin level relative to a fasting serum level in a wild-type (wt) animal;
(ii) an increased glucose induced serum insulin level relative to a fasting serum level in a wt animal;
(iii) an increased level of one or more free fatty acids relative to the level of the one or more free fatty acids in a wt animal;
(iv) an increased triglyceride level relative to a triglyceride level in a wt animal;
(v) an increased level of serum corticosterone relative to the level of corticosterone in a wt animal;
(vi) a reduced level of serum thyroid hormone (T4) compared to the level of T4 in a wt animal;
(v) increased liver weight compared to the weight of a liver in a wt animal;
(vi) increased bone mineral density relative to a wt animal, especially in a male animal; and
(vii) increased bone mineral content relative to a wt animal, especially in a male animal.

By "wild type (wt)" is meant an animal (which may include a human animal where appropriate) having average or normal or undisrupted levels of PYY expression, especially PYY(1-36) or PYY(3-36), and preferably an animal that is otherwise isogenic to the genetically-modified animal of the invention. As will be apparent to the skilled artisan a comparison between two animals (e.g., a genetically modified animal and a wt animal) is preferably performed with animals of approximately the same age and/or sex that have been maintained under approximately the same conditions. Methods for determining each of the phenotypes described supra will be apparent to the skilled artisan and/or described herein.

In another preferred embodiment, a genetically modified non-human animal in which the expression of precursor peptide YY (prePYY) or a derivative thereof is reduced or prevented comprises or exhibits one or more phenotypes selected from the group consisting of:
(i) increased body weight compared to a wt animal;
(ii) increased fat content compared to a wt animal;
(iii) increased fat mass compared to a wt animal; and
(iv) reduced glucose tolerance compared to a wt animal.

Preferably, such a phenotype occurs after the genetically modified non-human animal has aged for a time sufficient for the development of a progressive obesity disorder (e.g., approximately 20 weeks in a mouse).

In another preferred embodiment, a genetically modified non-human animal in which the expression of precursor peptide YY (prePYY) or a derivative thereof is reduced or prevented and which animal has been fed on a high-fat diet comprises or exhibits one or more phenotypes selected from the group consisting of:
(i) increased body weight compared to a wt animal;
(ii) increased fat content compared to a wt animal;
(iii) increased fat mass compared to a wt animal; and
(iv) reduced glucose tolerance compared to a wt animal.

As used herein, the term wild-type animal" or "wt" shall be taken to mean an animal of the same type (e.g., species and/or strain) as the genetically modified non-human animal of the invention that has a normal or unmodified level of expression of prePYY and/or a derivative thereof. Preferably, the wt animal has not been genetically modified. Furthermore, it is preferred that the wt animal differs from the genetically modified animal at the genetic level only in so far as the genetic modification.

The present invention clearly encompasses the above PYY-deficient animals that comprise additional modification(s) to their genomes, such as, for example, the knockout of an NPY-encoding gene, one or more Y receptor-encoding genes (e.g., Y-1, Y-Y2, Y-Y4, Y-Y5, Y-Y7 and combinations thereof) and/or a leptin-encoding gene and/or a pancreatic polypeptide-encoding gene (PP). Particularly preferred PYY-deficient (i.e., PYY$^{-/-}$) animals of the present invention have a genotype selected from the group consisting of: (i) PYY$^{-/-}$ NPY$^{-/-}$; (ii) PYY$^{-/-}$ Y-Y1$^{-/-}$; (iii) PYY$^{-/-}$ Y-Y2$^{-/-}$; (iv) PYY$^{-/-}$ Y-Y4$^{-/-}$; (v) PYY$^{-/-}$ Y-Y2$^{-/-}$ Y-Y4$^{-/-}$; (vi) PYY$^{-/-}$ leptin$^{-/-}$; and (vii) PYY$^{-/-}$ PP$^{-/-}$ and combinations thereof.

It is also within the scope of the present invention for the PYY-deficient animal to comprise a genetic background that confers an obesity or diabetes syndrome on an animal having functional PYY expression. Thus, PYY gene expression is disrupted or knocked-out in an animal having an obesity or diabetes syndrome phenotype. Such animals will have the genetic background selected from the group consisting of:
(i) yellow obese (Ay/a), a dominant mutation causes the ectopic, ubiquitous expression of the agouti protein, resulting in a condition similar to adult-onset obesity and non-insulin-dependent diabetes mellitus (Michaud et al., Proc Natl Acad. Sci. USA 91: 2562-2566, 1994);
(ii) Obese (ob/ob) having a mutation in the gene encoding leptin (Zhang et al., Nature 372: 425-432, 1994);
(iii) diabetes (db/db) having a mutation in the gene encoding the leptin receptor (Tartaglia et al., Cell 83: 1263-1271, 1995);
(iv) adipose (cpe/cpe) having a mutation in the gene encoding carboxypeptidase E (Naggert et al., Nat. Genet. 10: 135-142, 1995);
(v) tubby (tub/tub) having a mutation in a member of a new family of genes encoding tubby-like proteins (Kleyn et al., Cell 85: 281-290, 1996; Noben-Trauth et al., Nature 380: 534-548, 1996); and
(vi) combinations of any one or more of (i) to (v).

The present invention extends to any progeny of the PYY-deficient animal as described herein, preferably wherein said progeny has reduced or prevented expression of a precursor PYY or a derivative thereof. This includes any animals that are heterozygous PYY$^{+/-}$ or homozygous PYY$^{-/-}$ knockout animals, the only requirement being that they are deficient in expression of at least one PYY allele. Preferably, such animals are produced by targeted disruption of a PYY-encoding gene such as, for example, by using a targeting construct described herein.

The present invention also encompasses an isolated cell or tissue of or derived directly or indirectly from the genetically modified non-human animal described herein.

The present invention also provides a method of identifying a PYY-mediated phenotype, said method comprising comparing a phenotype of a wild-type animal to a phenotype of a genetically modified non-human animal in which the expression of precursor peptide YY (i.e., prePYY) or a derivative thereof e.g., PYY[1-36] or PYY[3-36] is reduced or prevented, wherein a modified or different phenotype is a PYY-mediated phenotype. Preferably, the method further comprising providing the genetically modified non-human animal. In this context, the term "providing" shall be taken to include producing the genetically modified non-human animal.

A knockout animal of the invention is useful as a screening platform for identifying a compound that modulates a phenotype of said animal. Clearly, such a method is useful for, for example, determining a compound for the treatment of obesity or bone diseases/disorders.

Accordingly, the present invention provides a method of identifying a compound that modulates a PYY-mediated phenotype of an animal, said method comprising:
(i) administering a compound to the genetically modified non-human animal of the present invention as described herein according to any embodiment hereof; and
(ii) comparing a PYY-mediated phenotype at (i) to the same phenotype of a wild type animal to which the compound has not been administered, wherein a comparable phenotype indicates that the compound modulates a PYY-mediated phenotype of the animal.

Alternatively, or in addition, the method comprises:
(i) administering a compound to a non-human animal expressing a functional PYY peptide and determining a PYY-mediated phenotype of the animal; and
(ii) comparing the PYY-mediated phenotype at (i) to the same phenotype of the genetically modified non-human animal of the present invention as described herein according to any embodiment hereof and to which the compound has not been administered, wherein a comparable phenotype indicates that the compound modulates a PYY-mediated phenotype of the animal.

Preferably, the PYY-mediated phenotype is selected from the group consisting of:
(i) fasting serum insulin level;
(ii) glucose induced serum insulin level;
(iii) a level of one or more free fatty acids;
(iv) a triglyceride level;
(v) a level of serum corticosterone;
(vi) a level of serum thyroid hormone (T4);
(v) liver weight;
(vi) bone mineral density;
(vii) bone mineral content;
(viii) obesity;
(ix) satiety;
(x) adiposity; and
(xi) bone deposition.

Preferably, the method further comprises one or more of the following:
(i) validating or otherwise confirming the binding and/or modulating activity of the identified compound;

(ii) determining a compound that binds to a Y receptor and/or reduces the PYY-mediated activation of a Y receptor prior to administering the compound to the genetically modified non-human animal;
(iii) producing or synthesizing the identified compound;
(iv) formulating the identified compound in a suitable carrier or excipient for administration to an animal subject;
(v) determining the structure of the identified compound;
(vi) providing the name or structure of the identified compound; and
(vii) providing the compound.

Preferably, the present invention provides a method of identifying a compound that modulates a PYY-mediated phenotype of an animal, said method comprising:
(i) administering a compound to a genetically modified non-human animal in which the expression of precursor peptide YY (i.e., prePYY) or a derivative thereof e.g., PYY[1-36] or PYY[3-36] is reduced or prevented; and
(ii) comparing a PYY-mediated phenotype at (i) to the same phenotype of a wild type animal to which the compound has not been administered, wherein a comparable phenotype indicates that the compound modulates a PYY-mediated phenotype of the animal.

In one embodiment the compound is an agonist of PYY or a mimetic of PYY that is capable of complementing the deficiency in the genetically modified animal with respect to PYY[1-36] and/or PYY[3-36] and/or other active fragment thereof. In accordance with this embodiment, the phenotype of the treated animal will more closely resembles the phenotype of a wild type animal to which the compound has not been administered. Preferably, the obesity phenotype of the treated animal more closely resembles the phenotype of an untreated wild type animal.

In another example, the present invention provides a method of identifying a compound that modulates a PYY-mediated phenotype of an animal, said method comprising:
(i) administering a compound to a non-human animal expressing a functional PYY peptide and determining a PYY-mediated phenotype of the animal; and
(ii) comparing the PYY-mediated phenotype at (i) to the same phenotype of a genetically modified non-human animal to which the compound has not been administered, said genetically modified non-human animal comprising a genetically modified non-human animal in which the expression of precursor peptide YY (i.e., prePYY) or a derivative thereof e.g., PYY[1-36] or PYY[3-36] is reduced or prevented, wherein a comparable phenotype indicates that the compound modulates a PYY-mediated phenotype of the animal.

In one embodiment the compound is an antagonist or inverse agonist of PYY e.g., PYY[1-36] or PYY[3-36] or other active fragment thereof. In accordance with this embodiment, the phenotype of the treated wild-type animal more closely resembles the phenotype of the genetically modified non-human animal comprising a genetic modification within its PYY locus to which the compound has not been administered (i.e., the phenotype of PYY-deficient animal of the present invention). Preferably, the bone phenotype of the treated animal more closely resembles the phenotype of an untreated genetically-modified animal e.g., by exhibiting higher bone mineral density and/or higher bone mineral content, indicative of enhanced bone remodeling activity.

More specific compound screens of the present invention will be apparent from the disclosure herein.

For example, the present invention provides screening platforms to identify compounds that modify the satiety signalling activity of PYY.

In one example, the present invention also provides a method of identifying a compound that reduces feeding behaviour, such as, for example, in the treatment of obesity or one or more complications arising therefrom e.g., Type II diabetes, said method comprising: (a) administering a compound to a genetically modified non-human animal in which the expression of precursor peptide YY (i.e., prePYY) or a derivative thereof e.g., PYY[1-36] or PYY[3-36] is reduced or prevented; and (b) determining the feeding behaviour of the animal, wherein reduced appetite or dietary intake of the animal compared to the appetite or dietary intake of a wild type animal to which the compound has not been administered indicates that the compound reduces feeding behaviour in a fasted animal.

In another example, the present invention also provides a method of identifying a compound that enhances feeding behaviour, such as, for example, in the treatment of anorexia, said method comprising: (a) administering a compound to a non-human animal expressing a functional PYY peptide and determining feeding behaviour of the animal; and (b) comparing the feeding behaviour of the animal to the feeding behaviour of a genetically modified non-human animal in which the expression of precursor peptide YY (i.e., prePYY) or a derivative thereof e.g., PYY[1-36] or PYY[3-36] is reduced or prevented, wherein a comparable feeding behaviour indicates that the compound enhances feeding behaviour.

For example, the present invention also provides screening platforms to identify compounds that modify the obesity phenotype mediated by PYY deficiency.

In one example, the present invention also provides a method of identifying a compound that enhances adiposity such as, for example, in the treatment of hypolipidemia (e.g. as observed in subjects suffering from abetalipoproteinemia, malnutrition or hematologic malignancies, such as acute myelocytic leukemia or chronic myelocytic leukemia), said method comprising: (a) administering a compound to a non-human animal expressing a functional PYY protein and determining the fat content of the animal; and (b) comparing the fat content at (a) to the fat content of a genetically modified non-human animal in which the expression of precursor peptide YY (i.e., prePYY) or a derivative thereof e.g., PYY[1-36] or PYY[3-36] is reduced or prevented, wherein a comparable fat content indicates that the compound enhances adiposity.

In another example, the present invention provides a method of identifying a compound that reduces adiposity, such as, for example, in the treatment of obesity or complications arising therefrom e.g. Type II diabetes, cardiovascular disease, hypertension, atherosclerosis, congestive heart failure, stroke, gallbladder disease, osteoarthritis, sleep apnoea, reproductive disorders such as polycystic ovarian syndrome, breast cancer, colon cancer, prostate cancer, insulin resistance, hypertension hypercholesterolemia, thromboembolic disease or Syndrome X, or in the treatment of neurodegenerative disorders or for cosmetic purposes such as bodybuilding or weight loss, said method comprising: (a) administering a compound to a genetically modified non-human animal in which the expression of precursor peptide YY (i.e., prePYY) or a derivative thereof e.g., PYY[1-36] or PYY[3-36] is reduced or prevented, and determining the fat content of the animal; (b) comparing the fat content at (a) to the fat content of a non-human animal expressing a functional PYY protein, wherein reduced fat content of the animal compared to the fat content of a PYY-deficient animal to which the compound has not been administered indicates that the compound reduces adiposity.

For example, the present invention provides screening platforms to identify compounds that modify the bone remodeling phenotype mediated by PYY.

In one example, the present invention also provides a method of identifying a compound that enhances bone remodeling e.g., as determined by bone mineral density and/or bone mineral content, such as, for example, in the treatment of bone disease e.g., osteomalacia, hyperostosis, osteoporosis (including involutional osteoporosis, post-menopausal osteoporosis, senile osteoporosis or glucocorticoid osteoporosis), bone fracture, bone segmental defect, periodontal defect, metastatic bone disease, or osteolytic bone disease (such as, for example, myeloma), said method comprising: (a) administering a compound to a non-human animal expressing a functional PYY protein and determining the bone mineral density and/or bone mineral content of the animal; and (b) comparing the bone mineral density and/or bone mineral content at (a) to the bone mineral density and/or bone mineral content of a genetically modified non-human animal in which the expression of precursor peptide YY (i.e., prePYY) or a derivative thereof e.g., PYY[1-36] or PYY[3-36] is reduced or prevented, wherein a comparable fat content indicates that the compound enhances bone remodeling.

In another example, the present invention provides a method of identifying a compound that reduces bone deposition e.g., as determined by bone mineral density and/or bone mineral content, such as, for example, in the treatment of bone disease e.g., osteopetrosis said method comprising: (a) administering a compound to a genetically modified non-human animal in which the expression of precursor peptide YY (i.e., prePYY) or a derivative thereof e.g., PYY[1-36] or PYY[3-36] is reduced or prevented, and determining the bone mineral density and/or bone mineral content of the animal; (b) comparing the bone mineral density and/or bone mineral content at (a) to the bone mineral density and/or bone mineral content of a non-human animal expressing a functional PYY protein, wherein reduced bone mineral density and/or bone mineral content of the animal compared to the bone mineral density and/or bone mineral content of a PYY-deficient animal to which the compound has not been administered indicates that the compound reduces bone deposition.

In each of the screening assays supra the present invention clearly contemplates the additional step of formulating the identified compound in a suitable carrier or excipient for administration to an animal subject. Alternatively or in addition, the subject method preferably further comprises producing or synthesizing the compound that is tested on the genetically modified animal. Alternatively or in addition, the subject method preferably comprises determining the structure of the compound. Alternatively or in addition, the subject method preferably comprises providing the name or structure of the compound.

In another embodiment, the subject method further comprises providing the compound.

The present invention clearly contemplates additional screening steps to those specifically stated herein, such as, for example, for the purposes of conducting high throughput primary screens to identify candidate compounds for screening in vivo using the animal model provided herein, or alternatively, for validating or otherwise confirming the binding and/or activity modulation activity of a compound identified using the animal model provided herein e.g., with respect to agonism or antagonism of one or more Y receptors by a PYY peptide. Accordingly, in an alternative embodiment the method of identifying a compound that modulates a PYY-mediated phenotype of an animal further comprises determining a compound that binds to a Y receptor and/or reduces the PYY-mediated activation of a Y receptor and/or activates a Y receptor.

In a particularly preferred embodiment, the present invention provides a process for identifying a compound that modulates a PYY-mediated phenotype of an animal said process comprising:
(i) determining a compound that binds to a Y receptor and/or reduces the PYY-mediated activation of a Y receptor;
(ii) administering a compound to a non-human animal expressing a functional PYY and determining a PYY-mediated phenotype of the animal;
(iii) comparing the PYY-mediated phenotype at (i) to the same phenotype of a genetically modified non-human animal to which the compound has not been administered, said genetically modified non-human animal comprising a genetically modified non-human animal in which the expression of precursor peptide YY (i.e., prePYY) or a derivative thereof e.g., PYY[1-36] or PYY[3-36] is reduced or prevented, wherein a comparable phenotype indicates that the compound modulates a PYY-mediated phenotype of the animal.

In an alternative embodiment, the present invention provides a process for identifying a compound that modulates a PYY-mediated phenotype of an animal said process comprising:
(i) determining a compound that binds to a Y receptor and/or reduces the PYY-mediated activation of a Y receptor;
(ii) administering a compound to a genetically modified non-human animal in which the expression of precursor peptide YY (i.e., prePYY) or a derivative thereof e.g., PYY[1-36] or PYY[3-36] is reduced or prevented; and
(ii) comparing a PYY-mediated phenotype at (i) to the same phenotype of a wild type animal to which the compound has not been administered, wherein a comparable phenotype indicates that the compound modulates a PYY-mediated phenotype of the animal.

To achieve high throughput, preferred methods for determining a compound that binds to a Y receptor and/or reduces the PYY-mediated activation of an NPY receptor and/or activates a Y receptor are performed in vitro in isolated cells or in situ using isolated neuron preparations. For example, competition assays can be performed in which the binding of a PYY peptide to a Y receptor expressed in transfected *Xenopus oocytes* or isolated HN9.10 cells stably expressing the receptor(s) is determined in the presence and absence of the compound. The PYY peptide may be detectably-labelled with a suitable reporter molecule, e.g., using a radioisotope.

A knockout animal of the present invention is also useful for producing an antibody against a PYY polypeptide of human origin e.g., comprising the amino acid sequence set forth in SEQ ID NO: 5, 26 or any one of SEQ ID NOs: 27-29. In fact, the inventors have actually used such genetically modified animals to produce monoclonal antibodies that bind specifically to human PYY[3-36] and preferably not at high affinity to human PYY[1-36], thereby overcoming the problems associated with non-specific polyclonal antibodies.

Accordingly, the present invention additionally provides a method for producing an antibody against PYY. In one embodiment this method comprises:
(i) immunizing a genetically modified non-human animal in which the expression of precursor peptide YY (i.e., prePYY) or a derivative thereof e.g., PYY[1-36] or PYY[3-36] is reduced or prevented with a PYY peptide or an epitope thereof; and
(ii) purifying antiserum or an antibody that binds to PYY from the genetically modified organism.

In a preferred embodiment, the antibodies are produced by immunization of animals with a peptide comprising the N-terminal portion of a PYY polypeptide of human origin, for example the nonamer peptide PYY[1-9] (SEQ ID NO: 29), or alternatively, a C-terminal portion of a PYY polypeptide that does not comprise the first two residues of a full-length PYY polypeptide, for example PYY[3-36] (SEQ ID NO: 28).

The present invention also provides an isolated antibody that binds specifically to a PYY polypeptide or fragment thereof, for example a human PYY[1-36] polypeptide or human PYY[3-36] polypeptide or fragment thereof, and preferably an isolated antibody that binds specifically to human PYY[1-36] (SEQ ID NO: 27) or a fragment thereof comprising the N-terminal two or three amino acid residues of SEQ ID NO: 27 or that binds specifically to a human PYY[3-36] (SEQ ID NO: 28) or a fragment thereof comprising residues from position 3 to position 13 of human PYY[1-36] (SEQ ID NO: 27).

In the present context, the term "binds specifically to PYY [1-36]" shall be taken to mean that the antibody binds more strongly or tightly to the full-length human PYY[1-36] polypeptide (SEQ ID NO: 27) than to a processed form of the full-length human PYY[3-36] polypeptide (SEQ ID NO: 28), thereby forming an antigen-antibody complex with said PYY [1-36] polypeptide and/or dissociating more slowly from an antigen-antibody complex with said PYY[1-36] relative to the dissociation of complexes between the antibody and the processed form of the full-length polypeptide.

In this context, such specific binding to human PYY[1-36] includes any antibody that binds specifically to any PYY peptide of humans that includes at least the N-terminal two or three amino acid residues of full-length PYY of humans e.g., PYY[1-2], PYY[1-3], PYY[1-4], PYY[1-5], PYY[1-6], PYY [1-7], PYY[1-8], PYY[1-9] (SEQ ID NO: 29), etc, or alternatively, binding to any PYY peptide that includes at least the second and third residues of full-length PYY e.g., PYY[2-3], PYY[2-4], PYY[2-5], PYY[2-6], PYY[2-7], PYY[2-8], PYY [2-9], etc.

Similarly, the term "binds specifically to PYY[3-36]" shall be taken to mean that the antibody binds more strongly or tightly to the human PYY[3-36] polypeptide (SEQ ID NO: 28) than to the full-length human PYY[1-36] polypeptide (SEQ ID NO: 27), thereby forming an antigen-antibody complex with said PYY[3-36] polypeptide, and/or dissociating more slowly from an antigen-antibody complex with said PYY[3-36] relative to the dissociation of complexes between the antibody and the full-length PYY[1-36] polypeptide.

In this context, such specific binding to human PYY[3-36] includes any antibody that binds specifically to any PYY peptide of humans that includes at least residues located between position 3 and position 13 of full-length PYY of humans, including a PYY[3-13] peptide (SEQ ID NO: 30) e.g., PYY[4-12], PYY[5-11], PYY[6-10], etc.

For the purposes of nomenclature, fragments or portions of full length PYY are specified herein by the format PYY[n-m], wherein n and m are integers defining amino acid coordinates with reference to the full-length PYY[1-36] of humans exemplified by the amino acid sequence set forth in SEQ ID NO: 27. For example, PYY[1-2] consists of residues at positions 1 and 2 of SEQ ID NO: 27; PYY[1-3] refers to residues from position 1 to position 3 inclusive of SEQ ID NO: 27; PYY[1-9] refers to residues from position 1 to position 9 inclusive of SEQ ID NO: 27; PYY[3-13] refers to residues from positions 3 to 13 inclusive of SEQ ID NO: 27; and PYY[3-36] refers to residues from position 3 to position 36 inclusive of SEQ ID NO: 27 (which is structurally-equivalent to the sequence set forth in SEQ ID NO: 28).

In a preferred embodiment, the monoclonal antibodies bind specifically to human PYY[1-36], for example antibodies produced by a hybridoma designated herein as 7K11, 7K11-F9, 7K11-C8 or 7K11-G3. Such antibodies are particularly useful as detection reagents for PYY[1-36] in immunoassays. For the purposes of nomenclature, such a monoclonal antibody is produced, for example, by a mouse hybridoma cell line designated 7K11-G3 deposited on Feb. 28, 2006 under the provisions of the Budapest treaty on the International Recognition of the Deposit of Microorganisms for the Purposes of Patent Procedure with the European Collection of Cell Cultures (ECACC) and assigned ATCC Accession No. 06022101.

Particularly preferred monoclonal antibodies in accordance with the present invention have the binding affinity of a monoclonal antibody produced by the hybridoma designated 7K11-G3 (ECACC Accession No. 06022101) and more preferably, are produced by the hybridoma designated 7K11-G3 (ECACC Accession No. 06022101).

In an alternative preferred embodiment, the monoclonal antibodies bind specifically to human PYY[3-36], for example antibodies produced by a hybridoma designated herein as 3L16. Such antibodies are particularly useful as detection reagents for PYY[3-36] in immunoassays. For the purposes of nomenclature, such a monoclonal antibody is produced, for example, by a mouse hybridoma cell line designated 3L16-N14 deposited on Feb. 28, 2006 under the provisions of the Budapest treaty on the International Recognition of the Deposit of Microorganisms for the Purposes of Patent Procedure with the European Collection of Cell Cultures (ECACC) and assigned ATCC Accession No. 06022102.

Particularly preferred monoclonal antibodies in accordance with the present invention have the binding affinity of a monoclonal antibody produced by the hybridoma 3L16-N14 (ECACC Accession No. 06022102) and more preferably, are produced by the hybridoma designated 3L16-N14 (ECACC Accession No. 06022102).

In an alternative preferred embodiment, the monoclonal antibodies bind non-specifically to human PYY[1-36] and to human PYY[3-36], for example antibodies produced by a hybridoma designated herein as 8C19, 2F3, 6C1, 4M20, 3K17, and 8A10. Such antibodies, whilst not specific for human PYY[1-36] or human PYY[3-36] are useful at least as capture reagents in an immunoassay.

The antibody may be a monoclonal antibody, recombinant antibody or a fragment of any one of said antibodies having the binding characteristics of an antibody produced by a deposited hybridoma described herein. The present invention also extends to analogues and derivatives of antibodies that possess the binding affinity of a monoclonal antibody produced by a deposited hybridoma described herein. It is to be understood in this context that the term "binding affinity of a deposited monoclonal antibody produced by a deposited hybridoma described herein" or similar term, means that the antibody or fragment or analogue or derivative binds specifically to human PYY[1-36] or human PYY[3-36] as does a monoclonal antibody produced by a deposited hybridoma. There is no requirement herein for such antibodies, fragments, homologues or orthologs to be equivalent in a quantitative sense to a deposited monoclonal antibody provided herein.

The present invention also provides a kit comprising one or more isolated antibodies of the invention as described with reference to any embodiment hereof and one or more reagents or other compositions of matter selected from the group consisting of (i) an antibody that binds non-specifically to a human PYY[1-36] polypeptide and to a human PYY[3-36] polypeptide; (ii) a PYY[1-36] peptide; (iii) a PYY[3-36] peptide; (iv) a reagent for performing an immunoassay; and (v) combinations of any one or more of (i) to (iii).

Preferably, the detection and capture antibodies may be part of a kit for detecting the presence or absence of PYY[1-36] or PYY[3-36], or for quantifying the amount of PYY[1-36] or PYY[3-36] in a sample. Preferred kits include an amount of one or more "detection" antibodies that bind specifically to PYY[1-36] or PYY[3-36] and one or more reagents for performing an immunoassay. Preferred kit reagents are selected from the group consisting of (i) an amount of a PYY[1-36] peptide and/or an amount of a PYY[3-36] peptide to which a "detection" antibody binds; (ii) an amount of one or more "detection" antibodies that bind specifically to PYY[1-36] or PYY[3-36]; and (iii) an amount of a "capture" antibody that binds non-specifically to PYY[1-36] and to PYY[3-36]. The antibodies are generally used in two-site and/or sandwich assay formats e.g., as a capture reagent to bind both PYY[1-36] and PYY[3-36], and as detection antibodies to detect the amount of PYY[1-36] or PYY[3-36] in the captured PYY[total] antigen. By detecting the relative amounts of PYY[1-36] and/or PYY[3-36] it is possible to determine the percentage or proportion or relative amount of PYY[1-36] and/or PYY[3-36] in a sample. Optionally, a control PYY[1-36] or PYY[3-36] peptide is used in varying amounts in control reactions to bind to an antibody of the invention, wherein the assay results for the peptide are used to produce a standard curve thereby providing for quantitative determination. Alternatively, an amount of the peptide can be used to demonstrate that the reaction conditions are suitable for detection of PYY[1-36] or PYY[3-36], or to demonstrate the limits of the reaction. Preferred kits will also include one or more other reagents suitable for performing an immunoassay such as, for example, one or more secondary antibodies wherein each of said antibodies is optionally labelled with a reporter molecule, and optionally, a substrate for each reporter molecule.

The present invention extends further to a cell line capable of producing a monoclonal antibody as described herein with reference to any embodiment hereof, i.e., a cell line producing a monoclonal antibody that binds specifically to a PYY polypeptide e.g., human PYY[1-36] or human PYY[3-36].

It will be appreciated by those skilled in the art that the antibodies of the present invention are useful for example for detecting, quantifying or localising PYY[1-36] and/or PYY[3-36] in test or assay samples, e.g., serum or other body fluid. It will be understood from the binding specificity/selectivity of the antibody of the invention that positive readout and negative readout assays can be used to detect the presence and absence, respectively, of PYY[1-36] or PYY[3-36], or the relative amounts of PYY[1-36] and PYY[3-36] or the ratio of PYY[1-36]:PYY[total] or the ratio PYY[3-36]:PYY[total].

Accordingly, the present invention provides a method comprising contacting a sample with one or more antibodies according to any embodiment described herein for a time and under conditions sufficient for an antigen-antibody complex to form and then detecting the complex, wherein the presence of detectable complex indicates the presence of said PYY polypeptide, and wherein the absence of detectable complex indicates that the sample does not express the PYY polypeptide. Preferably, the method comprises:
(i) contacting a sample with one or more antibodies according to claim 10 for a time and under conditions for an antigen-antibody complex to form; and
(ii) detecting the complex and determining the amount of one or more complex(es) formed, wherein the amount of a complex correlates positively with an amount of said PYY [1-36] or an amount of said PYY[3-36] in the sample.

Alternatively, or in addition, the method comprises:
(i) contacting a sample with a known amount of labelled PYY[1-36] and/or a known amount of PYY[3-36];
(ii) contacting the combined sample and labelled PYY with one or more antibodies according to any embodiment described herein for a time and under conditions sufficient for an antigen-antibody complex to form; and
(iii) detecting the amount of labelled PYY[1-36] and/or the amount of labelled PYY[3-36] in a complex formed, wherein the amount of labelled PYY[1-36] in the complex formed is inversely proportional to the amount of PYY[1-36] in the sample and wherein the amount of labelled PYY[3-36] in the complex is inversely proportional to the amount of PYY[3-36] in the sample.

Preferably, an amount of PYY[1-36] polypeptide and an amount of PYY[3-36] polypeptide are determined in a method supra. Preferably, a method supra additionally comprises a first step comprising contacting the sample with an antibody that binds non-specifically to a PYY[1-36] polypeptide and to a PYY[3-36] polypeptide for a time and under conditions sufficient for an antigen-antibody complex to form to thereby capture total PYY in the sample. Preferably, a method supra additionally comprises determining an amount of PYY[1-36] and/or an amount of PYY[3-36] and or PYY [total] in the sample.

The present invention also provides a process for determining a propensity of a subject to become obese or to develop a complication or medical condition associated with obesity, said process comprising performing a method for determining PYY[3-36] in a sample according to any embodiment described herein, wherein a low level of PYY[3-36] in the sample relative to an amount of PYY[3-36] in a normal or healthy human subject is indicative of a propensity for the subject to become obese or to develop one or more complications associated with obesity. The present in invention also provides a process for determining a propensity of a subject to become obese or to develop a complication or medical condition associated with obesity, said process comprising performing a method for determining PYY[total] in a sample according to any embodiment described herein, wherein a low level of PYY[total] in the sample relative to an amount of PYY[total] in a normal or healthy human subject is indicative of a propensity for the subject to become obese or to develop one or more complications associated with obesity. The present invention also provides a process for determining the propensity of a subject to become obese or to develop a complication or medical condition associated with obesity, said process comprising performing a method for determining PYY[3-36] in a sample according to any embodiment described herein, wherein a high level of PYY[3-36] in the sample relative to an amount of PYY[3-36] in a normal or healthy human subject is indicative of a low risk of obesity or low propensity for developing one or more complications associated with obesity. The present invention also provides a process for determining the propensity of a subject to develop a bone disease, said process comprising performing a method for determining PYY[total] in a sample according to any embodiment described herein, wherein a low level of PYY [total] in the sample relative to an amount of PYY[total] in a normal or healthy human subject is indicative of a low risk of developing a bone disease or disorder associated with deficient bone remodeling activity. The present invention also provides a process for determining the propensity of a subject to develop a bone disease, said process comprising performing a method for determining PYY[3-36] in a sample according to any embodiment described herein, wherein a low level of PYY[3-36] in the sample relative to an amount of PYY[3-36] in a normal or healthy human subject is indicative of a low risk of developing a bone disease or disorder associated with deficient bone remodeling activity.

More particularly, the present invention also provides a method comprising contacting a sample with an antibody that binds specifically to a PYY polypeptide of humans, for example PYY[1-36] or PYY[3-36] for a time and under conditions sufficient for an antigen-antibody complex to form and then detecting the complex, wherein the presence of detectable complex indicates the presence of said PYY polypeptide.

The present invention also provides a method comprising contacting a sample with an antibody that binds specifically to a PYY polypeptide, for example PYY[1-36] or PYY[3-36] for a time and under conditions sufficient for an antigen-antibody complex to form and then detecting the complex, wherein the absence of detectable complex indicates that the sample does not express the PYY polypeptide.

Various formats of the immunoassay of the invention are within the capabilities of a skilled artisan without undue experimentation. For example, a monoclonal antibody that binds to both PYY[1-36] and PYY[3-36] is used as a capture reagent to bind all PYY in a sample, and specific anti-PYY [3-36] antibody is used to determine the amount of PYY[3-36] in the bound sample. Alternatively, or in addition in the same or a different reaction, a specific anti-PYY[1-36] antibody is used to determine the amount of PYY[1-36] in the bound sample. Where both PYY[1-36] and PYY[3-36] are determined, the ratio of PYY[3-36]:PYY[1-36] is then determined. Alternatively, anti-Ig is used to separately bind the specific anti-PYY[1-36] and specific anti-PYY[3-36] antibodies, the bound antibodies contacted with PYY in a sample, and the ratio of bound PYY[3-36]:PYY[1-36] determined. These reactions are performed by ELISA, RIA or chemiluminescent formats, amongst others.

For quantitation, a detected signal obtained using a standard immunoassay format is generally converted to a numerical amount or concentration of the PYY polypeptide, by comparing the assay readout value to a standard, e.g., a standard curve of assay values produced using known amounts of PYY[1-36] or PYY[3-36], or alternatively, a standard curve of assay values produced using s having desirable amounts of PYY[1-36] or PYY[3-36] for specific applications. Accordingly, the present invention also provides a method for determining an amount of a PYY polypeptide e.g., PYY[1-36] or PYY[3-36] in a sample, said method comprising contacting the sample with the antibody of the present invention as described according to any embodiment herein for a time and under conditions sufficient for an antigen-antibody complex to form, detecting the complex and determining the amount of complex formed, wherein the amount of complex correlates positively with an amount of said PYY polypeptide.

The antibodies, kits and immunoassays of the present invention are particularly useful for determining the propensity of a subject to become obese or to develop one or more complications associated with obesity e.g., Type II diabetes, cardiovascular disease, hypertension, atherosclerosis, congestive heart failure, stroke, gallbladder disease, osteoarthritis, sleep apnoea, reproductive disorders such as polycystic ovarian syndrome, breast cancer, colon cancer, prostate cancer, insulin resistance, hypertension hypercholesterolemia, thromboembolic disease or Syndrome X. Accordingly, the present invention also provides a method for determining the propensity of a subject to become obese or to develop a complication or medical condition associated with obesity, said method comprising performing an immunoassay as described with reference to any embodiment herein and determining the amount or proportion of PYY[1-36] and/or PYY [3-36] or the relative amounts of PYY[1-36] and PYY[3-36] in a sample from the subject. Preferably, such immunoassays are performed on patient serum or a fraction thereof containing PYY, preferably serum that has been obtained previously from the subject. In accordance with this embodiment, a low level of PYY in serum or a fraction thereof relative to a normal or healthy human subject is indicative of a propensity for the subject to become obese or to develop one or more complications associated with obesity.

The antibodies, kits and immunoassays of the present invention are also useful for determining the propensity of a subject to develop a bone disease e.g., one or more bone diseases selected from the group consisting of osteomalacia, hyperostosis, osteoporosis (including involutional osteoporosis, post-menopausal osteoporosis, senile osteoporosis or glucocorticoid osteoporosis), bone fracture, bone segmental defect, periodontal defect, metastatic bone disease, osteolytic bone disease (such as, for example, myeloma) or osteopetrosis. Accordingly, the present invention also provides a method for determining the propensity of a subject to develop a bone disease, said method comprising performing an immunoassay as described with reference to any embodiment herein and determining the amount or proportion of PYY[1-36] and/or PYY[3-36] or the relative amounts of PYY[1-36] and PYY[3-36] in a sample from the subject. Preferably, such immunoassays are performed on patient serum or a fraction thereof containing PYY, preferably serum that has been obtained previously from the subject. In accordance with this embodiment, a low level of PYY in serum or a fraction thereof relative to a normal or healthy human subject is indicative of a propensity for the subject to develop osteopetrosis or abnormal bone deposition. In contrast, a high level of PYY in serum or a fraction thereof relative to a normal or healthy human subject is indicative of a propensity for the subject to develop a bone disease or disorder associated with deficient bone remodeling activity e.g., osteoporosis.

DETAILED DESCRIPTION OF THE PREFERRED EMBODIMENTS

Precursor Peptide YY and Derivatives Thereof

Figure 1A:
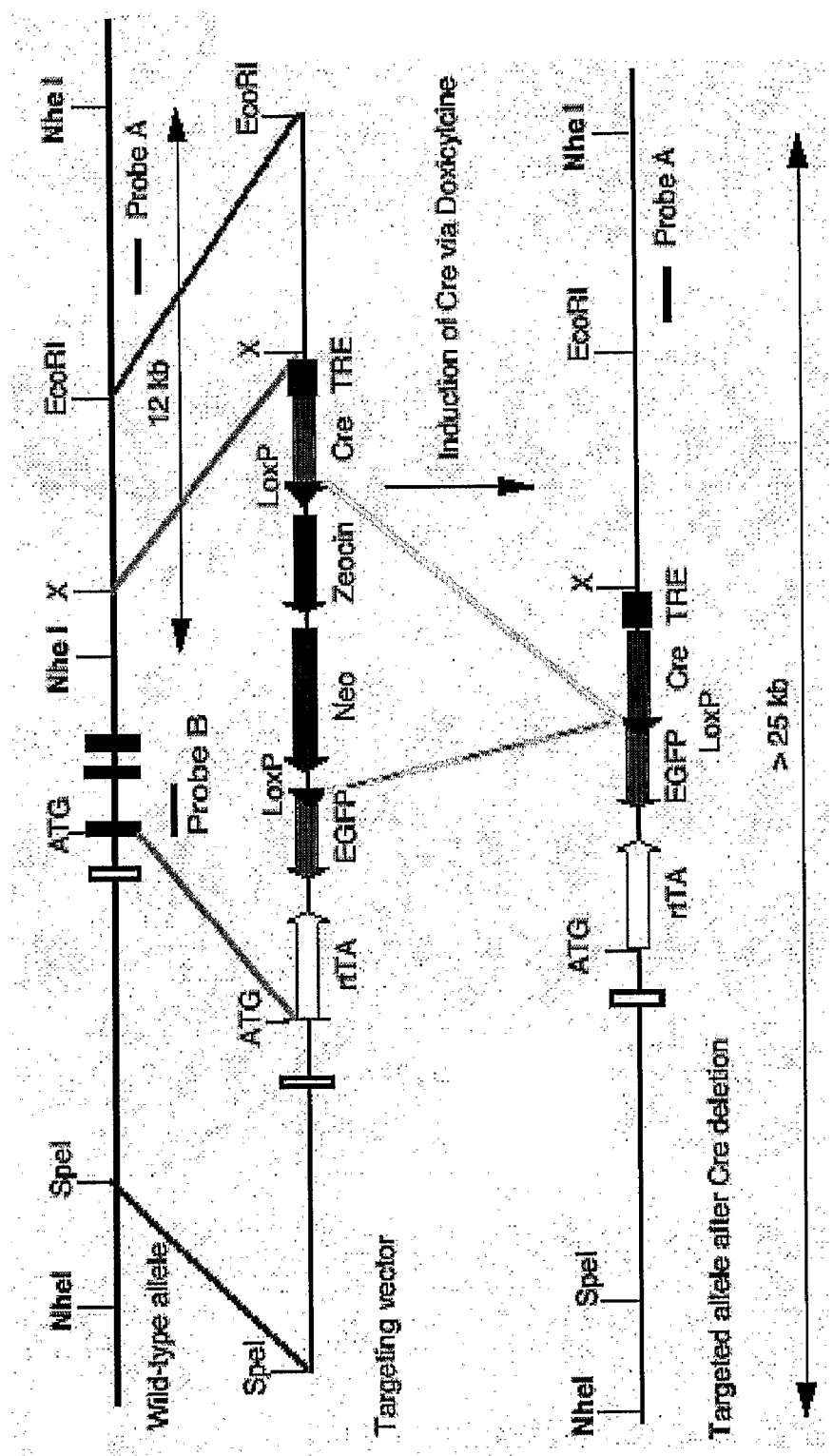
FIG. 1a is a schematic representation showing a targeting vector design and screening strategy. Bars indicate the position of probes used for Southern analysis of genomic DNA from targeted ES cells as well as knockout animals.

As used herein, the term "precursor peptide YY" or "prePYY" shall be taken to mean any peptide, polypeptide or protein comprising an amino acid sequence at least about 80% amino acid sequence identity to the amino acid sequence set forth in any one of SEQ ID NOs: 2, 5, 7 or 9. The amino acid sequence of mouse PYY is set forth in SEQ ID NO: 2; the amino acid sequence of human PYY is set forth in SEQ ID NO: 5; the amino acid sequence of chimpanzee PYY is set forth in SEQ ID NO: 7; and the amino acid sequence of rat PYY is set forth in SEQ ID NO: 9.

Preferably, the degree of sequence identity is at least about 85%, more preferably, at least about 90% identical or 95% identical or 98% identical.

In another embodiment, prePYY is a peptide, polypeptide or protein encoded by a nucleic acid comprising a nucleotide sequence at least about 80% identical to a nucleotide sequence set forth in any one of SEQ ID NOs: 1, 3, 4, 6 or 8. Preferably, the degree of sequence identity is at least about 85%, more preferably, at least about 90% identical or 95% identical or 98% identical.

In determining whether or not two amino acid sequences fall within the defined percentage identity limits supra, those skilled in the art will be aware that it is possible to conduct a side-by-side comparison of the amino acid sequences. In such comparisons or alignments, differences will arise in the positioning of non-identical residues depending upon the algorithm used to perform the alignment. In the present context, references to percentage identities and similarities between two or more amino acid sequences shall be taken to refer to the number of identical and similar residues respectively, between said sequences as determined using any standard algorithm known to those skilled in the art. In particular, amino acid identities and similarities are calculated using software of the Computer Genetics Group, Inc., University Research Park, Maddison, Wis., United States of America, e.g., using the GAP program of Devereaux et al., *Nucl. Acids Res.* 12, 387-395, 1984, which utilizes the algorithm of Needleman and Wunsch, *J. Mol. Biol.* 48, 443-453, 1970. Alternatively, the CLUSTAL W algorithm of Thompson et al., *Nucl. Acids Res.* 22, 4673-4680, 1994, is used to obtain an alignment of multiple sequences, wherein it is necessary or desirable to maximize the number of identical/similar residues and to minimize the number and/or length of sequence gaps in the alignment.

Alternatively, a suite of commonly used and freely available sequence comparison algorithms is provided by the National Center for Biotechnology Information (NCBI) Basic Local Alignment Search Tool (BLAST) (Altschul et al. *J. Mol. Biol.* 215: 403-410, 1990), which is available from several sources, including the NCBI, Bethesda, Md. The BLAST software suite includes various sequence analysis programs including "blastn," that is used to align a known nucleotide sequence with other polynucleotide sequences from a variety of databases and "blastp" used to align a known amino acid sequence with one or more sequences from one or more databases. Also available is a tool called "BLAST 2 Sequences" that is used for direct pairwise comparison of two nucleotide sequences.

As used herein the term "NCBI" shall be taken to mean the database of the National Center for Biotechnology Information at the National Library of Medicine at the National Institutes of Health of the Government of the United States of America, Bethesda, Md., 20894.

In determining whether or not two nucleotide sequences fall within a particular percentage identity limitation recited herein, those skilled in the art will be aware that it is necessary to conduct a side-by-side comparison or multiple alignment of sequences. In such comparisons or alignments, differences may arise in the positioning of non-identical residues, depending upon the algorithm used to perform the alignment. In the present context, reference to a percentage identity between two or more nucleotide sequences shall be taken to refer to the number of identical residues between said sequences as determined using any standard algorithm known to those skilled in the art. For example, nucleotide sequences may be aligned and their identity calculated using the BEST-FIT program or other appropriate program of the Computer Genetics Group, Inc., University Research Park, Madison, Wis., United States of America (Devereaux et al, Nucl. Acids Res. 12, 387-395, 1984). As discussed supra, BLAST is also useful for aligning nucleotide sequences and determining percentage identity.

As used herein, the term "prePYY derivative" shall be taken to mean a peptide, polypeptide or protein that is derived from a prePYY protein, e.g., by post-translational processing. For example, a signal peptide is cleaved from prePYY to produce a mature active PYY. By way of example, the amino acid sequence of a mature mouse PYY peptide is set forth in SEQ ID NO: 10.

Furthermore, the two N-terminal peptides are known to be cleaved from PYY by the protein dipeptidyl peptidase IV to produce PYY[3-36]. By way of exemplification, the amino acid sequence of mouse PYY[3-36] is set forth in SEQ ID NO: 11

Accordingly, it will be apparent to the skilled artisan that the present invention additionally encompasses a genetically modified non-human animal in which the expression of mature PYY or PYY[3-36] is reduced or prevented. For example, such a genetically modified non-human animal comprises a mutant nucleic acid encoding PYY that prevents the formation of, for example, mature PYY or PYY[3-36] (e.g., by mutating a protease cleavage site). Suitable methods for the production of such a non-human animal will be apparent to the skilled artisan and/or described herein.

A Transgenic Model of Obesity

As exemplified herein, the present inventors have produced a mouse in which the expression of prePYY is prevented, by gene targeting means. However, the present invention contemplates additional non-human animals wherein the expression of PYY is reduced or prevented, such as, for example, a rat, a pig, a sheep or a non-human primate.

Furthermore, the present invention contemplates an additional non-human animal in which the expression of a derivative of prePYY (e.g., mature PYY or PYY[3-36]) is reduced or prevented.

In particular, the present invention provides a genetically modified non-human mammal which lacks a functional prePYY gene referred to herein as a "non-human prePYY knockout mammal" or a "prePYY knockout mammal". However, the present invention contemplates any non-human prePYY knockout animal. Such an animal is produced using a method described herein and/or known in the art.

Preferably, the genome of the prePYY knockout animal comprises at least one non-functional allele for the endogenous prePYY gene of said mammal. Accordingly, the invention provides a source of a cell, a tissue, a cellular extract, an organelle or an animal useful for elucidating the function of PYY in an intact animal whose genomes comprise one copy of a wild-type prePYY gene or no copies of a functional prePYY gene. Furthermore, the invention provides a source of a cell, a tissue, a cellular extract, an organelle or an animal useful for determining a mimetic of PYY.

As the structure and function of PYY and derivatives thereof is conserved between animal species, particularly, mammalian species (e.g., between mouse and human) the effect of reducing the expression of prePYY or a derivative thereof in a non-human mammal is indicative of this effect in a human, e.g., a mouse, is a model system for the effect/s of such silencing in a human. Furthermore, a compound that is a mimetic of PYY determined using such a model organism is also considered an attractive target for treating a disease, disorder or phenotype associated with reduced PYY or prePYY expression in a human or non-human animal.

Those of skill in the art will recognize that a "knockout animal" refers to an animal in which a gene is functionally inactivated and preferably, disrupted. The disruption introduces a chromosomal defect (e.g., mutation or alteration) in the prePYY gene at a point in the nucleic acid sequence that is necessary for either the expression of the prePYY gene ore a derivative thereof or the production of a functional PYY protein or a derivative thereof. Accordingly, the introduction of the disruption inactivates the endogenous target gene (e.g., a prePYY gene).

As used herein the terms "disruption" and "functional inactivation" shall be taken to mean a partial or complete reduction in the expression and/or function of a prePYY polypeptide or a derivative thereof encoded by the endogenous gene of a single type of cell, selected cells or all cells of a non-human transgenic PYY knockout animal. For example, a prePYY knockout animal is unable to express prePYY in those cells in which this gene is expressed in nature or in a class of cells in which the gene is expressed in nature. Alternatively, or in addition, a disrupted prePYY gene is unable to produce a derivative of prePYY, such as, for example, a derivative selected from the group consisting mature PYY or PYY[3-36] and mixtures thereof. Thus, according to the instant invention the expression or function of a prePYY gene product (or derivative thereof) can be completely or partially disrupted or reduced (e.g., by 50%, 75%, 80%, 90%, 95% or more) in a selected group of cells (e.g., a tissue or organ) or in the entire animal.

As used herein the term "a functionally disrupted PYY gene" includes a modified PYY gene which either fails to express any polypeptide product or which expresses a truncated protein having less than the entire amino acid polypeptide chain of a wild-type protein or a derivative thereof and is non-functional (partially or completely non-functional).

Disruption of the PYY gene or a region or derivative thereof is accomplished by any of a variety of methods known to those of skill in the art, for example, gene targeting using homologous recombination.

For example, the invention provides a knockout animal whose genome comprises either a homozygous or heterozygous disruption of its PYY gene or a region thereof. A knockout mammal whose genome comprises a homozygous disruption is characterized by somatic and/or germ cells which contain two non-functional (disrupted) alleles of the PYY gene while a knockout mutant whose genome comprises a heterologous disruption is characterized by somatic and/or germ cells which contain one wild-type allele and one non-functional allele of the PYY gene.

As used herein, the term "genotype" refers to the genetic makeup of an animal with respect to the PYY chromosomal locus. More specifically, the term genotype refers to the status of the animal's PYY alleles, which can either be intact (e.g., wild-type or +/+); or disrupted (e.g., knockout) in a manner which confers either a heterozygous (e.g., +/−); or homozygous (−/−) knockout genotype.

The present invention also provides a method for producing a non-human mammal which lacks a functional PYY gene. Methods for producing a "knockout animal" are known in the art and described, for example, in Nagy et al eds. *Manipulating the Mouse Embryo*, Cold Spring Harbor Laboratory, 3rd Edition, 2002, ISBN 0879695749 and Tymms and Kola eds *Gene Knockout Protocols*, Humana Press, 2001, ISBN: 0896035727.

To produce a mutant mouse strain by homologous recombination, two major elements are generally used: (i) an embryonic stem (ES) cell line, capable of contributing to the germ line of the mammal of interest; and (ii) a targeting construct containing target-gene sequences with the desired mutation.

ES cell lines are generally derived from the inner cell mass of a blastocyst-stage embryo. The targeting construct is transfected into cultured ES cells. Homologous recombination occurs in a number of the transfected cells, resulting in introduction of the mutation present in the targeting construct into the target gene. Once identified, mutant ES cell clones are microinjected into a normal blastocyst to produce a chimeric animal, e.g. a chimeric mouse. As ES cell lines retain the ability to differentiate into every cell type present in the animal, the chimera can have tissues, including the germ line cells, with contribution from both the normal blastocyst and the mutant ES cells. Breeding germ-line chimeras yields animals that are heterozygous for the mutation introduced into the ES cell, and that can be interbred to produce homozygous mutant mice.

Production of a Knock-Out (Gene-Targeting) Construct

One of two configurations of constructs is generally used for a vector for homologous recombination, i.e., an insertion construct or a replacement construct.

An insertion construct comprises a region of homology to the target gene cloned as a single continuous sequence. The insertion construct additionally comprises a nucleic acid that is to be inserted into the target gene positioned adjacent to and, if required, in-frame with the region of homology. The insertion vector is then linearized, e.g., by cleavage of a unique restriction site within the region of homology. Homologous recombination introduces the insertion construct sequences and any adjacent nucleic acid into the homologous site of the target gene, interrupting normal target-gene structure by adding an additional sequence, for example, a LoxP site. Such a vector is useful for, for example, introducing one or more LoxP sites flanking a region of interest in the prePYY gene or for introducing a mutation that alters, for example, the amino acid composition of prePYY or PYY (e.g., for removing a cleavage site for a proteolytic enzyme, e.g., dipeptidyl peptidase IV or for producing only one form of PYY, e.g., PYY[3-36]).

A replacement construct is more commonly used to knockout a gene of interest. This form of construct contains two regions of homology to the target gene located on either side of a heterologous nucleic acid (for example, encoding one or more positive selectable markers, such as, for example, a fluorescent protein (e.g. enhanced green fluorescent protein), β-galactosidase, an antibiotic resistance protein (e.g. neomycin resistance or zeocin resistance) or a fusion protein (e.g. β-galactosidase—neomycin resistance protein, β-geo). Homologous recombination proceeds by at least two recombination events (or a double cross-over event) that leads to the replacement of target-gene sequences with the replacement-construct sequences. More specifically, each region of homology in the vector induces at least one recombination event that leads to the heterologous nucleic acid in the vector replacing the nucleic acid located between the regions of homology in the target gene.

The present invention provides a vector construct (e.g., a prePYY targeting vector or prePYY targeting construct) designed to disrupt the function of a wild-type (endogenous) mammalian prePYY gene. In general terms, an effective prePYY targeting vector comprises a nucleic acid comprising a nucleotide sequence that is effective for homologous recombination with the PYY gene. For example, a replacement targeting vector comprises at least two regions of nucleic acid that are substantially identical to a genomic sequence of the prePYY gene or a region thereof. As will be apparent to the skilled artisan, some degree of non-identity does not significantly adversely affect the gene targeting capability of a construct of the invention. However, a higher the degree of identity between the regions of homology in the vector and the gene increases the likelihood of effective homologous recombination. Accordingly, it is preferred that a region of a vector homologous to a target nucleic acid comprises a nucleotide sequence that is at least about 80% identical to the target sequence, more preferably, 90% or 95% identical.

Longer regions of homology are useful for inducing homologous recombination at the site of a PYY gene. However, this region need not be so long so as to be unwieldy. Preferably, each region of homology comprises at least about 1500 bp that is substantially identical to a target sequence, more preferably, 2000 bp and even more preferably, at least about 3000 bp.

One of skill in the art will recognize that any PYY genomic nucleotide sequence of appropriate length and composition to facilitate homologous recombination at a specific site that has been preselected for disruption can be employed to construct a PYY targeting vector. Guidelines for the selection and use of sequences are described for example in Deng and Cappecchi, *Mol. Cell. Biol.,* 12:3365-3371, 1992 and Bollag, et al., *Annu. Rev. Genet.,* 23:199-225, 1989.

Suitable sites for gene targeting will also be apparent to the skilled artisan. As exemplified herein, a wild-type prePYY gene is mutated and/or disrupted by inserting a recombinant nucleic acid sequence (e.g., a PYY targeting construct or vector) into all or a portion of the PYY gene locus. Alternatively, a targeting construct is designed to recombine with a particular portion within an enhancer, promoter, coding region, start codon, noncoding sequence, introns or exons of the PYY gene (preferably, a region required for expression of a functional PYY). Alternatively, a targeting construct comprises a recombinant nucleic acid that introduces a stop codon after or within exon 1 of the PYY gene.

Each of the regions of identity flank a nucleic acid that encodes, for example, a selectable marker gene. For example, the selectable marker is flanked by a region homologous to or substantially identical to a region of the PYY genomic DNA 5' to exon 1 and another region homologous to or substantially identical to a region of the PYY genomic DNA 3' to exon 3.

Suitable targeting constructs of the invention are prepared using standard molecular biology techniques known to those of skill in the art. For example, techniques useful for the preparation of suitable vectors are described by Maniatis, et al., Molecular Cloning: A Laboratory Manual, Cold Spring Harbor Laboratory, Cold Spring Harbor, N.Y. An appropriate vector includes, for example, an insertion vector such as the insertion vector described by Capecchi, M. R., *Science,* 244: 1288-92, 1989; or a vector based on a promoter trap strategy or a polyadenylation trap, or "tag-and-exchange" strategy described by Bradley, et al., *Biotechnology,* 10:543-539, 1992; or Askew, et al., *Mol. Cell. Biol.,* 13:4115-5124, 199.

One of skill in the art will readily recognize that any of a number of appropriate vectors known in the art can be used as the basis of a suitable targeting vector. In practice, any vector that is capable of accommodating the recombinant nucleic acid required for homologous recombination and to disrupt the target gene is useful. For example, pBR322, pACY164, pKK223-3, pUC8, pKG, pUC19, pLG339, pR290, pKC101 or other plasmid vectors can be used. Alternatively, a viral vector such as the lambda gt11 vector system is useful as the backbone (e.g. cassette) for a targeting construct.

In an example of the invention, the targeting vector comprises one or more recombination sites, such as, for example, a LoxP site (which is a recognition site of the P1 recombination enzyme Cre) or a fit site (which is a recognition site of the yeast recombinase flp). Methods for using such recombinase sites for the production of a targeting vector and for the production of a knockout mammal are known in the art and described, for example, in Fiering et al., 1995; Vooijs et al., 1998.

For example, by positioning at least two loxP sites (SEQ ID NO: 23) in the same orientation near each other in a nucleic acid, it is possible to excise the nucleic acid intervening the LoxP sites by expressing the enzyme, Cre (SEQ ID NO: 25), in the cell thereby, leaving a single loxP site in the original DNA and the remaining loxP sites in a circular piece of DNA containing the intervening sequence. Accordingly, loxP sites or frt sites that are inserted flanking a region of the PYY gene or the entire PYY gene are useful for the removal of the intervening sequence.

Such a system is additionally useful for, for example, producing a conditional knockout animal. Conditional silencing or knocking out a gene means that that the silencing of the gene is dependent upon an external stimulus that may be spatially and/or temporally controlled. For example, the PYY gene is flanked by two or more loxP sites (i.e., it is "floxed") and upon expression of Cre recombinase the gene is removed. The expression of Cre may be spatially controlled (e.g., under the control of a tissue or cell specific promoter) and/or may be temporally controlled (e.g. under control of a promoter that is expressed at a certain stage of development or that is inducible, e.g., a tet inducible or repressible promoter).

Recombination sites (e.g., loxP or frt) are also useful for removing one or more selectable markers and or producing a new selectable marker following integration into the genome of a cell or organism (e.g., as exemplified herein). For example, a replacement targeting construct comprises one or more selectable markers flanked by recombination sites. Following successful targeting Cre is expressed (e.g. an expression construct that expresses Cre is introduced into a cell) or Cre is introduced into a cell or a mammal comprising the targeting construct is crossed with another mammal expressing Cre) and the selectable marker is removed. Such a system is useful for, for example, removing a region of a targeting construct that includes, for example, a promoter that may alter the expression of genes other than the gene of interest or encodes a polypeptide that is toxic to a subject.

Alternatively, removing a selectable marker is useful for determining a cell in which Cre has been successfully expressed.

As exemplified herein, the present inventors have used Cre that is placed in operable connection with a tetracycline response element. The reverse Tet repressor (rTetR) is placed in operable connection with an endogenous PYY promoter. Accordingly, in those tissues that Cre is expressed a floxed sequence is removed.

The specific knockout construct provided by the present inventors comprises a plurality of selectable markers, e.g., neomycin resistance gene, green fluorescent protein (GFP) and zeocin resistance gene in addition to recombination sites and a nucleic acid encoding Cre. In particular, the expression construct comprises a rTeTR element that following homologous recombination is placed in operable connection with the prePYY promoter. The vector additionally comprises an EGFP gene arranged in the opposite orientation to the rTeTR element, said EGFP gene modified such that its start codon is replaced with a loxP site. Adjacent to the EGFP is a neomycin resistance gene linked to a phosphoglycerate kinase I gene promoter (PGK-neo) and a zeocin resistance gene also cloned in the reverse orientation. Adjacent to the selectable markers is a nucleic acid encoding Cre placed in operable connection with a tet-response element also in a 3' to 5' orientation. The Cre encoding nucleic acid is modified to replace its STOP codon with another loxP site. Flanking this cassette are two regions of homology to the PYY locus in mouse. A diagrammatic representation of this targeting construct is shown n FIG. 1a.

A cell comprising the exemplified vector is selected using a neomycin derivative (e.g., G418) and/or zeocin. Furthermore, a cell in which the construct has integrated into the genome at the correct site, i.e., by homologous recombination expresses the rTeTR under control of the PYY promoter. Addition of tetracycline or a derivative thereof (e.g., doxycycline) causes rTeTR to induce expression of Cre, thereby excising the neomycin and zeocin resistance genes and producing a Cre-EGFP fusion protein.

While the present invention specifically exemplifies a construct that replaces a preNPY gene, the invention clearly contemplates a vector for replacement of a part of a preNPY gene. For example, a construct is produced to replace only those regions of the gene that encode mature PYY, or to remove a region of the gene to ensure production of only PYY[3-36]. For example, a gene encoding PYY is replaced with a gene or a minigene encoding only PYY[3-36] (i.e., lacking the first two amino aids).

Alternatively, an insertion or replacement vector is produced to modify a prePYY gene such that it cannot be modified in vivo, for example, to produce PYY[3-36]. In this regard, mature PYY is cleaved by dipeptidyl peptidase IV, an enzyme that recognizes the motif Xaa-Xbb-/-Xcc at the amino-terminus of a protein, wherein Xaa is any amino acid, Xbb is preferably proline and Xcc is not proline or hydroxyproline. For example, by changing the amino acid from alanine at position 3 of mature mouse PYY (SEQ ID NO: 10) to a proline and/or changing the amino acid from proline at position 2 of mature mouse PYY (SEQ ID NO: 10) the production of PYY[3-36] is reduced. Preferably, the amino acid used in place of the alanine and/or proline does not substantially alter the activity of PYY. A suitable conservative amino acid change will be apparent to the skilled artisan.

Production of a PYY$^{-/-}$ Cell

Following production of a suitable gene construct, said construct is introduced into a relevant cell. Methods of introducing the gene constructs into a cell for expression are known to those skilled in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001). Means for introducing recombinant DNA into cells include, but are not limited to electroporation, microinjection, transfection mediated by DEAE-dextran, transfection mediated by calcium phosphate, transfection mediated by liposomes such as by using Lipofectamine (Invitrogen) and/or cellfectin (Invitrogen), transduction by Adenoviuses, Herpesviruses, Togaviruses or Retroviruses and microparticle bombardment such as by using DNA-coated tungsten or gold particles (Agacetus Inc., WI, USA). For example, a cell is electroporated with a targeted construct of the invention.

A suitable cell for the production of a knockout animal is, for example, an embryonic stem cell. An embryonic stem cell is a pluripotent cell isolated from the inner cell mass of mammalian blastocyst. ES cells can be cultured in vitro under appropriate culture conditions in an undifferentiated state and retain the ability to resume normal in vivo development as a result of being combined with blastocyst and introduced into the uterus of a pseudopregnant foster mother. Those of skill in the art will recognize that various stem cells and stem cell lines are known in the art, such as, for example, AB-1, HM-1, D3. CC1.2, E-14T62a, RW4 or JI (Teratomacarcinoma and Embryonic Stem Cells: A Practical Approach, E. J. Roberston, ed., IRL Press). Clearly, a suitable stem cell or stem cell line will depend upon the type of knockout mammal to be produced. For example, should a knockout mouse be desired a mouse ES cell line is used. Furthermore, should an inbred strain of knockout mice be preferred, an ES cell line derived from the same strain of mice that is to be used is preferred. Alternatively, a suitable stem cell line for production of a zebrafish knockout is described, for example, in Ma et al., *Proc. Natl. Acad. Sci. USA*, 98: 2461-2466, 1991.

Following transfection, a cell is maintained under conditions sufficient for homologous recombination to occur while maintaining the pluripotency of the ES cell.

In an example of the invention, an ES cell is selected that has homologously recombined to introduce the targeting vector into its genome (as opposed to random integration). A method used for eliminating cells in which the construct integrated into the genome randomly, thus further enriching for homologous recombinants, is known as positive-negative selection. Such methods are described, for example, in U.S. Pat. No. 5,464,764. Briefly, a homologous recombination construct useful for positive-negative selection comprise a negative selectable marker (e.g., herpes simplex virus thymidine kinase, HSV-TK) outside the region of homology to the target gene (i.e. in a region that will not be incorporated into the genome of a cell following homologous recombination). In the presence of the TK gene, a mammalian cell is sensitive to acyclovir and its analogs (e.g., gancyclovir, GANC). The HSV-TK enzyme activates this compound, resulting in its incorporation into growing DNA, causing chain termination and cell death. During homologous recombination, sequences outside the regions of homology to the target gene are lost due to recombination (i.e. crossing over). In contrast, during random integration substantially all of the sequences in the construct are retained as recombination usually occurs at the ends of the construct. The presence of the TK gene can be selected against by growing the cells in gancyclovir. A homologous recombinant will be G418-resistant and gancyclovir-resistant, whereas a clone in which the construct integrated randomly will be G418-resistant and gancyclovir-sensitive. Other markers that are lethal to cells have also been used in place of instead of TK and will be apparent to the skilled person (e.g., diphtheria toxin; Yagi et al., 1990). Alternatively, the present inventors have use the expression of Cre to excise a selectable marker and produce a new fusion protein to detect correct integration of a targeting construct in a host cell genome.

Alternatively, or in addition, a cell is screened using, for example, PCR or Southern blotting to determine a targeting construct that has integrated into the correct region of the genome rather than randomly integrated. Methods for such screening are known in the art, and described, for example, in Nagy et al eds. *Manipulating the Mouse Embryo*, Cold Spring Harbor Laboratory, 3rd Edition, 2002, ISBN 0879695749 and Tymms, Kola eds *Gene Knockout Protocols*, Humana Press, 2001, ISBN: 0896035727, Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Following selection of a cell that has integrated the targeting vector, should the vector comprise recombination sites, Cre may be introduced or expressed in the cells to remove regions of the genome, should this be desired.

Production of a PYY$^{-/-}$ Animal

Following production of an ES cell in which at least one copy of the prePYY gene has incorporated the targeting construct the cell is preferably grown to form an ES cell colony using methods known in the art. One or more cells from the colony are then used to produce a chimeric animal.

An example of a method used to generate chimeras involves injecting a genetically modified ES cell into the blastocoel cavity of a developing embryo. For example, should the targeted ES cell be of mouse origin, an ES cell is injected into the blastocoel cavity of a 3.5-day-old mouse embryo. The injected embryo is surgically implanted into the uterus of a foster mother, for example, a pseudopregnant female. A resultant offspring is a chimera as its tissues is derived from both the host embryo and from the ES cell. Should the ES cell populate the germ line, the chimera can pass an altered gene to offspring, resulting in a new mouse strain in which all cells contain an altered gene.

By breeding a mouse of the new mouse strain with a wild-type mouse offspring that are heterozygous for the mutation are produced, i.e., prePYY$^{+/-}$. However breeding two heterozygous mice, or two homozygous mice or a heterozygous mouse and a homozygous mouse produces at least some offspring that are homozygous for the mutation, i.e., prePYY$^{-/-}$.

The present invention clearly contemplates both heterozygous and homozygous knockout non-human mammals. For example, the present invention contemplates a genetically modified non-human mammal with a phenotype selected from the group consisting of prePYY$^{-/+}$, prePYY$^{-/-}$, prePYY$^{+/loxP}$, prePYY$^{loxP/loxP}$, prePYY$^{+/frt}$ and prePYY$^{frt/frt}$. As used herein, the term "−/−" shall be understood to symbolize a mouse that is homozygous for a mutation that silences a gene; "−/+" shall be taken to symbolize a mouse that is heterozygous for a mutation that silences a gene; "+/loxP" shall be taken to symbolize a mouse that is heterozygous for a gene or region thereof or that comprises a targeting construct or region thereof that is flanked by loxP sites; "loxP/loxP" shall be taken to symbolize a mouse that is homozygous for a gene or region thereof or that comprises a targeting construct or region thereof that is flanked by loxP sites; "+/frt" shall be taken to symbolize a mouse that is heterozygous for a gene or region thereof or that comprises a targeting construct or region thereof that is flanked by frt sites; and "frt/frt" shall be taken to symbolize a mouse that is homozygous for a gene or region thereof or that comprises a targeting construct or region thereof that is flanked by frt sites.

It is to be understood that the prePYY knockout mammals described herein can be produced by methods other than the embryonic stem cell method described above, for example by the pronuclear injection of recombinant genes into the pronuclei of a one-cell embryo or other gene targeting methods which do not rely on the use of a transfected ES cell, and that the exemplification of the single method outlined above is not intended to limit the scope of the invention to animals produced solely by this protocol.

For example, a knockout animal is produced using a nuclear transfer method. Essentially, such a method comprises performing homologous recombination in a suitable cell, such as, for example, a fibroblast (using a vector essentially as described herein). The nucleus of the fibroblast or the entire fibroblast is then inserted into an enucleated oocyte and the oocyte induced to grow and/or divide, e.g., using an electrical impulse. The resulting cell/s are then grown for a time sufficient for a blastocyst or an embryo to form and the blastocyst or embryo implanted into a suitable female. Any resulting animals are knockout animals. Suitable methods for the production of a knockout animal using nuclear transfer are known in the art and/or described, for example, in Kolber-Simonds et al., *Proc. Natl. Acad. Sci. USA*, 101: 7335-7340, 2004; McReath et al., Nature, 408:120, 2000; or reviewed in Gong and Rong, *Curr. Opin. Genet. Dev.* 13:215-20, 2003.

The present invention additionally contemplates an alternative method for producing a knockout animal that expresses a specific form of a PYY. For example, a knockout animal is produced that is incapable of expressing any form of PYY and this animal is then used to produce a transgenic animal that expresses a specific form of PYY, e.g., PYY[3-36] or PYY[1-36] (mature PYY). Methods for producing a suitable transgenic mouse will be apparent to the skilled artisan and described, for example, in Nagy et al eds. *Manipulating the Mouse Embryo*, Cold Spring Harbor Laboratory, 3rd Edition, 2002, ISBN 0879695749. Alternatively, a knockout animal of the invention is crossed with a transgenic animal to thereby introduce the transgene into a knockout animal.

As will be apparent from the preceding discussion, the present invention contemplates a non-human mammal (e.g. a mouse) that has been genetically modified to reduce the expression of any one or more forms of PYY, or a derivative thereof. For example, a modified form of the targeting vector described herein is useful for, for example, producing a mouse with reduced expression of PYY or a derivative thereof selected from the group consisting of prePYY, mature PYY and PYY[3-36]. The present inventors have clearly demonstrated production of a mouse in which the expression of all forms of PYY are reduced. For example, the present inventors have demonstrated the production of a mouse in which expression of all forms of PYY encoded by a nucleic acid comprising the sequence set forth in SEQ ID NO: 1 or 2 is reduced.

The present invention additionally contemplates a cell, a cell line, a cell culture, a primary tissue, a cellular extract or a cell organelle isolated from a PYY knockout animal of the instant invention. For example, a cell culture or cell line or cell is derived from any desired tissue or cell-type from a PYY knockout mouse. For example, a cell culture, or cell line or cell is derived a tissue or cell-type that express high levels of PYY in nature. Such a cell line is useful for, for example determining a PYY mimetic compound.

Tissue Specific Knockout Animals

An exemplified knockout animal of the present invention comprises a gene encoding a Cre protein operably linked (albeit indirectly linked) to a PYY promoter. Accordingly, the knockout animal expresses Cre in those tissues in which PYY is expressed. As a consequence the present invention provides a knockout animal of the invention expressing a recombinase in a tissue in which a PYY is expressed in nature.

As used herein, the term "recombinase" shall be taken to mean a peptide, polypeptide or protein capable of causing recombination between two specific sites in a nucleic acid. For example, a recombinase is a Cre recombinase or a flp recombinase.

As used herein, the term "Cre" shall be taken to mean a peptide, polypeptide or protein capable of causing recombination between two or more loxP sites. In this regard, Cre is capable of excising a nucleic acid located between two loxP sites in the same orientation. Alternatively, a Cre polypeptide is capable of inverting a nucleic acid located between two loxP sites in opposite orientations (i.e., causing an inversion). Preferably a Cre polypeptide comprises an amino acid sequence at least about 80% identical to the amino acid sequence set forth in SEQ ID NO: 25. Preferably, the degree of amino acid sequence identity is at least about 85% or 90% or 95% or 98%. Preferably, the Cre polypeptide is a lambda phage P1 Cre polypeptide.

As used herein, the term "PYY promote" shall be taken to mean a sequence of nucleotides that controls the expression of a PYY gene in its native environment (i.e., in a cell in which PYY is expressed in nature and not by recombinant means). By way of exemplification a nucleotide sequence comprising the nucleotide sequence of a PYY promoter or a fragment thereof is set forth in SEQ ID NO: 26.

As will be apparent to the skilled artisan, the knockout animal of the invention is useful for producing a conditional knockout of a nucleic acid, e.g., a gene. In particular, the knockout animal of the invention is useful for producing a genetically modified organism, wherein the genetic modification occurs in a cell in which PYY is expressed in nature, e.g., a neuron in the brainstem or an endocrine cell of the lower gastrointestinal tract. Accordingly, the present invention provides a method for producing a genetic modification in an animal comprising:
(i) producing an animal comprising a recombinase binding site linked to the 5' end and 3' end of a nucleic acid of interest; and
(ii) expressing in the animal a recombinase capable of binding to the recombinase binding sties, wherein said recombinase is expressed in a cell or tissue in which PYY is expressed in nature, thereby inducing recombination between the recombinase binding sites in said cell or tissue.

Preferably, the method comprises:
(i) producing an animal comprising a recombinase binding site linked to the 5' end and 3' end of a nucleic acid of interest;
(ii) breeding the animal (i) with a knockout animal of the invention that expresses a recombinase capable of binding to the recombinase binding sties, wherein said recombinase is expressed in a cell or tissue in which a PYY is expressed in nature, thereby inducing recombination between the recombinase binding sites in said cell or tissue; and
(iii) identifying or selecting an offspring that comprises a genetic modification in a cell or tissue in which PYY is expressed in nature.

Suitable methods for producing a nucleic acid defined by recombinase sites will be apparent to the skilled artisan and/or are described herein.

In a preferred embodiment, the recombinase site is a loxP site (SEQ ID NO: 23) and the recombinase is a Cre polypeptide.

As will be apparent from the description herein, the method for producing a genetic modification in an animal described herein is useful for, for example producing a tissue specific knockout of a gene in an animal and/or modifying a heterologous nucleic acid in an animal in a tissue specific manner (e.g., removing a selectable marker from the genome of a cell).

As the expression of Cre in the present invention is inducible (e.g., by administering tetracycline or an analogue therein), the present invention additionally provides a method for inducing a genetic modification in a cell or tissue in which PYY is expressed in nature. For example, in the case of a tissue specific knockout that is lethal in developing animals, the method of the invention is useful for inducing the knockout following the developmental stage of the animal.

For example, a knockout animal of the invention animal additionally comprising, for example a foxed nucleic acid of interest is produced but not exposed to tetracycline or an analogue thereof. To induce tissue specific excision of the foxed nucleic acid, the animal is fed tetracycline or an analogue thereof, e.g., in its water, to thereby induce expression of Cre in a tissue dependent manner.

Screening Methods to Identify Compounds that Modulate PYY-Mediated Phenotype(s)

The present invention additionally provides a method for identifying a compound that modulates PYY expression or activity, including one or more phenotypes of a genetically modified non-human animal in which the expression of prePYY or a derivative thereof is reduced or prevented or a cell derived therefrom. Such phenotypes are described herein with regard to the figures and/or examples. Clearly, such a method is useful for, for example, determining a compound for the treatment of obesity or bone disease.

In one embodiment, the present invention provides a method comprising:
(i) administering a compound to a genetically modified non-human animal deficient in prePYY or a derivative thereof; and
(ii) determining the fat content, fat mass and/or bodyweight of the animal, wherein reduced fat content, fat mass and/or bodyweight in the animal compared to an animal deficient in prePYY or a derivative thereof that has not been administered the compound indicates that the compound reduces fat content, fat mass and/or bodyweight.

Alternatively, the method comprises:
(i) administering a compound to a non-human animal expressing a functional PYY peptide; and
(ii) determining the fat content, fat mass and/or bodyweight of the animal, wherein a similar level of fat content, fat mass and/or bodyweight in the animal compared to the fat content, fat mass and/or bodyweight of a genetically modified non-human animal deficient in prePYY or a derivative thereof that has not been administered the compound indicates that the compound increases fat content, fat mass and/or bodyweight.

As used herein, the term "fat content" shall be taken to mean the total amount of fat in a subject, e.g. expressed as a percentage or fraction of total body weight. Methods for determining fat content include, for example, near infra-red analysis or dual X-ray absorptiometry (DXA) analysis.

Alternatively, the fat content of an animal of the invention is determined using an organic solvent (ether) extract of a dried sample followed by gravimetric measurement of fat, essentially as described by McNeal et al., *J. Assoc. Off. Anal. Chem.* 70:95-99, 1989.

As used herein, the term "fat mass" shall be taken to mean the weight or mass of fat in an organism. This measurement may be the mass of a specific region of fat in an organism, e.g., a fat pad (e.g., an inguinal fat pad, an epididymal fat pad or a periovarian fat pad, a retroperitoneal fat pad or a mesenteric fat pad), a the sum of a plurality of these regions. The fat mass of an organism is determined, for example, by removing a suitable region of fat and weighing it.

Methods for determining the bodyweight of an animal will be apparent to the skilled artisan.

In another example, the present invention provides a method comprising:
(i) administering a compound to a genetically modified non-human animal deficient in prePYY or a derivative thereof; and
(ii) determining the bone mineral content and/or bone mineral density of the animal, wherein reduced bone mineral density and/or reduced bone mineral content in the animal compared to an animal deficient in prePYY or a derivative thereof that has not been administered the compound indicates that the compound reduces bone mineral content and/or bone mineral density.

Alternatively, the method comprises:
(i) administering a compound to a non-human animal expressing a functional PYY peptide; and
(ii) determining the bone mineral content and/or bone mineral density of the animal, wherein a similar level of bone mineral content and/or bone mineral density in the animal compared to the bone mineral content and/or bone mineral density of a genetically modified non-human animal deficient in prePYY or a derivative thereof that has not been administered the compound indicates that the compound increases bone mineral content and/or bone mineral density.

Those skilled in the art are aware of standard methods for determining bone mineral content and/or bone mineral density e.g., DXA.

Generally, DXA analysis involves X-ray scanning of a sample, e.g., a non-human animal, at two different wavelengths. This form of analysis is based on the differential attenuation of low- and high-energy X-rays by bone, fat and other soft tissues. The fat and lean content of an animal can also be determined from this differential attenuation at each measurement location (pixel) of a total body scan that does not overlie bone and is reported to be independent of tissue thickness. A suitable method for determining fat content using DXA is described, for example, by Mazess et al., *Journal of American Clinical Nutrition*, 51: 1106-1112, 1990.

Near infra-red analysis is based on the principle that major organic sample components have absorption characteristics (due to vibrations arising from the stretching and bending of H associated with C, O, and N) in the near infrared region that are specific to the component.

In another embodiment, the present invention provides a method for determining a compound for reducing an enhanced level of triglycerides and/or reducing an enhanced level of free fatty acids.

In another example, the present invention provides a method comprising:
(i) administering a compound to a genetically modified non-human animal deficient in prePYY or a derivative thereof; and
(ii) determining the level of triglycerides and/or free fatty acids of the animal, wherein reduced triglycerides and/or free fatty acids in the animal compared to an animal deficient in prePYY or a derivative thereof that has not been administered the compound indicates that the compound reduces triglycerides and/or free fatty acids.

Alternatively, the method comprises:
(i) administering a compound to a non-human animal expressing a functional PYY peptide; and
(ii) determining the level of triglycerides and/or free fatty acids in the animal, wherein a similar level of triglycerides and/or free fatty acids in the animal compared to the level of triglycerides and/or free fatty acids of a genetically modified non-human animal deficient in prePYY or a derivative thereof that has not been administered the compound indicates that the compound increases triglycerides and/or free fatty acids.

Such a method is useful for identifying a compound for the treatment of a disease or disorder associated with increased level of triglyceride or free fatty acid or for reducing the risk of developing such a disease or disorder. For example, increased levels of free fatty acids and/or triglycerides is associated with an increased risk of developing gall stones, heart attack, cardiac disease, coronary heart disease or stroke.

As used herein, the term "free fatty acid" shall be taken to mean a non-esterified fatty acid that may be detected, for example, in the serum of a subject. A "fatty acid" is a aliphatic monocarboxylic acid liberated from a naturally occurring fat or oil by hydrolysis. Generally, a fatty acid is an unbranched chain of 4 to 24 carbons.

A method for determining the level of free fatty acid in a knockout animal of the invention will be apparent to the skilled artisan, and may be determined using, for example a commercially available kit from Wako (Richmond, Va.).

As used herein, the term "triglyceride" shall be taken to mean an ester of glycerol and three fatty acids. The type of fatty acid can vary and will be influenced by the genotype of the animal as well as diet. Methods for determining a triglyceride level in a knockout animal of the invention will be apparent to the skilled artisan and include a standard lipid panel analysis or using a kit, for example, from Sigma Aldrich or Wako Chemicals.

The present invention additionally contemplates a method for determining a compound for the treatment of glucose intolerance.

In another example, the present invention provides a method comprising:
(i) administering a compound to a genetically modified non-human animal deficient in prePYY or a derivative thereof; and
(ii) determining the level of glucose tolerance and/or glucose clearance of the animal, wherein increased glucose tolerance and/or glucose clearance in the animal compared to an animal deficient in prePYY or a derivative thereof that has not been administered the compound indicates that the compound enhances glucose tolerance and/or glucose clearance.

As used herein, the term "glucose intolerance" shall be taken to mean that a subject is incapable of clearing glucose from their serum or has a reduced ability to clear glucose from their serum. Glucose intolerance is generally diagnosed or detected by detecting an increased level of glucose in the serum of a subject either at basal levels or following administration of a known level of glucose.

In a preferred embodiment of the invention, any of the screening processes described herein are performed using a genetically modified non-human animal deficient in prePYY or a derivative thereof that is fed or maintained on a high-fat diet. By "high fat diet" is meant that the food consumed by the animal has a higher percentage of fat than standard food fed to the animal. For example, at least 15% of the calories in feed used in a high fat diet is from fat, preferably, at least 30% of calories in feed used in a high fat diet is from fat, even more preferably, at least 40% to 50% of calories in feed used in a high fat diet is from fat and even more preferably, at least 60% of calories in feed used in a high fat diet is from fat. Suitable sources of feed for a high fat diet for a genetically modified animal of the invention will be apparent to the skilled artisan. For example, a high-fat feed comprises sunflower seeds or other forms of seeds.

Compounds identified in such screens for enhancing glucose tolerance are particularly useful e.g., in the treatment of complications of obesity, especially Type II diabetes.

Candidate Compounds for Screening and Therapy

Peptide Compounds

In one embodiment of the invention, a compound screened or assayed using the method of the invention is a peptidyl compound.

Such a peptidyl compound may be produced using any means known in the art. For example, a peptidyl compound is produced synthetically. Synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the de-protecting, neutralization, coupling and wash protocols of the original solid phase procedure of Merrifield, *J. Am. Chem. Soc.*, 85:2149-2154, 1963, or the base-labile Nα-amino protected 9-fluorenylmethoxycarbonyl (Fmoc) amino acids described by Carpino and Han, *J. Org. Chem.*, 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

Alternatively, a synthetic peptide is produced using a technique known in the art and described, for example, in Stewart and Young (In: Solid Phase Synthesis, Second Edition, Pierce Chemical Co., Rockford, Ill. (1984) and/or Fields and Noble (*Int. J. Pept. Protein Res.*, 35:161-214, 1990), or using an automated synthesizer. Accordingly, peptides of the invention may comprise D-amino acids, a combination of D- and L-amino acids, and various unnatural amino acids (e.g., (β-methyl amino acids, Cα-methyl amino acids, and Nα-methyl amino acids, etc) to convey special properties. Synthetic amino acids include ornithine for lysine, fluorophenylalanine for phenylalanine, and norleucine for leucine or isoleucine.

In another embodiment, a peptidyl agent is produced using recombinant means. For example, an oligonucleotide or other nucleic acid is placed in operable connection with a promoter. Methods for producing such expression constructs, introducing an expression construct into a cell and expressing and/or purifying the expressed peptide, polypeptide or protein are known in the art and described, for example, in Ausubel et al (In: Current Protocols in Molecular Biology. Wiley Interscience, ISBN 047 150338, 1987) or Sambrook et al (In: Molecular Cloning: Molecular Cloning: A Laboratory Manual, Cold Spring Harbor Laboratories, New York, Third Edition 2001).

The term "promoter" is to be taken in its broadest context and includes the transcriptional regulatory sequences of a genomic gene, including the TATA box or initiator element, which is required for accurate transcription initiation, with or without additional regulatory elements (i.e., upstream activating sequences, transcription factor binding sites, enhancers and silencers) which alter gene expression in response to developmental and/or external stimuli, or in a tissue specific manner. In the present context, the term "promoter" is also used to describe a recombinant, synthetic or fusion molecule, or derivative which confers, activates or enhances the expression of a nucleic acid molecule to which it is operably linked, and which encodes the peptide or protein. Preferred promoters can contain additional copies of one or more specific regulatory elements to further enhance expression and/or alter the spatial expression and/or temporal expression of said nucleic acid molecule.

Placing a nucleic acid molecule under the regulatory control of, i.e., "in operable connection with", a promoter sequence means positioning said molecule such that expression is controlled by the promoter sequence, generally by positioning the promoter 5' (upstream) of the peptide-encoding sequence.

Suitable promoters and/or vectors for expressing a peptide will be apparent to the skilled artisan. For example, a typical promoters suitable for expression in a mammalian cell, mammalian tissue or intact mammal include, for example a promoter selected from the group consisting of, a retroviral LTR element, a SV40 early promoter, a SV40 late promoter, a cytomegalovirus (CMV) promoter, a CMV IE (cytomegalovirus immediate early) promoter, an $EF_{1\alpha}$ promoter (from human elongation factor 1α), an EM7 promoter or an UbC promoter (from human ubiquitin C).

A vector comprising such a suitable promoter is often used in an expression vector. A suitable expression vector for expression in a mammalian cell will be apparent to the skilled person and includes, for example, the pcDNA vector suite supplied by Invitrogen, the pCI vector suite (Promega), the pCMV vector suite (Clontech), the pM vector (Clontech), the pSI vector (Promega) or the VP 16 vector (Clontech).

Typical promoters suitable for expression in viruses of bacterial cells and bacterial cells include, but are not limited to, the lacz promoter, the Ipp promoter, temperature-sensitive $\lambda_L$ or $\lambda_R$ promoters, T7 promoter, T3 promoter, SP6 promoter or semi-artificial promoters such as the IPTG-inducible tac promoter or lacUV5 promoter.

A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987) and (Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, such as for example, PKC30 (Shimatake and Rosenberg, *Nature* 292, 128, 1981); pKK173-3 (Amann and Brosius, *Gene* 40, 183, 1985), pET-3 (Studier and Moffat, *J. Mol. Biol.* 189, 113, 1986); the pCR vector suite (Invitrogen), pGEM-T Easy vectors (Promega), the pL expression vector suite (Invitrogen) the pBAD/TOPO (Invitrogen, Carlsbad, Calif.); the pFLEX series of expression vectors (Pfizer Inc., CT, USA); the pQE series of expression vectors (QIAGEN, CA, USA), or the pL series of expression vectors (Invitrogen), amongst others.

Methods for producing an expression construct will be apparent to the skilled artisan and/or described, for example, in Sambrook et al (In: Molecular cloning, A laboratory manual, second edition, Cold Spring Harbor Laboratory, Cold Spring Harbor, N.Y., 1989).

Following construction of a suitable expression construct, said construct is introduced into a cell using a method described herein, and the cell maintained for a time and under conditions sufficient for the expression of a peptide encoded by the nucleic acid. Optionally, the peptide is expressed as a fusion protein with a tag, e.g., a hexa-his tag or a myc tag to facilitate purification of the peptide, e.g., by affinity purification.

Alternatively, the peptide, polypeptide or protein is expressed using a cell free system, such as, for example, the TNT system available from Promega. Such an in vitro translation system is useful for screening a peptide library by, for example, ribosome display, covalent display or mRNA display.

A preferred source for a peptide useful for altering a phenotype of a genetically modified animal of the invention is, for example, from a PYY or from a related peptide, e.g., NPY or PP.

In another embodiment, a peptide library is screened to identify a compound that modulates a phenotype of a genetically modified organism of the invention. By "peptide library" is meant a plurality of peptides that may be related in sequence and/or structure or unrelated (e.g., random) in their structure and/or sequence. Suitable methods for production of such a library will be apparent to the skilled artisan and/or described herein.

For example, a random peptide library is produced by synthesizing random oligonucleotides of sufficient length to encode a peptide of desired length, e.g., 7 or 9 or 15 amino acids. Methods for the production of an oligonucleotide are known in the art. For example, an oligonucleotide is produced using standard solid-phase phosphoramidite chemistry. Essentially, this method uses protected nucleoside phosphoramidites to produce a short oligonucleotide (i.e., up to about 80 nucleotides). Typically, an initial 5'-protected nucleoside is attached to a polymer resin by its 3'-hydroxy group. The 5' hydroxyl group is then de-protected and the subsequent nucleoside-3'-phosphoramidite in the sequence is then coupled to the de-protected group. The internucleotide bond is then formed by oxidising the linked nucleosides to form a phosphotriester. By repeating the steps of de-protection, coupling and oxidation an oligonucleotide of desired length and sequence is obtained. Suitable methods of oligonucleotide synthesis are described, for example, in Caruthers, M. H., et al., "Methods in Enzymology," Vol. 154, pp. 287-314 (1988).

Each of the oligonucleotides is then inserted into an expression construct (in operable connection with a promoter) and introduced into a cell or animal of the invention. Suitable methods for producing a random peptide library are described, for example, in Oldenburg et al., *Proc. Natl. Acad. Sci. USA* 89:5393-5397, 1992; Valadon et al., *J. Mol. Biol.,* 261:11-22, 1996; Westerink *Proc. Natl. Acad. Sci. USA.,* 92:4021-4025, 1995; or Felici, *J. Mol. Biol.,* 222:301-310, 1991.

Optionally, the nucleic acid is positioned so as to produce a fusion protein, wherein the random peptide is conformationally constrained within a scaffold structure, eg., a thioredoxin (Trx) loop (Blum et al. *Proc. Natl. Acad. Sci. USA,* 97, 2241-2246, 2000) or a catalytically inactive staphylococcal nuclease (Norman et al, *Science,* 285, 591-595, 1999), to enhance their stability. Such conformational constraint within a structure has been shown, in some cases, to enhance the affinity of an interaction between a random peptides and its target.

To facilitate screening of a large number of peptides (i.e., to avoid producing a number of animals capable of expressing a peptide to be screened) a peptide may optionally be fused or conjugated to a protein transduction domain to facilitate its uptake into a cell of a transgenic mouse of the invention. A suitable protein transduction domain will be apparent to the skilled person and includes, for example, HIV-1 TAT or polyarginine. Protein transduction domains are reviewed, for example, in Deitz and Bahr, *Mol. Cell. Neurosci.* October; 27: 85-131, 2004.

Antibodies

The present invention additionally contemplates an antibody based compound, including an antibody or fragment thereof. Preferably, a library of antibody based compounds that are capable of being expressed in or entering a cell are screened to determine an antibody or a fragment thereof capable of modulating a phenotype of a genetically modified animal described herein.

By "antibody based compound" is meant an antibody or a fragment thereof, whether produce using standard or recombinant techniques. Accordingly, an antibody based compound includes, for example, an intact monoclonal or polyclonal antibody, an immunoglobulin (IgA, IgD, IgG, IgM, IgE) fraction, a humanized antibody, or a recombinant single chain antibody, as well as a fragment of an antibody, such as, for example Fab, F(ab)2, and Fv fragments.

A suitable antibody for altering a phenotype of the genetically modified animal of the invention is, for example, directed against a receptor to which PYY binds. For example, mature PYY binds with high affinity to Y-Y1 receptor and PYY[3-36] binds with high affinity to Y-Y2 receptor. Accordingly, an antibody capable of binding to the PYY binding site of such a receptor (and preferably activating the receptor) may be useful for modulating a phenotype of an animal of the invention.

Such an antibody, preferably a monoclonal antibody, is produced by immunizing an animal (e.g., a mouse) with the relevant immunogen. Optionally, the immunogen is injected in the presence of an adjuvant, such as, for example Freund's complete or incomplete adjuvant, lysolecithin and/or dinitrophenol to enhance the immune response to the immunogen. The immunogen may also be linked to a carrier protein, such as, for example, BSA. Spleen cells are then obtained from the immunized animal. The spleen cells are then immortalized by, for example, fusion with a myeloma cell fusion partner, preferably one that is syngenic with the immunized animal. A variety of fusion techniques may be employed, for example, the spleen cells and myeloma cells may be combined with a nonionic detergent or electrofused and then grown in a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and growth media in which the cells have been grown is tested for the presence of binding activity against the polypeptide (immunogen). Hybridomas having high reactivity and specificity are preferred.

Monoclonal antibodies are isolated from the supernatants of growing hybridoma colonies using methods such as, for example, affinity purification using the immunogen used to immunize the animal to isolate an antibody capable of binding thereto. In addition, various techniques may be employed to enhance the yield, such as injection of the hybridoma cell line into the peritoneal cavity of a suitable vertebrate host, such as a mouse. Monoclonal antibodies are then harvested from the ascites fluid or the blood of such an animal subject. Contaminants are removed from the antibodies by conventional techniques, such as chromatography, gel filtration, precipitation, and/or extraction.

Alternatively, an antibody library and preferably a library of antibodies that are expressed within a cell is used for the screening method of the invention. Such an antibody, also known as an intrabody, is essentially as recombinant ScFv antibody fragment. Essentially, an ScFv antibody fragment is a recombinant single chain molecule containing the variable region of a light chain of an antibody and the variable region of a heavy chain of an antibody, linked by a suitable, flexible polypeptide linker.

A library of ScFv fragments is produced, for example, by amplifying a variable region of a large and/or small chain from nucleic acid amplified from spleen cells that are derived from a subject (e.g., a mouse) that optionally, has been previously immunized with an immunogen of interest. These regions are cloned into a vector encoding a suitable framework including a linker region to facilitate expression of an intrabody that is stable when expressed in a cell (for example, see Worn et al., *J. Biol. Chem.*, 275: 2795-803, 2003). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., *Mol. Cell. Biol.* 15:1182-91, 1995; Lefler et al., *Eur. J. Biochem.* 267: 1196-205 2000).

Nucleic Acids

A nucleic acid aptamer (adaptable oligomer) is a nucleic acid molecule that is capable of forming a secondary and/or tertiary structure that provides the ability to bind to a molecular target. Suitable methods for producing and/or screening an aptamer library is described, for example, in Elloington and Szostak, *Nature* 346:818-22, 1990.

Generally, an aptamer is identified from a library of nucleic acids that comprise at least a random region are screened. For example, the library is screened to identify an aptamer that is capable of modifying a biological activity of a knockout animal of the invention.

An aptamer usually comprises at least one random region of nucleic acid, often flanked by a known sequence that may provide the annealing site for hybridization of a PCR primer for later amplification of the aptamer and/or may provide for conformational constraint, e.g., by forming a hairpin. The random sequence portion of the oligonucleotide can be of any length (however, is generally 30 to 50 nucleotides in length) and can comprise ribonucleotides and/or deoxyribonucleotides and can include modified or non-natural nucleotides or nucleotide analogs. Random oligonucleotides can be synthesized from phosphodiester-linked nucleotides using solid phase oligonucleotide synthesis techniques well known in the art and/or described herein. Typical syntheses carried out on automated DNA synthesis equipment yield $10^{15}$-$10^{17}$ molecules.

Due to the large number of aptamers that may be screened, a screening assay described herein may be performed using arrays of aptamers, and those arrays capable of modifying a phenotype of the knockout of the invention rescreened to determine the specific aptamer of interest.

Alternatively, a library of aptamers is screened to identify an aptamer that is capable of binding to, for example, a receptor of PYY. For example, mature PYY binds with high affinity to the Y-Y1 receptor, while PYY[3-36] binds with higher affinity to the Y-Y2 receptor. An identified aptamer may then be administered to an animal of the invention to determine if it is capable of modulating a phenotype of said animal.

Small Molecules

The structure of small molecules varies considerably as do methods for their synthesis. The present invention contemplates the screening of any small molecule or small molecule library to identify a compound capable of modulating the phenotype of an animal of the invention.

An example of a suitable small molecule library is described, for example, in U.S. Pat. No. 6,168,192. The method described is for producing a multidimensional chemical library that comprises converting a set of at least two different α-allyl carbonyl monomers to form monomer derivatives by converting the allyl group to another group and covalently linking at least two of the produced monomers to form oligomers.

In an alternative method, McMillan et al., (*Proc Natl Acad Sci USA*. 97: 1506-1511, 2000) describes the production of an encoded chemical library (ECLiPS method) based on a pyrimidineimidazole core prepared on polyethylene glycol-grafted polystyrene support. Compounds are attached to resin by a photolabile o-nitrobenzyl amide linker. The first synthetic step introduced primary amines. After a pool and split step, the amines are acylated with fluorenylmethoxycarbonyl (Fmoc)-protected amino acids. A second pool and split step is performed, followed by Fmoc deprotection and subsequent heteroarylation of the resulting free amines by electrophilic substitution with a set of nine substituted pyrimidines. The library produced comprised 8,649 compounds.

Additional small molecule libraries include, for example, libraries comprising statine esters (U.S. Pat. No. 6,255,120), moeomycin analogs (U.S. Pat. No. 6,207,820), fused 2,4-pyrimidinediones (U.S. Pat. No. 6,025,371), dihydrobenzopyran based molecules (U.S. Pat. No. 6,017,768), 1,4-benzodiazepin-2,5-dione based compounds (U.S. Pat. No. 5,962,337), benmzofuran derivatives (U.S. Pat. No. 5,919,955), indole derivatives (U.S. Pat. No. 5,856,496), products of polyketides (U.S. Pat. No. 5,712,146), morpholino compounds (U.S. Pat. No. 5,698,685) or sulphonamide compounds (U.S. Pat. No. 5,618,825).

Compounds screened using the animal of the present invention of the present invention can be screened using high throughput screening techniques, such as, for example, sequential high throughput screening (SHTS). SHTS is an iterative process of screening a sample of compounds for activity, analysing the results, and selecting a new set of compounds for screening, based on compounds identified in one or more previous screens. Selection of compounds is driven by finding structure activity relationships (SARs) within the screened compounds and using those relationships to drive further selection.

Recursive partitioning (RP) is a statistical methodology that can be used in conjunction with high-throughput screening techniques, such as, SHTS, by identifying relationships between specific chemical structural features of the molecules and biological activity. The premise of this method is that the biological activity of a compound is a consequence of its molecular structure. Accordingly, it is useful to identify those aspects of molecular structure that are relevant to a particular biological activity. By gaining a better understanding of the mechanism by which the compound acts, additional compounds for screening can more accurately be selected. Suitable R P methods are described, for example in Hawkins, D. M. and Kass, G. V., (In: Automatic Interaction Detection. In Topics in Applied Multivariate Analysis; Hawkins, D. H., Ed.; 1982, Cambridge University Press, pp. 269-302).

Quantitative structure activity relationship (QSAR) is also useful for determining a feature or features of a compound required for or useful for a desired biological activity. QSAR models are determined using sets of compounds whose molecular structure and biological activity are known, a training set. QSAR approaches are either linear or nonlinear. The linear approach assumes that the activity varies linearly with the level of whatever features affect it, and that there are no interactions among the different features.

Nonlinear QSAR approaches account for the fact that activity can result from threshold effects; a feature must be present for at least some threshold level for activity to occur. Furthermore, as interactions between features are observed in many QSAR settings, the utility of one feature depends upon the presence of another. For example, activity may require the simultaneous presence of two features.

Production of Therapeutic Compounds

In one embodiment, the present invention provides a process for providing a therapeutic compound, for example, for the treatment of obesity or glucose intolerance, said process comprising:
(i) identifying a compound using a method described herein;
(ii) optionally, determining the structure of the compound; and
(iii) providing the compound or the name or structure of the compound.

Naturally, for compounds that are known albeit not previously tested for their function using a screen provided by the present invention, determination of the structure of the compound is implicit in step (i) supra. This is because the skilled artisan will be aware of the name and/or structure of the compound at the time of performing the screen.

As used herein, the term "providing the compound" shall be taken to include any chemical or recombinant synthetic means for producing said compound or alternatively, the provision of an agent that has been previously synthesized by any person or means. Suitable methods for producing a compound are described herein or known in the art.

In a preferred embodiment, the compound or modulator or the name or structure of the compound or modulator is provided with an indication as to its use e.g., as determined by a screen described herein.

In another embodiment, the invention provides a process for providing a therapeutic compound, for example, for the treatment of obesity or glucose intolerance, said process comprising:
(i) identifying a compound using a method described herein;
(ii) optionally, determining the structure of the compound; compound; and
(iii) providing, the compound.

Optionally, the candidate agent is provided with an indication as to its use, for example, as determined using a method described herein.

The present invention additionally contemplates a process for manufacturing a medicament for the treatment of obesity, glucose intolerance, increased level of triglycerides and/or increased level of free fatty acids comprising:
(i) identifying a compound using a method described herein
(ii) optionally, isolating the compound;
(iii) optionally, providing the name or structure of the compound;
(iv) optionally, providing the compound; and
(v) using the compound in the manufacture of a medicament for the treatment of insulin resistance.

For example, the compound is formulated into a pharmaceutical formulation. Formulation of a pharmaceutical compound will vary according to the route of administration selected (e.g., solution, emulsion, capsule). An appropriate composition comprising the identified compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the compound can be solubilized and loaded into a suitable dispenser for administration (e.g., an atomizer, nebulizer or pressurized aerosol dispenser).

Furthermore, where the compound is a protein or peptide or antibody or fragment thereof, the compound can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

The pH and exact concentration of the various components the formulation suitable for administration to the animal are adjusted according to routine skills in the art.

Anti-PYY Monoclonal Antibodies

A knockout animal of the invention is preferably, albeit not necessarily, used for producing an antibody against or capable of specifically binding to a PYY polypeptide. The use of the PYY-deficient animals is preferred because there is a high degree of PYY amino acid sequence conservation in animals, which is likely to prevent antibody production in an animal that expresses PYY due to self-tolerance. Such recognition of a "self" epitope has been previously shown to result in deletion of self-reactive B-cells (Goodnow et al., Nature, 334:676-682, 1988). As the homozygous knockout animals of the invention have not ever expressed PYY, an antibody capable of selectively binding to this protein is unlikely to recognize or cross-react with a self-protein.

As used herein the term "antibody" refers to intact monoclonal or polyclonal antibodies, immunoglobulin (IgA, IgD, IgG, IgM, IgE) fractions, humanized antibodies, or recombinant single chain antibodies, as well as fragments thereof, such as, for example Fab, F(ab)2, and Fv fragments.

In one embodiment, the method of the invention is used to produce a polyclonal antibody or polyclonal antisera. Such a method involves, for example, immunizing a wild-type animal or a PYY-deficient animal of the invention with a PYY or an epitope thereof. The PYY or epitope is optionally joined to a carrier protein, such as bovine serum albumin or keyhole limpet hemocyanin. The immunogen and optionally a carrier for the protein is injected into the animal host, preferably according to a predetermined schedule incorporating one or more booster immunizations, and blood collected from said the animals periodically. Optionally, the immunogen is injected in the presence of an adjuvant, such as, for example Freund's complete or incomplete adjuvant, lysolecithin and/or dinitrophenol to enhance the immune response to the immunogen. Polyclonal antibodies specific for the PYY are then be purified from the blood isolated from an animal by, for example, affinity chromatography using the PYY or the epitope used to immunize the animal coupled to a suitable solid support.

Preferably, the method of the invention is used to produce a monoclonal antibody. To facilitate production of such an antibody, the method of the present invention preferably uses a genetically modified mouse. In accordance with this embodiment, the method of the invention comprises:

(i) immunizing a PYY knockout mouse of the invention with a PYY or an epitope thereof;
(ii) isolating a hybridoma from the immunized mouse; and
(ii) purifying antiserum or an antibody that binds to PYY from the isolated hybridoma.

Methods for producing a monoclonal antibody are known in the art and/or described herein-above and are to be taken to apply mutatis mutandis to the present embodiment of the invention.

Alternative methods for producing polyclonal or monoclonal antibodies are known in the art and include, for example, a human B-cell hybridoma technique (Kozbar et al., *Immunol. Today* 4:72, 1983), a EBV-hybridoma technique to produce human monoclonal antibodies (Cole et al. *Monoclonal Antibodies in Cancer Therapy,* 1985 Allen R. Bliss, Inc., pages 77-96), or screening of combinatorial antibody libraries (Huse et al., *Science* 246:1275, 1989). Alternative techniques are described, for example in, Harlow and Lane (In: Antibodies: A Laboratory Manual, Cold Spring Harbor Laboratory, 1988).

As discussed supra antibody fragments are contemplated by the present invention. The term "antibody fragment" refers to a portion of a full-length antibody, generally the antigen binding or variable region. Examples of antibody fragments include Fab, Fab', F(ab')$_2$ and Fv fragments.

Papain digestion of an antibody produces two identical antigen binding fragments, called the Fab fragment, each with a single antigen binding site, and a residual "Fc" fragment.

Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

An "Fv" fragment is the minimum antibody fragment that contains a complete antigen recognition and binding site. This region consists of a dimer of one heavy and one light chain variable domain in a non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding, specificity to the antibody. However, even a single variable domain (or half of an Fv comprising only three CDRs specific for an antigen) has the ability to recognize and bind antigen.

A Fab fragment [also designated as F(ab)] also contains the constant domain of the light chain and the first constant domain ($CH_1$) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art.

"Single-chain Fv" or "scFv" antibody fragments comprise the VH and VL domains of an antibody, wherein these domains are present in a single polypeptide chain. Generally, the Fv polypeptide further comprises a polypeptide linker between the VH and VL domains which enables the scFv to form the desired structure for antigen binding. For a review of scFv, see Pluckthun in The Pharmacology of Monoclonal Antibodies, vol. 113, Rosenburg and Moore eds. Springer-Verlag, New York, pp. 269-315 (1994).

Chimeric and/or humanized antibodies have the same or similar binding specificity and affinity as a mouse or other nonhuman antibody that provides the starting material for construction of a chimeric or humanized antibody.

The present invention additionally contemplates a chimeric antibody. A chimeric antibody comprises light and heavy chain genes that have been constructed, typically by genetic engineering, from immunoglobulin gene segments belonging to different species. For example, the variable (V) segments of the genes are from a mouse monoclonal antibody may be joined or fused to nucleic acid encoding human constant (C) segments, such as IgG1 or IgG4. A typical chimeric antibody is thus a hybrid protein consisting of the V or antigen-binding domain from a mouse antibody and the C or effector domain from a human antibody.

Furthermore, the present invention contemplates a humanized antibody. A humanized antibody comprises variable region framework residues substantially from, for example, a human antibody (termed an acceptor antibody) and complementarity determining regions substantially from, for example, a mouse-antibody, (referred to as the donor immunoglobulin). Suitable methods for producing a humanized antibody are described, for example, in Queen et al., *Proc. Natl. Acad. Sci. USA* 86:10029-10033, 1989; U.S. Pat. No. 5,693,762, U.S. Pat. No. 5,693,761 and U.S. Pat. No. 5,225,539. A constant region(s), if present, are also substantially or entirely from a human immunoglobulin. The human variable domains are usually chosen from human antibodies whose framework sequences exhibit a high degree of sequence identity with a murine variable region domain from which the CDR/s were derived. The heavy and light chain variable region framework residues can be derived from the same or different human antibody sequences. The human antibody sequences can be the sequences of naturally occurring human antibodies or can be consensus sequences of several human antibodies (e.g., as described in WO 92/22653).

While an antibody or fragment thereof may be produced using an entire PYY it may also be desirable to produce an antibody using a specific epitope of PYY, e.g., an immunogenic epitope.

For example, an immunogenic epitope is determined using the method described by Hopp, *Peptide Research,* 6: 183-190 1993, wherein a hydrophilic peptide is selected as it is more likely to occur at the surface of the native protein. However, a peptide should not be too highly charged, as this may reduce the efficiency of antibody generation.

Alternatively, an immunogenic epitope is determined using the method described by Palfreyman et al *J Immunol. Meth.* 75, 383-393, 1984, wherein the amino- and/or carboxy-terminal amino acids are used to generate a peptide against which specific antibodies are raised.

An immunogenic epitope may also be predicted using an algorithm such as for example that described in Kolaskar and Tongaonkar *FEBS Lett.* 276(1-2) 172-174, 1990. Such methods are based upon determining the hydrophilicity of regions of a protein, usually 6 amino acids, and determining those hydrophilic regions that are associated with turns in proteins, surface flexibility, or secondary structures, and are unlikely to be modified at the post-translational level, such as, for example by glycosylation. Such regions of a protein are therefore likely to be exposed, that is, at the surface of the three-dimensional structure of the protein. Furthermore, as these regions are not modified, they are likely to remain constant and as such offer a likely site of antibody recognition.

In yet another embodiment, overlapping peptides spanning the entire PYY protein, or a region of said protein are generated by synthetic means, using techniques known in the art.

In another embodiment, an antibody is produced against a specific region of a PYY. For example, an antibody is produced that is capable of detecting mature PYY (i.e., PYY[1-36]) and not PYY[3-36]. Accordingly, such an antibody is raised against a peptide comprising at least the first three amino acids of mature PYY, for example the first three amino acids of PYY set forth in SEQ ID NO: 10.

In one embodiment, the method of the invention additionally comprises providing or producing the knockout animal or knockout mouse. Suitable methods for producing such a knockout animal or knockout mouse are known in the art and/or described herein.

The present invention additionally contemplates an antibody produced by this method. In particular, the present invention contemplates a monoclonal antibody and, more preferable, a mouse monoclonal antibody produced by the method of the invention.

The present invention is described further in the following non-limiting examples and the accompanying examples:

Microorganism Deposits

A mouse hybridoma cell line designated 7K11-G3 producing a monoclonal antibody that binds specifically to PYY[1-36] has been deposited on Feb. 28, 2006 under the provisions of the Budapest treaty on the International Recognition of the Deposit of Microorganisms for the Purposes of Patent Procedure with the European Collection of Cell Cultures (ECACC) and assigned ATCC Accession No. 06022101.

A mouse hybridoma cell line designated 3L16-N14 producing a monoclonal antibody that binds specifically to PYY[3-36] has also been deposited on. Feb. 28, 2006 under the provisions of the Budapest treaty on the International Recognition of the Deposit of Microorganisms for the Purposes of Patent Procedure with the European Collection of Cell Cultures (ECACC) and assigned ATCC Accession No. 06022102.

These deposits are not to be taken as an admission that any deposit is required for the purposes of sufficiently describing an invention claimed in this application or any continuation, divisional or reissue thereof, or for the purposes of satisfying the requirements of 35 U.S.C. §112.

The assignee of the present application hereby undertakes to make the deposited microorganisms available publicly at all times during the period from the date of publication of a non-provisional application filed in any Convention country in respect of the antibodies to the date on which a patent expires. Such availability may be made subject to a requirement for the deposited microorganism to be provided only to a skilled artisan nominated by the applicant or its assignee in the period prior to issuance of Letters Patent.

The assignee of the present application has agreed further to promptly replace the deposited microorganisms with a viable specimen of the same culture following issuance of a notice that an original deposit has ceased to be viable.

Availability of a deposited strain is not to be construed as a license to practice the invention in contravention of the rights granted under the authority of any government in accordance with its patent laws.

Antigen-Based Methods for Determining PYY Levels

The present invention provides antibody reagents and kits for the determination of PYY levels in patient samples e.g., serum or a fraction thereof, and/or for use in the field of pharmacology to assess the effect(s) of a therapeutic compound on PYY expression or activity.

Antibodies and antibody fragments disclosed herein can be used as experimental research tools, or for diagnostic/screening purposes in a field setting or to detect the presence or absence or to quantify PYY in patient samples.

Suitable samples for performing such assays include any biological fluids that are known to comprise PYY e.g., blood serum or cerebrospinal fluid or a fraction of blood serum comprising PYY or a fraction of cerebrospinal fluid comprising PYY. In some embodiments, an antibody is used to detect the presence of PYY in a sample comprising e.g., blood serum or cerebrospinal fluid, a tissue extract, freshly harvested cells, or lysates of cells which have been incubated in cell culture.

The sample is contacted with an amount of monoclonal antibody, and the samples are screened to detect a monoclonal antibody complexed with PYY antigen, such as detecting the binding reaction between the antibody and the antigen. Detection of an antibody-antigen complex or binding reaction indicates that the sample comprises the appropriate PYY peptide e.g., PYY[1-36] or PYY[3-36].

In interpreting the data obtained from such assays, a high level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of obesity or low propensity for developing one or more complications associated with obesity as described herein. Conversely, a low level of PYY[3-36] determined in such assays e.g., in relation to an amount of PYY[1-36] or PYY[total] in the sample, and preferably expressed as an absolute amount compared to the level in an equivalent sample from a normal or healthy subject, is indicative of a high risk of obesity or high propensity for developing one or more complications associated with obesity as described herein. In view of the role of PYY[3-36] as a major presynaptic ligand for Y-Y2 receptors (Baldock et al., *J. Clin. Invest.*, 109, 915-921, 2002) it is likely that PYY[3-36] is the major ligand affecting bone remodelling, e.g., as determined by measuring bone mineral density and bone mineral content. Accordingly, in the assays described herein, low levels of PYY[3-36] e.g., in relation to an amount of PYY[1-36] or PYY[total] in the sample, and preferably expressed as an absolute amount compared to the level in an equivalent sample from a normal or healthy subject, is indicative of a low risk of developing a bone disease or bone disorder as described herein. Similarly, a low level of PYY[total] determined in such assays, preferably expressed as an absolute amount compared to the level in an equivalent sample from a normal or healthy subject, is indicative of a high risk of obesity or high propensity for developing one or more complications associated with obesity as described herein. A low level of PYY[total] determined in such assays, preferably expressed as an absolute amount compared to the level in an equivalent sample from a normal or healthy subject, is also indicative of a low risk of developing a bone disease or disorder associated with deficient bone remodeling activity as described herein. As used herein, the term "PYY[total]" shall be taken to mean the sum of amounts of PYY[1-36] and PYY[3-36] in a sample.

In some embodiments, the antibody is labelled with a reporter molecule. In other embodiments, antigen in the sample is immobilized on a surface prior to introduction of the labelled antibody, and the amount of the signal, corresponding to the amount of bound labelled antibody, correlates to the amount of antigen in the sample. In still other embodiments, antigen is captured by immobilized unlabeled first antibody, after which a labelled second antibody is introduced to bind to the captured antigen and produce a signal in proportion to the amount of captured antigen.

Immunoassays are preferably performed using a solid support or solid phase carriers, on which antigen or antibody is immobilized. Any number of different carriers may be employed without undue experimentation. Examples of well-known carriers include hydrogel, glass, polystyrene, polypropylene, polyethylene, dextran, nylon, amylase, amylose, natural and modified cellulose, polyacrylamide, agarose and magnetite. The nature of the carrier can be either soluble or insoluble for purposes of the invention.

Preferred means for quantifying immune assays include radiolabel, enzyme, fluorescence, precipitation, agglutination, coagulation, Western blot, grid blot, tissue blot, dot blot, chemiluminescence, light-scattering, electrochemical, dipstick, or biosensor assays. Such methods are described e.g., in Principles aid Practice of Immunoassays, Price and Newman eds., Stockton Press, 1997; The Immunoassay Handbook, 2nd Edition, Wild Ed., Nature Publishing Group, London, 2001.

In general, the antibody is used as a labelled primary reagent in a direct assay or as an unlabelled reagent to be detected by a secondary developing antibody conjugate, such as labelled anti-mouse antibody, in an indirect assay.

Alternatively, the antibody on the surface of a B cell is used in an assay and the presence of the B cell detected.

The immunoassay formats encompassed by the invention may be non-competitive (i.e., wherein the antibody and antigen interact in the absence of a competing binding partner for said antibody or said antigen), or alternatively, competitive (i.e., wherein the antibody and antigen interact in the presence of a competing binding partner for said antibody or said antigen). Competitive immunoassay formats are generally preferred for qualitative or quantitative determination of PYY or a homologue or ortholog thereof in a test sample relative to a standard or reference sample. This is useful, for example, when screening samples to determine the presence or absence of PYY, or a particular level of PYY.

A preferred competitive immunoassay for assaying PYY [1-36] comprises:
(i) combining a test sample with a known amount of labelled PYY[1-36];
(ii) contacting the combined test sample and labelled PYY with an antibody that binds specifically to PYY[1-36] for a time and under conditions sufficient for an antigen-antibody complex to form; and
(iii) detecting the amount of label in a complex formed, wherein the amount of label in the complex formed is inversely proportional to the amount of PYY[1-36] in the test sample.

In interpreting the data obtained from this assay format, a high level of label in the complex formed at (iii) indicates a low level of PYY[1-36] in the test sample. It will be apparent from the preceding discussion, that, when coupled to an assay for determining PYY[3-36] will provide information on the risk of a subject becoming obese, developing complications associated with obesity or developing a bone disease or disorder.

Alternatively, a preferred competitive immunoassay for PYY[3-36] comprises:
(i) combining a test sample with a known amount of labelled PYY[3-36];
(ii) contacting the combined test sample and labelled PYY with an antibody that binds specifically to PYY[3-36] for a time and under conditions sufficient for an antigen-antibody complex to form; and
(iii) detecting the amount of label in a complex formed, wherein the amount of label in the complex formed is inversely proportional to the amount of PYY[3-36] in the test sample.

It will be apparent from the preceding description that a low amount of label in the complex formed is indicative of a high level of PYY[3-36] e.g., in relation to an amount of PYY[1-36] or PYY[total] in the test sample and preferably expressed relative to an amount of PYY[3-36] in a healthy or normal subject. When the amount of PYY[3-36] is preferably expressed as an absolute amount compared to the level in an equivalent sample from a normal or healthy subject, a high level of PYY[3-36] is indicative of a low risk of obesity or low propensity for developing one or more complications associated with obesity as described herein. Conversely, a low level of PYY[3-36] determined in such assays e.g., in relation to an amount of PYY[1-36] or PYY[total] in the sample, and preferably expressed as an absolute amount compared to the level in an equivalent sample from a normal or healthy subject, is indicative of a high risk of obesity or high propensity for developing one or more complications associated with obesity as described herein. A low level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of developing a bone disease or bone disorder as described herein.

The immunoassays described herein may be modified as a two-site immunoassay and/or sandwich immunoassay, wherein multiple antibodies that bind to different epitopes on PYY are employed. For example, a "capture" or "immunocapture" antibody that binds to PYY generally may be used to purify or separate the PYY isoenzymes from a complex sample prior to detection of PYY as described herein with reference to any embodiment. For example, the antigen in a sample extract can be captured by an unlabelled antibody immobilized on the surface of an ELISA well and then detected by a labelled antibody of the same or different kind and/or specificity.

For example, a preferred competitive immunoassay for determining the amounts of both PYY[1-36] and PYY[3-36] in the same sample comprises:
(i) combining a test sample with a known amount of PYY[1-36] detectably labelled with a first reporter molecule and a known amount of PYY[3-36] detectably labelled with a second reporter molecule that is different to the first reporter molecule;
(ii) contacting the combined test sample and labelled PYY with an antibody that binds specifically to PYY[1-36] and an antibody that binds specifically to PYY[3-36] for a time and under conditions sufficient for antigen-antibody complexes to form;
(iii) detecting the amount of first and second reporter molecules in the complexes formed, wherein the amount of first reporter molecule in the complex fanned is inversely proportional to the amount of PYY[1-36] in the test sample and the amount of second reporter molecule in the complex formed is inversely proportional to the amount of PYY[3-36] in the test sample; and
(iv) optionally, determining a relative amounts of first and second reporter molecules in the complexes, and/or determining a ratio of an amount of first reporter molecule to an amount of second reporter molecule, and/or determining a ratio of an amount of second reporter molecule to an amount of first reporter molecule.

In this assay format, the amounts of both PYY[1-36] and PYY[3-36] are determined simultaneously, preferably in the same reaction vessel. This permits the determination of PYY [total] values. Accordingly, in interpreting the data obtained from such assays, a high level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of obesity or low propensity for developing one or more complications associated with obesity as described herein. Conversely, a low level of PYY[3-36] determined in such assays e.g., in relation to an amount of PYY[1-36] or PYY[total] in the sample, and preferably expressed as an absolute amount compared to the level in an equivalent sample from a normal or healthy subject, is indicative of a high risk of obesity or high propensity for developing one or more complications associated with obesity as described herein. A low level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of developing a bone disease or bone disorder as described herein. Similarly, a low level of PYY[total] determined in such assays, preferably expressed as an absolute amount compared to the level in an equivalent sample from a normal or healthy subject, is indicative of a high risk of obesity or high propensity for developing one or more complications associated with obesity as described herein. A low level of PYY[total] determined in such assays, preferably expressed as an absolute amount compared to the level in an equivalent sample from a normal or healthy subject, is also indicative of a low risk of developing a bone disease or disorder associated with deficient bone remodeling activity as described herein. As used herein, the term "PYY [total]" shall be taken to mean the sum of amounts of PYY [1-36] and PYY[3-36] in a sample.

In a preferred form, the immunoassay is a non-competitive two site assay, in which the antibody is labelled directly, as opposed to the competitive immunoassay format employing a labelled PYY to compete for binding of endogenous PYY in the test sample. For example, the present invention provides a method comprising:
(i) contacting a test sample such as serum with an antibody that binds to PYY for a time and under conditions sufficient to form an antibody-antigen complex, wherein said antibody does not bind at higher affinity to PYY[1-36] or PYY[3-36];
(ii) contacting the complex formed with an antibody that binds at higher affinity to PYY[1-36] than to PYY[3-36] as described according to any embodiment herein for a time and under conditions sufficient for an antigen-antibody complex to form; and
(iii) detecting the complex, wherein the presence of detectable complex indicates the presence of said PYY[1-36].

As used herein, the term "antibody that binds to PYY" or "antibody does not bind at higher affinity to PYY[1-36] or PYY[3-36]" indicates that the antibody binds to both PYY [1-36] and PYY[3-36] e.g., at approximately equal affinity.

This assay format is particularly useful in conjunction with an assay as described herein or known in the art for determining the level of PYY[3-36] in a test sample. In conjunction with assays for determining the level of PYY[3-36] in a sample, this assay format provides baseline PYY[1-36] levels for determining or estimating PYY[total] values, or for a low or high risk of a subject becoming obese having a low or high propensity for developing one or more complications associated with obesity as described herein.

In yet another example, the present invention also provides a method comprising:
(i) contacting a test sample with an antibody that binds to PYY for a time and under conditions sufficient to form an antibody-antigen complex, wherein said antibody does not bind at higher affinity to PYY[1-36] or PYY[3-36];
(ii) contacting the complex formed with an antibody that binds at higher affinity to PYY[3-36] than to PYY[1-36] as described according to any embodiment herein for a time and under conditions sufficient for an antigen-antibody complex to form; and
(iii) detecting the complex, wherein the presence of detectable complex indicates the presence of said PYY[3-36].

In this assay format, a high level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of obesity or low propensity for developing one or more complications associated with obesity as described herein. Conversely, a low level of PYY[3-36] determined in such assays e.g., in relation to an amount of PYY[1-36] or PYY[total] in the sample, and preferably expressed as an absolute amount compared to the level in an equivalent sample from a normal or healthy subject, is indicative of a high risk of obesity or high propensity for developing one or more complications associated with obesity as described herein. A low level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of developing a bone disease or bone disorder as described herein.

Preferably, the present invention also provides a method comprising:
(i) contacting a test sample with an antibody that binds to PYY for a time and under conditions sufficient to form an antibody-antigen complex, wherein said antibody does not bind at higher affinity to PYY[1-36] or PYY[3-36];
(ii) contacting the complex formed at (i) with an antibody that binds at higher affinity to PYY[1-36] than to PYY[3-36] as described according to any embodiment herein for a time and under conditions sufficient for an antigen-antibody complex to form;
(iii) contacting the complex formed at (i) with an antibody that binds at higher affinity to PYY[3-36] than to PYY[1-36] as described according to any embodiment herein for a time and under conditions sufficient for an antigen-antibody complex to form;
(iv) detecting the complexes formed at (ii) and (iii); and
(v) optionally, determining an amount of complex formed at (ii) and/or (iii), and/or determining a relative amounts of complex formed at (ii) and (iii), and/or determining a ratio of an amount of complex formed at (ii) to an amount of complex formed at (iii), and/or determining a ratio of an amount of complex formed at (iii) to an amount of complex formed at (ii).

Alternatively, the test sample can be suspended in a buffer and mixed directly with an antibody, thus allowing the antibody to form an immune complex with its antigen. The reduction of free antibody due to complex formation can then be determined in a second step, based on solid-phase ELISA with purified antigen, by comparing the relative reactivity of free residual antibody left over after sample incubation (sample reactivity) to that of the same antibody when not mixed with the sample (reference reactivity). The ratio of sample to reference antibody reactivity will be inversely proportional to the amount of antigen in the sample.

In interpreting the data obtained from such assays, a high level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of obesity or low propensity for developing one or more complications associated with obesity as described herein. Conversely, a low level of PYY[3-36] determined in such assays e.g., in relation to an amount of PYY[1-36] or PYY [total] in the sample, and preferably expressed as an absolute amount compared to the level in an equivalent sample from a normal or healthy subject, is indicative of a high risk of obesity or high propensity for developing one or more complications associated with obesity as described herein. A low level of PYY[3-36] e.g., in relation to an amount of PYY[1-36] or PYY[total] in the sample, and preferably expressed as an absolute amount compared to the level in an equivalent sample from a normal or healthy subject, is indicative of a low risk of developing a bone disease or bone disorder as described herein. Similarly, a low level of PYY[total] determined in such assays, preferably expressed as an absolute amount compared to the level in an equivalent sample from a normal or healthy subject, is indicative of a high risk of obesity or high propensity for developing one or more complications associated with obesity as described herein. A low level of PYY[total] determined in such assays, preferably expressed as an absolute amount compared to the level in an equivalent sample from a normal or healthy subject, is also indicative of a low risk of developing a bone disease or disorder associated with deficient bone remodeling activity as described herein. As used herein, the term "PYY[total]" shall be taken to mean the sum of amounts of PYY[1-36] and PYY[3-36] in a sample.

In these immunocapture embodiments, it is well within the scope of the present invention to label both antibodies (i.e., the antibody that binds to PYY generally and the antibody that binds to PYY). In such embodiments, the ratio of bound anti-PYY[1-36] antibody to bound anti-PYY[3-36] antibody may be determined. The summation of the amounts of bound anti-PYY[1-36] antibody and bound anti-PYY[3-36] antibody are indicative of the relevant amount of PYY or homologue or derivative thereof in a sample.

In the preceding immunoassays, the detection of an immune complex formed between the antibodies of the present invention and a PYY peptide is accomplished any one of several techniques known in the art. For example, the assays may employ labelled or unlabelled reagents, including a secondary antibody capable of binding specifically to an antibody of the invention (i.e., that is capable of binding to PYY or a homologue or ortholog thereof, e.g., an anti-(mouse IgG) antibody). For example, the secondary antibody may be labelled with a suitable reporter molecule. Standard methods of labelling proteins are used to label the PYY protein or an antibody.

Suitable reporter molecules for labelling PYY or the antibody of the present invention or a secondary antibody include any one or more of a number of reporter molecules known in the art, for example, a radioisotope (e.g., $^3$H, $^{125}$I, $^{131}$I, $^{32}$P, or 8-azidoadenosine 5'-[α-$^{32}$P]triphosphate), an enzyme (e.g., horseradish peroxidase, alkaline phosphatase, glucose-6-phosphate dehydrogenase, acetate kinase, Aequorin, beta-lactamase, laccase, Vargula luciferase), a small molecule (e.g., biotin, 8-azidoadenosine 2',3'-biotin or 8-azidoadenosine 5'-triphosphate [γ]-biocytinamide), a metal (e.g., colloidal gold, nanogold, europium III, transition metal e.g., 99mTc, 188Re, 186Re), a fluorescent molecule (e.g., a lanthanide chelate, rhodamine, rhodamine 6G, rhodamine red, sulforhodamine, fluoroscein, Fort Orange, Birch Yellow, Hops Yellow, a cyanine dye (e.g., Cy2, Cy3, Cy3.5, Cy5, Cy5.5), phycoerythrin, Lake Placid Blue, Adirondack Green, Catskill Green), a phosphorescent marker (e.g., a porphyrin or a platinum(II) or palladium(II) complex of a porphyrin), a bioluminescent molecule (e.g., luciferin, obelin, aequorin) or a chemiluminescent molecule (e.g., an acridinium ester).

Preferred labels for competitive assays are generally metals, small molecules, radioisotopes, fluorescent, chemiluminescent, bioluminescent or phosphorescent labels.

In performing such embodiments, it is known that detection of an enzyme conjugated to protein or antibody generally requires incubation with a suitable substrate. Substrates for each of the enzymes listed are known in the literature. Commonly used chromogenic substrates for horseradish peroxidase (HRP), alkaline phosphatase (AP), beta-galactosidase (β-gal) and glucose-6-phosphate dehydrogenase (G-6-PDH) include 2,2'-azino-di[3-ethyl-benz-thiazoline sulfonic acid] (HRP), 3,3',5,5'-tetramethylbenzidine (HRP), o-phenylenediamine (HRP), p-nitrophenyl-phosphate (AP), o-nitrophenyl-β-D-galactopyranoside (β-gal), chloro-phenolic red-β-D-galactopyranoside (β-gal) and NADP glucose 6-phosphate (G-6-PDH). Preferred fluorescent substrates for HRP, AP and β-gal include p-hydroxyphenylacetic acid (HRP), 3-(p-hydroxyphenyl) propionic acid (HRP), 4-methylumbelliferyl phosphate (AP), 4-methylumbelliferyl-β-D-galactopyranoside (β-gal), fluorescein di-β-D-galactosidase (β-gal), 4-methylumbelli-feryl-galactoside 6-sulfate (β-gal), and 3,6-fluophosphate. Acetate kinase enzyme activity may be detected in the presence of acetylphosphate when linked to a luciferase reaction using the bioluminescent substrate luciferin essentially as described by Ito et al., Anal. Sci 19, 105-109, 2003, which is incorporated herein by reference. Aequorin consists of apoaequorin (22,400 Mw), coelenterazine (luminophore) and molecular oxygen and emits blue light at about 469 nm as a single turnover event when Ca2+ binds to it.

The present invention clearly encompasses embodiments employing multiple labelled moieties e.g., PYY[1-36] and/or PYY[3-36] and/or PYY[1-9] and/or PYY[13-36] peptide and an antibody capable of binding to a PYY peptide or a secondary antibody, or in the case of competition assays, wherein a test antibody or protein and a reference antibody or protein are labelled. In such cases, it is preferred for the labelled moieties to be differentially labelled to permit their separate detection. By "differentially labelled" is meant that the reporter molecules are not the same. For example, a PYY reference sample may be labelled with rhodamine and an antibody labelled using fluorescein, such that both molecules are capable of being detected. Alternatively, a test antibody and reference antibody may be labelled respectively with rhodamine and fluorescein to permit their separate detection. Such embodiments are well-known to a skilled artisan.

Alternatively, immunoassays may be performed in parallel using different aliquots of the antibody or protein extract or other sample being tested.

Particularly preferred immunoassay formats for the present invention include an enzyme-linked immunosorbent assay (ELISA), for example a direct ELISA or a sandwich ELISA and immunochromatography (IC). In another example the format is an indirect ELISA. Specific examples of these assays are described in further detail herein below.

a) Direct ELISA

Direct ELISA is the most basic of ELISA configurations. It is used to detect an antigen (PYY) after it has been attached to the solid phase (e.g. a membrane or polystyrene microwell or dipstick). An antibody (preferably a monoclonal antibody of the present invention) which has been conjugated with a detectable label is then incubated with the captured antigen. After washing off excess conjugate and incubating with a substrate and chromogen, the presence of an expected colour indicates a specific Antibody-Antigen interaction.

b) Sandwich ELISA

In one example of a sandwich ELISA format, a first antibody or fragment thereof is provided bound to a solid support such as a microwell plate, tube, membrane, beads, particles or suitable sensor. A sample containing antigen i.e. PYY is added and allowed to react with the immobilised antibody. After the solid support is washed, a second detectable label-conjugated antibody having high affinity for a different epitope on the antigen is added and allowed to react with the bound antigen. After any free second antibody is removed by washing, substrate is added and any detectable product is measured.

Preferably, the first antibody is a polyclonal antibody. Preferably, the second conjugated antibody is a monoclonal antibody according to the present invention.

It is preferable to use a blocking agent to prevent non-specific binding and to conduct the ELISA assay with washing steps as is well known in the art.

c) Immunochromatography (IC)

IC strip formats have become increasingly popular for qualitative and semi-quantitative assays which use visual detection schemes. This type of assay generally involves the application of a liquid test sample suspected of containing an analyte (eg PYY) to be detected to an application zone of an immunochromatographic test strip. The strip is comprised of a matrix material through which the test fluid and analyte suspended or dissolved therein can flow by capillarity from the application zone to a capture zone where a detectable signal, or the absence of such, reveals the presence (or absence) of PYY in a test sample.

In one embodiment of an IC test format, the strip will include means for immunospecifically binding the analyte to be detected with a high affinity binding partner (e.g. a monoclonal antibody) which bears a detectable label. The label may be one that is visible to the naked eye such as colloidal metal particles or coloured latex, an enzyme that forms a visible signal when contacted with a suitable substrate or one that is detectable only with the use of an instrument such as a chemiluminescent or radio active label.

In one example, the IC test strip contains an enzyme labelled, mobile monoclonal antibody having high affinity for PYY which is in a sample application zone. If PYY is present in the test sample, it will combine with the labelled monoclonal antibody to form a complex which will flow along the strip to a detection zone which contains a substrate for the enzyme label which is capable of providing a coloured response in the presence of the enzyme. The strip may contain a zone in which PYY is immobilized, so that labelled monoclonal antibody which does not combine with PYY, due to the absence of PYY in the sample, will be captured and thereby inhibited from reaching the detection zone.

There have been published various modifications of this technique, all of which involve some specific binding system in which the presence or absence of analyte in a test sample is determined by the detection or lack thereof of labelled binding partner (antibody) in the capture zone.

An alternative to the above described immunoassay which detects the free labelled monoclonal antibody is the so called sandwich format in which the capture zone contains immobilized monoclonal antibodies against an epitope of PYY. In this format, there is formed a sandwich of PYY between the immobilized monoclonal antibody and a labelled antibody which is generally specific for PYY to provide the detectable signal in the capture zone. Accordingly, in this example a first antibody which is generally specific for PYY is bound to a detectable label to form a labelled antibody complex. The labelled antibody complex can be applied on the application pad and the sample added thereto or alternatively, the labelled antibody complex is contacted with the test sample and then applied to the IC strip test. In either case, preferably, if the sample contains PYY, then the PYY binds with the labelled antibody complex and moves though the membrane by capillary action. If the desired antigen is present i.e. PYY, it will bind to the second antibody (i.e. a monoclonal antibody of the present invention) which is immobilized to form a test line or reaction zone and a detectable test line is formed. Preferably, if a sample contains PYY, intensity of the test line depends on the concentration of PYY in the sample.

In one preferred example, the rest of the particles will flow through and be captured by a second stationary antibody zone, thus forming the control line. Preferably, a control line is used to confirm that the test is working properly. Appearance of two lines, therefore, indicates a positive result, while a negative test produces only one line.

Use of a monoclonal antibody or fragment thereof (e.g. Fab and F(ab')2), recombinant antibody or fragments thereof or recombinant antibody fragment (e.g. scFv) as the second antibody in these tests provide significant commercial advantages over, for example, polyclonal antibodies. First, they recognise a limited number of epitopes and, for that reason, do not form aggregating complexes which can compromise ELISA or IC performance. Secondly, they are constant and reproducible reagents.

Not all IC formats rely on an enzyme labelled binding partner/enzyme substrate for providing the signal for detection of the analyte. U.S. Pat. No. 4,806,311 discloses a multizone test device for the specific binding assay determination of an analyte and an immobilized binding partner for the analyte together with a capture zone for receiving labelled reagent which migrates thereto from the reagent zone. The capture zone contains an immobilized form of a binding substance for the labelled reagent. The labelled reagent bears a chemical group having a detectable physical property which is detectable on the basis of such physical property, so that it does not require a chemical reaction with another substance in order to be detected. U.S. Pat. No. 4,703,017 describes the use of visible particulate labels for the receptor. Various particulate labels such as gold sol particles and visible dye containing liposomes are mentioned. Accordingly, detectable labels include, for example, a colloidal gold particle, a detectable enzyme, a coloured particle, a fluorescent compound, a dye, or a latex bead.

d) Indirect ELISA

Antibody can be detected or quantitatively determined with an indirect ELISA. Serum or some other sample containing a primary antibody is added to an antigen/sample-coated microtiter well and allowed to react with the antigen/sample attached to the well. After any free primary antibody is washed away, the presence of antibody bound to the antigen is detected by adding a detectable label-conjugated secondary anti-species antibody, which binds to the primary antibody. Any free secondary antibody is then washed away, a substrate for the detectable label is added. The amount of reaction product that forms is then measured. In one example the detectable label is an enzyme.

In this case substrate for the enzyme is added and the amount of reaction product that forms is measured for example by specialized spectrophotometric plate readers.

Reference Samples

As will be apparent, the diagnostic and prognostic methods provided by the present invention may require a degree of quantification to determine either, the amount of a PYY protein that is diagnostic or prognostic of obesity, a complication associated with obesity or a bone disorder or disease state. Such quantification can be determined by the inclusion of appropriate reference samples in the assays described herein, wherein said reference samples are derived from healthy or normal individuals.

In one embodiment, the reference sample comprises e.g., serum and/or cerebrospinal fluid or fractions thereof that comprise PYY tissues obtained from one or more healthy subjects who have no familial predisposition to obesity, bone disease or a complication of obesity and who show few or no associated risk factors e.g., arthritis, hypertension, an eating disorder, etc. Highly preferred reference samples from such subjects comprise blood, serum, plasma.

A reference sample and a test (or patient) sample are, both processed, analysed or assayed and data obtained for a reference sample and a test sample are compared. In one embodiment, a reference sample and a test sample are processed, analysed or assayed at the same time. In another embodiment, a reference sample and a test sample are processed, analysed or assayed at a different time.

In an alternate embodiment, a reference sample is not included in an assay. Instead, a reference sample may be derived from an established data set that has been previously generated. Accordingly, in one embodiment, a reference sample comprises data from a sample population study of healthy individuals, such as, for example, statistically significant data for the healthy range of the integer being tested. Data derived from processing, analysing or assaying a test sample is then compared to data obtained for the sample population.

Data obtained from a sufficiently large number of reference samples so as to be representative of a population allows the generation of a data set for determining the average level of a particular parameter. Accordingly, the amount of a protein that is diagnostic or prognostic of an infection or disease can be determined for any population of individuals, and for any sample derived from said individual, for subsequent comparison to levels of the expression product determined for a sample being assayed. Where such normalized data sets are relied upon, internal controls are preferably included in each assay conducted to control for variation.

Diagnostic Assay Kits

The present invention provides a kit for determining an amount of PYY[1-36] in a biological sample. In one embodiment, the kit comprises:
(i) one or more isolated antibodies that bind specifically to PYY[1-36] or an immunogenic fragment or epitope thereof comprising the N-terminal portion of PYY[1-36] from position 1 to about position 3; and
(ii) means for detecting the formation of an antigen-antibody complex.

The present invention also provides a kit for determining an amount of PYY[3-36] in a biological sample. In one embodiment, the kit comprises:
(i) one or more isolated antibodies that bind specifically to PYY[3-36] or an immunogenic fragment or epitope thereof that does not comprise the N-terminal portion of PYY[1-36] from position 1 to about position 3; and
(ii) means for detecting the formation of an antigen-antibody complex.

The present invention also provides a kit for determining an amount of PYY[1-36] in a biological sample. In one embodiment, the kit comprises:
(i) one or more isolated antibodies that bind specifically to PYY[1-36] or an immunogenic fragment or epitope thereof comprising the N-terminal portion of PYY[1-36] from position 1 to about position 3; and
(ii) one or more isolated antibodies that bind specifically to PYY[3-36] or an immunogenic fragment or epitope thereof that does not comprise the N-terminal portion of PYY[1-36] from position 1 to about position 3; and
(ii) means for detecting the formation of an antigen-antibody complex.

In preferred embodiments, the kit of the present invention will also comprise an amount of a synthetic PYY peptide e.g., for the preparation of a standard calibration curve to quantify the amount of a PYY peptide in a sample. Preferred peptides for inclusion in such kits are selected from the group consisting of:
(i) an isolated or synthetic PYY peptide comprising at least the N-terminal portion of PYY[1-36] from position 1 to about position 3 for binding to an antibody that binds specifically to PYY[1-36]; and
(ii) an isolated or synthetic PYY peptide comprising an internal portion of PYY[1-36] from about position 3 to about position 13 for binding to an antibody that binds specifically to PYY[3-36].

Optionally, the kit further comprises means for the detection of the binding of an antibody, fragment thereof or a ligand to a PYY peptide. Such means include a reporter molecule such as, for example, an enzyme (such as horseradish peroxidase or alkaline phosphatase), a substrate, a cofactor, an inhibitor, a dye, a radionucleotide, a luminescent group, a fluorescent group, biotin or a colloidal particle, such as colloidal gold or selenium. Preferably such a reporter molecule is directly linked to the antibody or ligand.

The present invention is further described with reference to the following examples and the accompanying drawings.

EXAMPLE 1

Production of Mice Having Reduced PYY Expression

PYY Targeting Vector Construction and Gene Disruption

A 130 kb mouse genomic BAC clone comprising the PYY gene was mapped and various fragments sub cloned. A 10.5 kb SpeI fragment containing 6 kb 5'-flanking sequence, the entire PYY gene and 3 kb 3'-flanking sequence was chosen for the construction of a PYY-Cre construct to target PYY disruption. The sequence immediately behind the start codon of the PYY gene starting at nucleotide 6330 continuing to the NheI restriction site at nucleotide 10377 was replaced with a cassette which allows the inducible transcription of the Cre and EGFP genes under the control of the PYY promoter. To achieve this, the reverse Tet repressor (rTetR) gene (Clontech) was fused in frame with the mouse PYY gene. This was followed by the insertion of a cassette containing the EGFP gene in opposite orientation, which had been modified to replace the start-codon replacing with a loxP sequence. Subsequently, a cassette containing the PGK-Neo and Zeocin resistant genes were inserted for selection purposes. The Cre gene under the control of the 'tetracycline responsive element' (TRE) was inserted downstream of this, in 3'-5' orientation. The Cre gene was also modified at the STOP codon, by replacing it with a loxP sequence to allow the in frame fusion with the EGFP gene upon activation of the TRE element. A 4.5 kb EcoRI fragment of the downstream sequence of the PYY gene was used as the 3'arm of the targeting construct. The linearised version of that clone was transfected into ES cells. Two positive clones were injected into C57BL/6 blastocysts and chimeric mice were bred to generate heterozygous and subsequently homozygous PYY-Cre knock-in mice were bred.

The genotype of the mice were determined by Southern blot analysis of NheI digested DNA employing probes located outside the targeting sequence. Probe A and B were generated by PCR (A for: 5'-AGTGATTTGCTCAGAAGC-3' and rev: 5'-CTAGTTCTATAGACCAGAC-3') and (B for: 5'-CTGCCATGGCTGACCATGC-3' and B rev: 5'-TGGTG-GTGGCATGCACAC-3'). Successful induction of the Cre gene and fusion with the EGFP gene was confirmed with PCR using the combination of oligos GFP-R (5'-GGACACGCT-GAACTTGTG-3') and Neo-F (5'-CTGCTCTTTACT-GAAGGCTC-3') for the non-induced form and the combination of GFP-R and Cre-A (5'-CCTGGTCTGGACACAGTG-3) for the induced form. The conditions for all PCR reactions were 35 cycles of 94° C. for 45 s, 58° C. for 1 min and 72° C. for 20 s.

Results

Figure 1B:
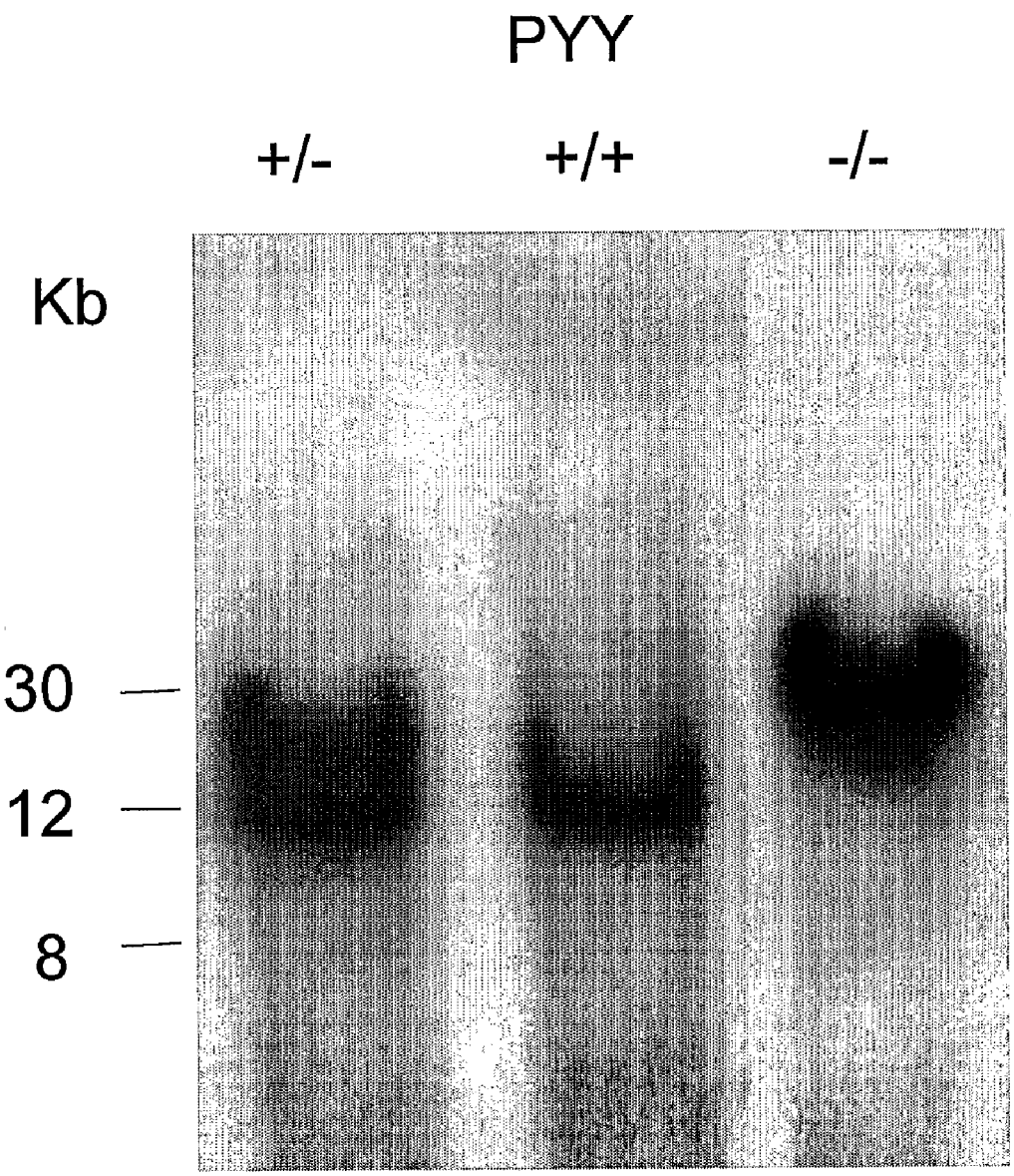
FIG. 1b is a copy of a photographic representation showing a Southern hybridization analysis of genomic DNA isolated from wild-type (+/+), heterozygous (+/−) PYY knockout, or homozygous($^{-/-}$) PYY knockout mice cut with either NheI or BamHI restriction endonuclease and probed using probe A (depicted in FIG. 1a).
Figure 1C:
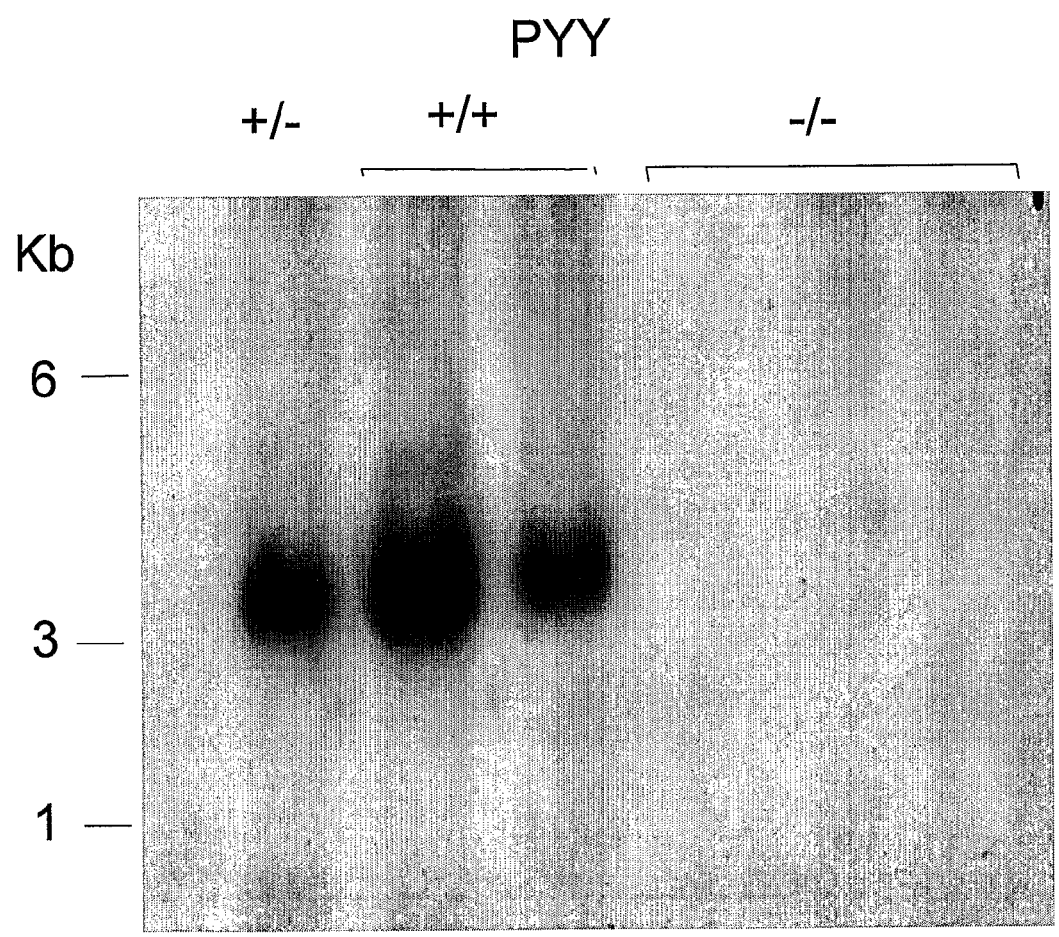
FIG. 1c is a copy of a photographic representation showing a Southern hybridization analysis of genomic DNA isolated from wild-type (+/+), heterozygous (+/−) PYY knockout, or homozygous($^{-/-}$) PYY knockout mice cut with either NheI or BamHI restriction endonuclease and probed using probe B (depicted in FIG. 1a).

A knockout-targeting vector for the PYY gene was designed which also allows the PYY promoter-driven expression of the Cre-recombinase gene under the control of the inducible tetracycline promoter (FIG. 1a). Two positive ES cell clones for the PYY construct were injected into blastocysts originating from C57BL/6 mice and implanted into pseudo pregnant mice. Offspring with the highest percentage of agouti coat colour were crossed with C57BL/6 mice in order to obtain heterozygotes and subsequently homozygous mice. DNA isolated from tail tips was used in Southern blot analysis (NheI) to confirm correct integration and modification of the targeted allele (FIG. 1b, FIG. 1c). Successful activation of the Cre-recombinase gene was confirmed by PCR.

Breeding of heterozygous germ line knockout animals produced a slight deviation from the expected Mendelian ratio of genotypes 25:50:25 to 43:38:19 (n=7 breeding pairs). However, $PYY^{-/-}$ animals breed normally with an average litter size of 7.15±0.37 pups per litter, which was not significantly different from wild type litter sizes of 6.57±0.97 pups (n=7-13 breeding pairs). The gender ratio in $PYY^{-/-}$ offspring shows a trend towards a greater proportion of females (57.1%, n=112).

EXAMPLE 2

Methods for Assessing the Effects of Reduced PYY Expression

Measurement of Food Intake, Bodyweight, Temperature

All research and animal care procedures were approved by the Garvan Institute/St Vincent's Hospital Animal Experimentation Ethics Committee and were in agreement with the Australian Code of Practice for the Care and Use of Animals for Scientific Purpose. 10-20 animals per genotype originating from 3-4 different breeding pairs were group-housed under conditions of controlled temperature (22° C.) and illumination (12 hour light cycle, light onset at 7.00 am).

Mice were fed a normal chow diet ad libitum (6% calories from fat, 21% calories from protein, 71% calories from carbohydrate, 2.6 kilocalories/g, Gordon's Specialty Stock Feeds, Yanderra, NSW, Australia) or a high fat diet (46% calories from fat, 21% calories from protein, 33% calories from carbohydrate, 4.72 kilocalories/g) from 4-5 weeks of age onwards. The high fat diet, made in-house, was based on the composition of Rodent Diet Catalogue Number D12451 (Research Diets, New Brunswick, N.J.), with the exception that safflower oil and copha were used in place of soybean oil and lard, respectively. Body weight was monitored at the same time each week from 4 weeks of age onwards.

At 10 weeks of age, body temperatures were taken at the same time over 3 consecutive days using a rectal probe (Physitemp Instruments Inc, New Jersey, USA). Mice were then transferred to single housing and allowed to acclimatize for 3-4 nights. At 11 weeks of age, body weight, water intake and food intake (in account of spillage and fecal output) was measured over 4 sequential 24-hour periods. Spillage was determined by subtracting the pre-weighed cage contents balance from the cage contents balance after 24 hours once the faeces had been removed from the bedding.

Glucose Tolerance Tests

At 13 weeks of age, mice were fasted for 24 hours. The next day, 40 µl of blood was collected from the tip of the tail (t=0 sample). Mice were administered an intraperitoneal injection of D-glucose (50% w/v solution, 1 g/kg). Blood samples of ~40 µL were collected from the tip of the tail at t=15, 30, 60, 90 and 120 minutes post-injection for determination of serum glucose and insulin levels. Incremental areas under the glucose response curves were calculated (after subtracting fasting baseline glucose levels) between 0 and 120 minutes after glucose injection, and expressed as mM glucose per minute. Separate sets of mice were also analyzed for glucose tolerance at weeks of age.

Tissue Collection and Analysis

Wild type and $PYY^{-/-}$ mice at 14 or 28 weeks of age were killed by cervical dislocation between 12.00-14.00 h for collection of trunk blood. Mice were routinely culled within 60 seconds of handling to minimize changes in corticosterone levels. Brains were immediately removed and frozen on dry ice. After decapitation, mice were scanned for whole body lean and fat mass using a dual-energy x-ray absorptiometry (Lunar PIXImus2 mouse densitometer; GE Healthcare). White adipose tissue depots (right inguinal, right epididymal or periovarian (gonadal), right retroperitoneal and mesenteric), pancreas, stomach, small intestine, colon, liver, kidney, heart, ovary, testis and seminal vesicle were removed and weighed. Serum leptin and glucagon levels were measured by radioimmunoassay kits from Linco Research (St Louis, Mo., USA), insulin levels were measured using an ELISA kit from Mercodia (Uppsala, Sweden), serum corticosterone and testosterone concentrations were measured with kits from ICN Biomedicals (Costa Mesa, Calif., USA), serum IGF-1 was determined using a RIA kit from Bioclone (Marrickville, NSW, Australia) and glycemia was determined with a glucose oxidase assay kit (Trace Scientific, Melbourne, Australia).

PYY Staining of the Pancreas, Small and Large Intestine.

Tissues were fixed in 4% paraformaldehyde in phosphate buffered saline overnight at 4° C. and transferred to 70% ethanol the next day, before being processed and embedded in paraffin. 7 µm sections were deparaffinised in xylene and dehydrated from 100% ethanol to water. Slides were incubated in 1% $H_2O_2$ in methanol for 20 minutes, rinsed and blocked with 20% normal goat serum in phosphate buffered saline for 20 minutes. Excess blocking solution was removed before applying the rabbit anti-human PYY antiserum (Peninsula Laboratories, Calif. USA) at 1:1000 dilution for 1 hour at 37° C. Cross-reactivity was minimized by incubating the antiserum with protein extracted from a brain of PYY knockout mouse. Slides were rinsed in phosphate buffered saline before incubation with goat anti-rabbit IgG-horse radish peroxidase conjugated antibody (Zymed Laboratories, San Francisco, Calif., USA) at 1:1000 dilution for 1 hour at room temperature. Slides were rinsed in phosphate buffered saline and treated with the diaminobenzidine from DAKO (Carpinteria, Calif., USA) for 5 minutes. Slides were rinsed in water, counterstained in haematoxylin (30 seconds), rinsed and dipped in lithium carbonate, dehydrated through graded ethanol and xylene before coverslipping.

PP Staining of the Pancreas.

Sections treated as above were blocked in 20% normal donkey serum prior to application of the guinea pig anti-rat PP serum (Linco Research, Missouri USA) (1:1000) for 1 hour at 37° C. Slides were rinsed in phosphate buffered saline and incubated with biotinylated donkey anti-guinea pig IgG antibody (1:5000) (Jackson ImmunoResearch Laboratories, West Grove, USA) for 30 minutes at room temperature. The slides were rinsed in phosphate buffered saline and incubated with the Avidin-Biotin-Peroxidase Vectastain (Burlingame, Calif., USA) for 30 minutes at room temperature. Slides were rinsed in phosphate buffered saline and treated as above for diaminobenzidine development and counterstaining.

Glucagon Staining of the Pancreas

Sections treated as above were blocked in 10% normal goat serum in phosphate buffered saline for 20 minutes at room temperature. Rabbit anti-glucagon antibody (1:500) (ICN pharmaceuticals, Costa Mesa, Calif.) was applied for 1 hour at room temperature. Slides were rinsed in phosphate buffered saline before application of the peroxidase conjugated goat anti-rabbit IgG (H+ L) (Zymed Laboratories, San Francisco, Calif., USA) (1:1000) for 30 minutes at room temperature. The slides were rinsed in phosphate buffered saline and treated as above for diaminobenzidine development and counterstaining.

Measurement of Islet Cell Size and Number

Six random pancreatic sections were collected from 5 wild type and PYY knockout male mice. Haematoxylin and eosin stained sections were observed using a ProgRes 3008 camera (Zeiss, Jena, Germany) mounted on a Zeiss Axiophot microscope. The average number and size of islet cells per section were quantified using the 20× objective and Leica IM 1000 version 1.20 software (Leica Microsystems, Heerbrig, Switzerland). The average size and number of islets were determined from 6 sections per mouse.

In Situ Hybridization

Coronal brain sections (20 µm) were cut on a cryostat and thaw-mounted on Superfrost slides (Menzel-Glaser, Braunschweig, Germany). The sections were kept desiccated at −80° C. until use. Matching sections from the same coronal brain level of PYY knockout and wild type mice (4-5 male mice per group) were assayed together following the method of Young *Methods Enzymol.*, 168, 702-710, 1989 with slight variations (Tsunashima et al., *Neuroscience*, 80: 1019-1032, 1997). In short, the following DNA oligonucleotides were used:

```
(i)    complementary to mouse NPY-encoding mRNA:
       5'-GAGGGTCAGTCCACACAGCCCCATTCGCTTGTTACCTAGCA
       T-3';

(ii)   complementary to mouse POMC-encoding mRNA:
       5'-TGGCTGCTCTCCAGGCACCAGCTCCACACATCTATGGAG
       G-3;

(iii)  complementary to mouse GHRH-encoding mRNA:
       5'-GCTTGTCCTCTGTCCACATGCTGTCTTCCTGGCGGCTGAGC
       CTGG-3';
and (iv)   complementary to mouse vasopressin-encoding
       mRNA:
       5'-TCAGAGATGGCCCTCTTGCCGCCTCTTGGGCAGTTCTGGAA
       GTA-3'.
```

Oligonucleotide probes were labelled with [$^{35}$S] thio-dATP (1300 Ci/mmol, Amersham, Buckinghamshire, UK) by reaction with terminal deoxynucleotidyltransferase (Roche, Mannheim, Germany) and precipitated with ethanol/sodium chloride. Frozen sections were rapidly immersed in 2% paraformaldehyde in 150 mM NaCl and 10 mM phosphate buffer, pH 7.2 (phosphate buffered saline, PBS) for 10 minutes in an ice bath, rinsed in PBS, immersed in 0.25% acetic anhydride in 0.1 M triethylamine hydrochloride (pH 8.2 in saline) for 10 minutes, dehydrated by ethanol series and delipidated with chloroform. Air-dried sections were hybridized at 42° C. for 18 h with 30 mol (0.6×10$^6$ cpm) labelled oligonucleotide probe in 50 µl hybridization buffer. The hybridization buffer, consisted of 50% formamide, 5×SSC (1×SSC is 150 mM NaCl, 15 mM sodium citrate, pH 7.2), 500 µg/ml salmon sperm DNA, 250 µg/ml yeast tRNA, 1×Denhardt's solution (0.02% ficoll, 0.02% polyvinylpyrrolidone, and 0.02% bovine serum albumin), 10% dextran sulfate, and 20 mM dithiothreitol. Slides were washed four times in 50% formamide in 2×SSC (42° C., 15 minutes), cooled to room temperature for 30 minutes, rinsed in 1×SSC and dipped briefly in water. Sections were then dipped in 70% ethanol, dried and exposed to (Kodak Biomax MR) films for 1-5 days. Subsequently the slides were dipped in (Kodak NTB-2) photosensitive emulsion (diluted 1:1 with distilled water), air dried and exposed for 6 to 14 days. Films and dipped slides were developed with (Kodak D19) developer. Sections were counter-stained superficially with haematoxylin, dehydrated, and coverslipped with Aquamount (BDH, Poots, UK). The corresponding radiolabeled sense DNAs were used to exclude non-specific hybridization of the probe. Sections hybridized with 50 times in excess of unlabeled probe were included as further controls in some experiments.

Autoradiographs were scanned and relative optical densities (ROD) were measured over the arcuate nucleus, the medial septal nucleus, or the paraventricular nucleus. Background measured over white matter was deducted. For evaluation of mRNA levels in scattered neurons, images from dipped sections were digitized using a ProgRes 3008 camera (Zeiss, Jena, Germany) mounted on a Zeiss Axiophot microscope. Silver grain density over single neurons was evaluated using NIH-Image 1.61 software (written by Wayne Rasband and available from anonymous FTP at zippy.nimh.nih.gov). Background labelling was uniform and never exceeded 5% of specific signal.

Activity Measurements:

The total cage activity was recorded using a passive infrared detector (PID, Conrad Electronics, Germany) on top of the cage lid of single-housed animals. The signals of the PIDs were detected by an I/O interface card (PIO48 II, Germany) and stored by custom-made software. Due to the design of the PIDs the maximal number of counts per minute was 20. To show the activity pattern of the mice the data are plotted so that each cycle's activity is shown both to the right and below that of the previous cycle, a so-called double plotted actogram with the x-axis showing 48 hours starting on the left with 00:00 h (ZT 6). In order to test for differences in total activity between the genotypes the activity counts were summed up to 30 minute-bins and a mean/day was calculated by averaging corresponding bins of 7 consecutive days.

Statistical Analyses

Results for body weight, lean and fat mass, food intake, activity measurements, and differences in serum glucose and insulin levels during glucose tolerance tests were compared among groups by repeated measures ANOVA followed by Fisher's post-hoc tests. Differences between PYY$^{-/-}$ and wild type mice in tissue weights and serum hormone and metabolite concentrations were assessed by 3-way ANOVA (effect of PYY deletion, gender and diet) with subsequent Fisher's post-hoc tests. Alterations in neuronal neuropeptide mRNA expression and pancreatic islet parameters between knockout and wild type mice were assessed by ANOVA. StatView version 4.5 (Abacus Concepts Inc, CA, USA) was used for all statistical analyses, and p<0.05 was accepted as being statistically significant.

Measurements of Bone Mineral Density (BMD) and Bone Mineral Content (BMC)

Whole male and female $PYY^{-/-}$ and wild-type animals, and excised femurs and tibiae from such animals, were subjected to dual energy X-ray absorptiometry (DXA) using a Lunar PIXImus2 mouse densitometer (GE Healthcare) according to standard procedures. DXA data from scans were subjected to statistical analyses to determine mean values±standard error in each case; p<0.05 was accepted as being statistically significant.

EXAMPLE 3

Effects of Reducing PYY Expression on Tissue Morphology

Figure 1D:
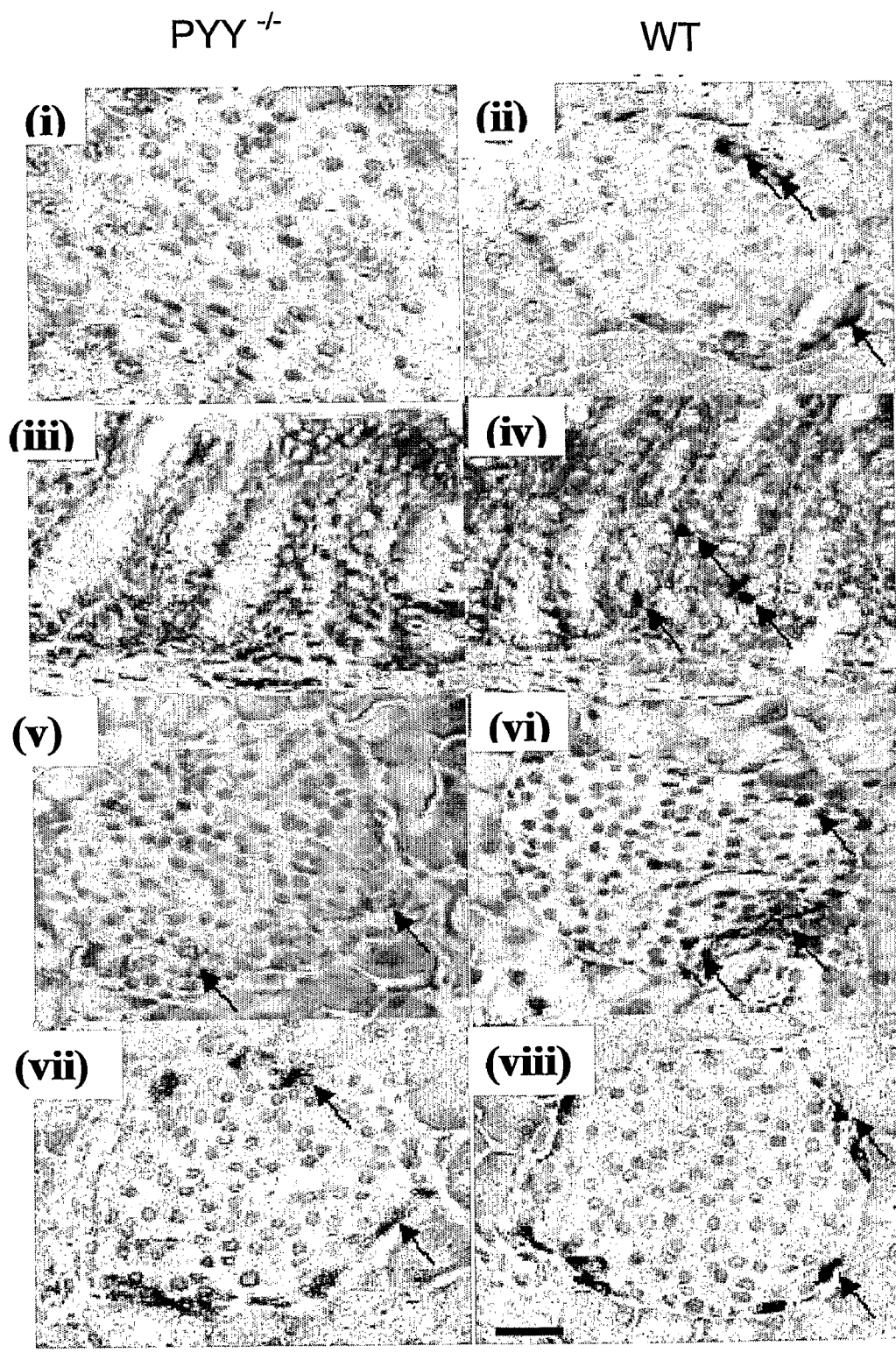
FIG. 1d is a copy of a photomicrograph showing the expression of PYY in the islets of Langerhans (panels (i) and (ii)) and colon (panels (iii) and (iv)) of a PYY$^{-/-}$ mouse (panels (i), (iii)) and wild type (WT) mouse (panels (ii), (iv)), as detected using immunohistochemistry. Data also show expression of pancreatic polypeptide (PP; panels (v) and (vi)) and glucagon level (panels (vii) and (viii)) in the pancreata of a PYY$^{-/-}$ mouse (panels (i), (iii)) and wild type (WT) mouse (panels (ii), (iv)), as detected using immunohistochemistry. Arrows indicate the positively stained cells. Scale bar represents 10 µm.

Successful deletion of the PYY gene was confirmed by the absence of staining for PYY in the pancreas and colon of $PYY^{-/-}$ mice (FIG. 1d, panels (i) to (iv)). The morphology of these PYY-expressing tissues did not show any obvious changes when examined using haematoxylin and eosin staining. Moreover, the average size of the islets of Langerhans (0.022±0.004 mm$^2$) did not significantly differ from that of wild type mice (0.035±0.008 mm$^2$). The same is true for the number of islets per section (6.6±1.3 in $PYY^{-/-}$ versus 8.2±1.5 in wild type mice). Importantly, the expression of the PP gene, which is located only 8 kb downstream of the PYY gene locus, was not influenced by the removal of the PYY gene (FIG. 1d, panels (v) and (vi)), nor were the expression of glucagon (FIG. 1d, panels (vii) and (viii)) or insulin in the islets of Langerhans altered by PYY deletion.

EXAMPLE 4

Effects of Reduced PYY Expression on Bodyweight, Adiposity and Food Intake

Figure 2A:
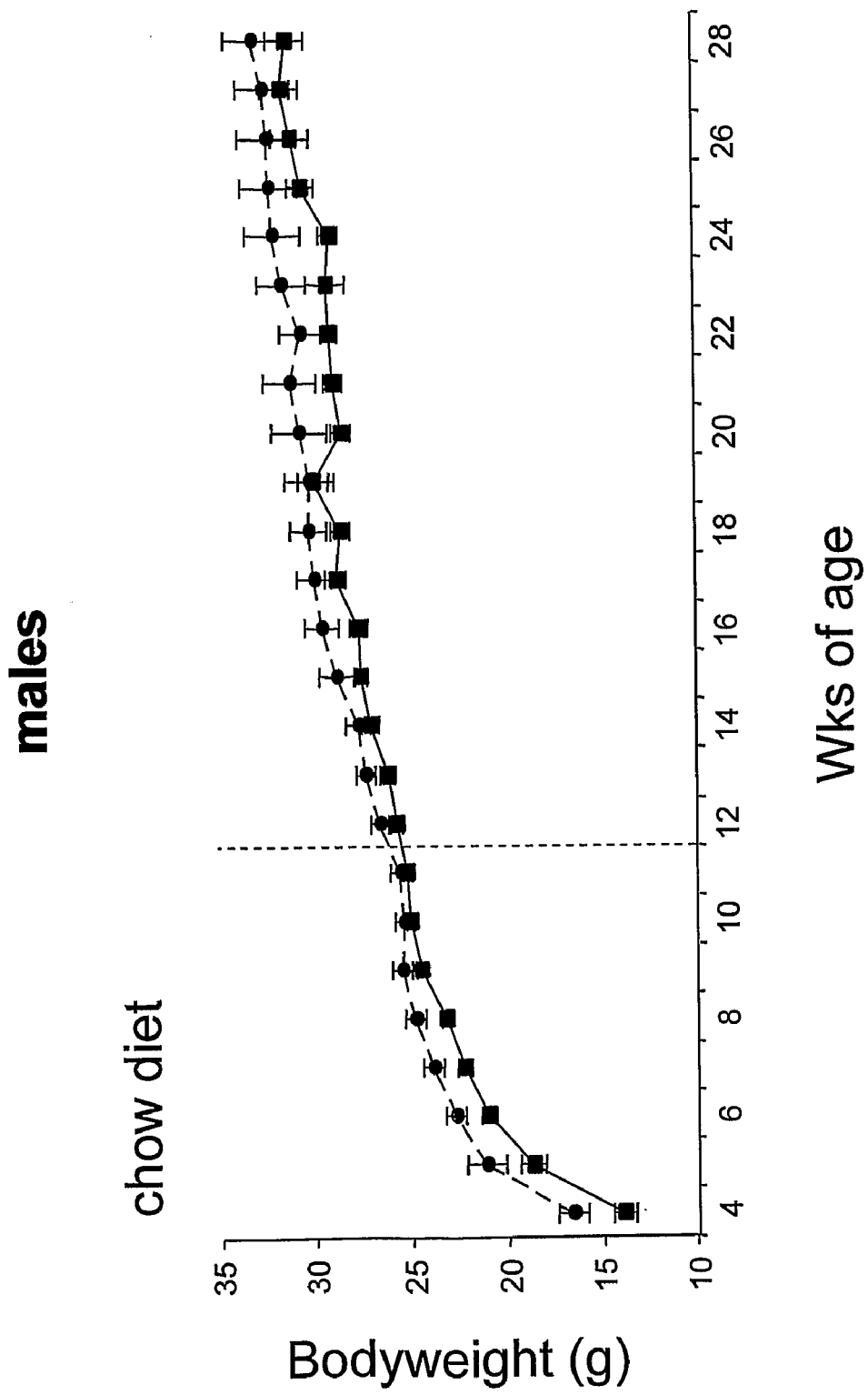
FIG. 2a is a graphical representation showing the effect of PYY deficiency on bodyweight of male mice fed on a standard chow diet. Bodyweights were determined for $PYY^{-/-}$ male mice (circles) or wild-type male mice (squares) fed with standard mouse chow during the period from 4 to 28 weeks of age. Data represents the mean±SEM of 12-20 mice. The dotted line separates the aging mice bodyweight curves where the data represent the mean±SEM of 6-8 mice per group. $^{H}p<0.05$ and $^{HH}p<0.01$ versus wild type mice.
Figure 2B:
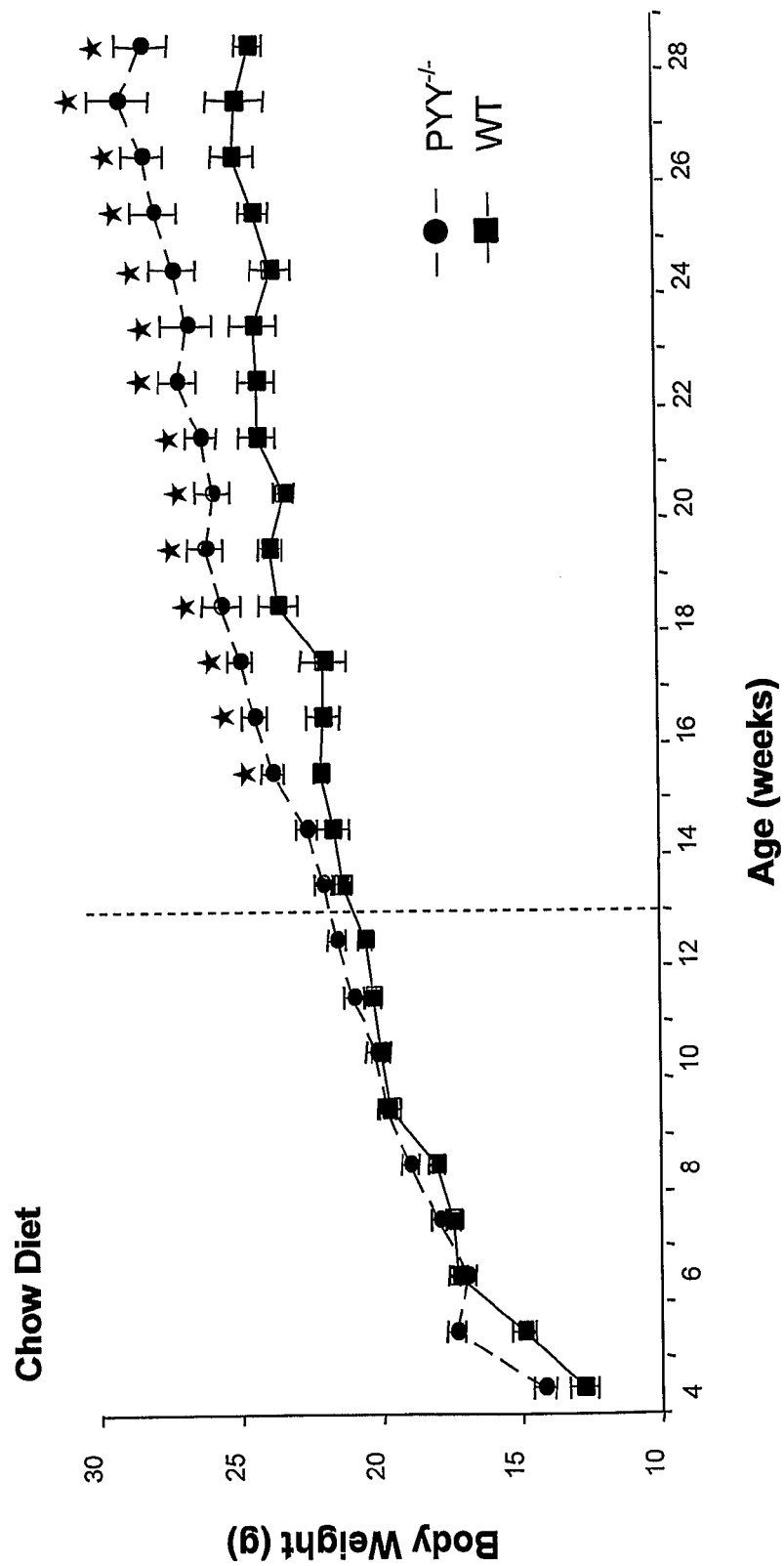
FIG. 2b is a graphical representation showing the effect of PYY deficiency on bodyweight of female mice fed on a standard chow diet. Bodyweights were determined for $PYY^{-/-}$ female mice (circles) or wild-type female mice (squares) fed with standard mouse chow during the period from 4 to 28 weeks of age. Data represents the mean±SEM of 12-20 mice. The dotted line separates the aging mice bodyweight curves where the data represent the mean±SEM of 6-8 mice per group. $^{H}p<0.05$ and $^{HH}p<0.01$ versus wild type mice.

Under chow-fed conditions, $PYY^{-/-}$ mice had a higher body weight than wild type controls (FIG. 2a, FIG. 2b). This difference was more pronounced in female than in male mice, particularly between 15-28 weeks of age. The increases in body weight in 14 week-old, chow-fed male and female $PYY^{-/-}$ mice were associated with a significant increase in total body lean mass (FIG. 2e, FIG. 2f), and a significant decrease in whole body fat mass in the females (FIG. 2h). This significant increase in lean mass was also observed at 20 weeks of age in the chow-fed male knockouts, but not at any other time point (FIG. 2e, FIG. 2f). Interestingly, chow-fed female but not chow-fed male $PYY^{-/-}$ mice also showed a significant increase in fat mass at 28 weeks of age (FIG. 2g, FIG. 2h).

The increased adiposity in 28-week old female $PYY^{-/-}$ mice as determined by DXA was confirmed by marked and significant increases in the weight of all of the white adipose tissue depots measured. Table 1 summarizes the effect of PYY deficiency on food and water intake, temperature, glucose tolerance, serum parameters and tissue weights of 14 week old and 28 week old chow-fed or 14 week old high fat-fed $PYY^{-/-}$ and wild type mice.

Figure 2C:
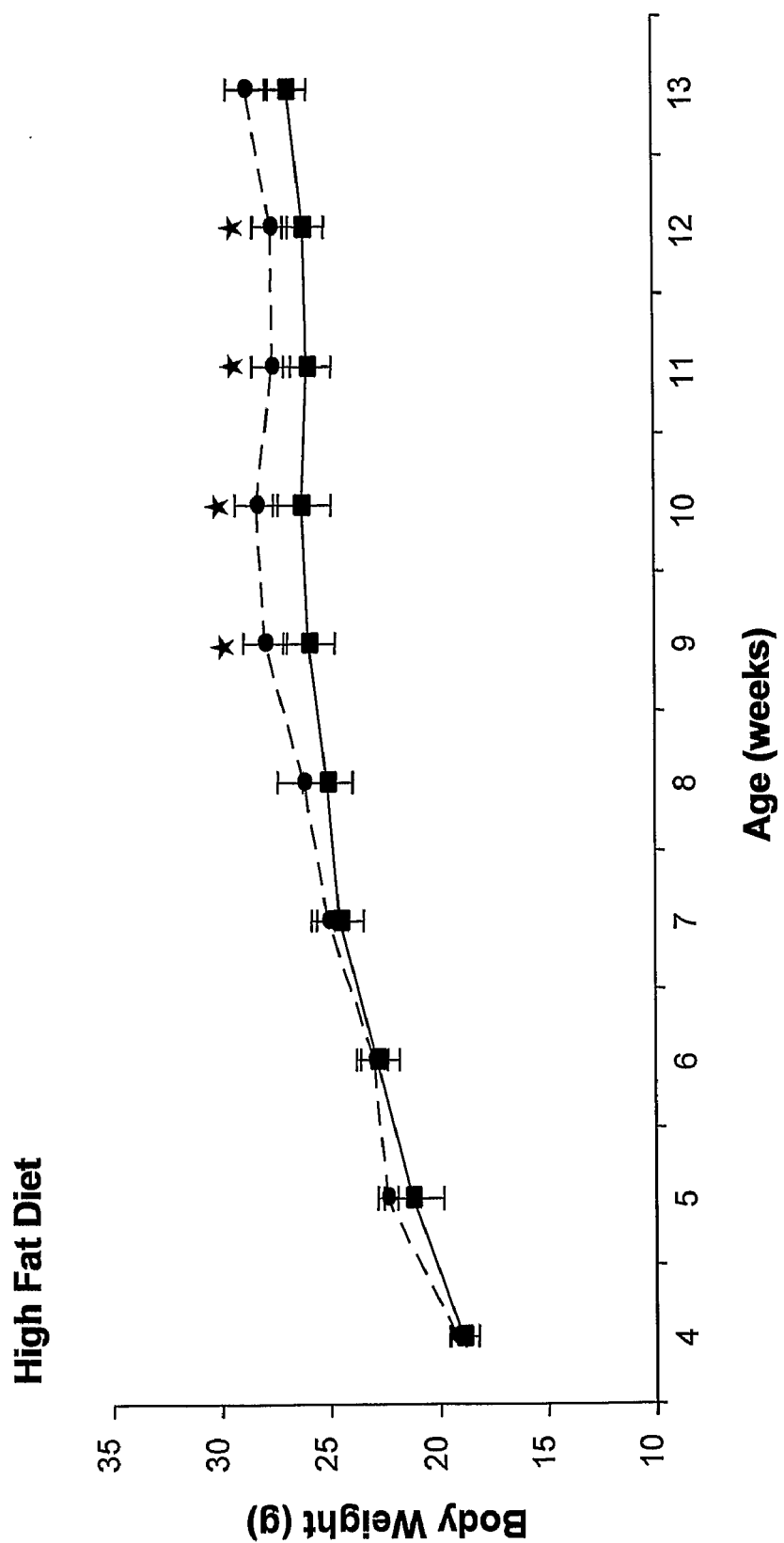
FIG. 2c is a graphical representation showing the effect of PYY deficiency on bodyweight of male mice fed on a high fat diet. Bodyweights were determined for $PYY^{-/-}$ male mice (circles) or wild-type male mice (squares) fed on a high fat diet during the period from 4 to 14 weeks of age. Data represents the mean±SEM of 8-12 mice. $^{H}p<0.05$ and $^{HH}p<0.01$ versus wild type mice.
Figure 2D:
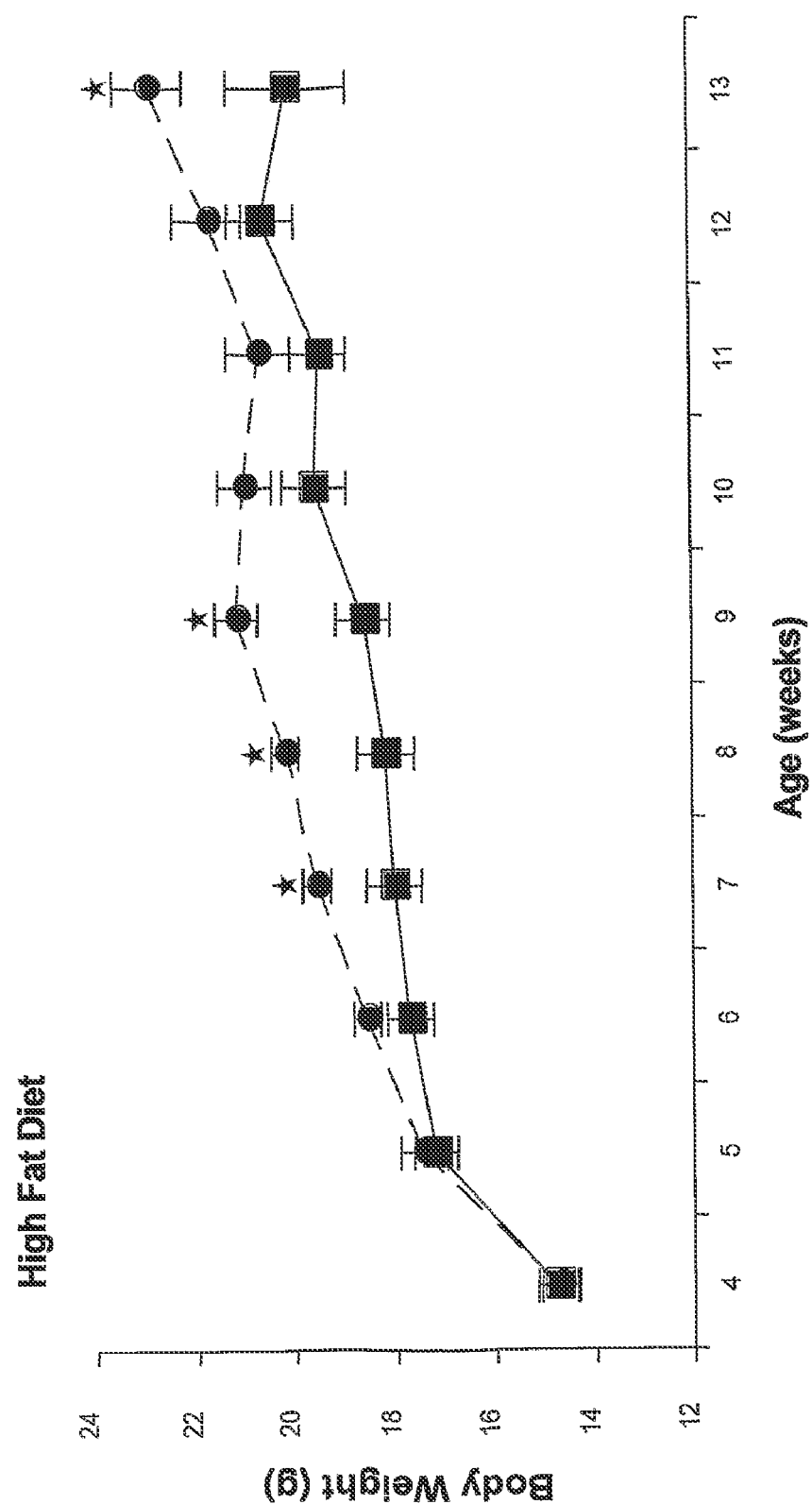
FIG. 2d is a graphical representation showing the effect of PYY deficiency on bodyweight of female mice fed on a high fat diet. Bodyweights were determined for $PYY^{-/-}$ female mice (circles) or wild-type female mice (squares) fed on a high fat diet during the period from 4 to 14 weeks of age. Data represents the mean±SEM of 8-12 mice. $^{H}p<0.05$ and $^{HH}p<0.01$ versus wild type mice.
Figure 2E:
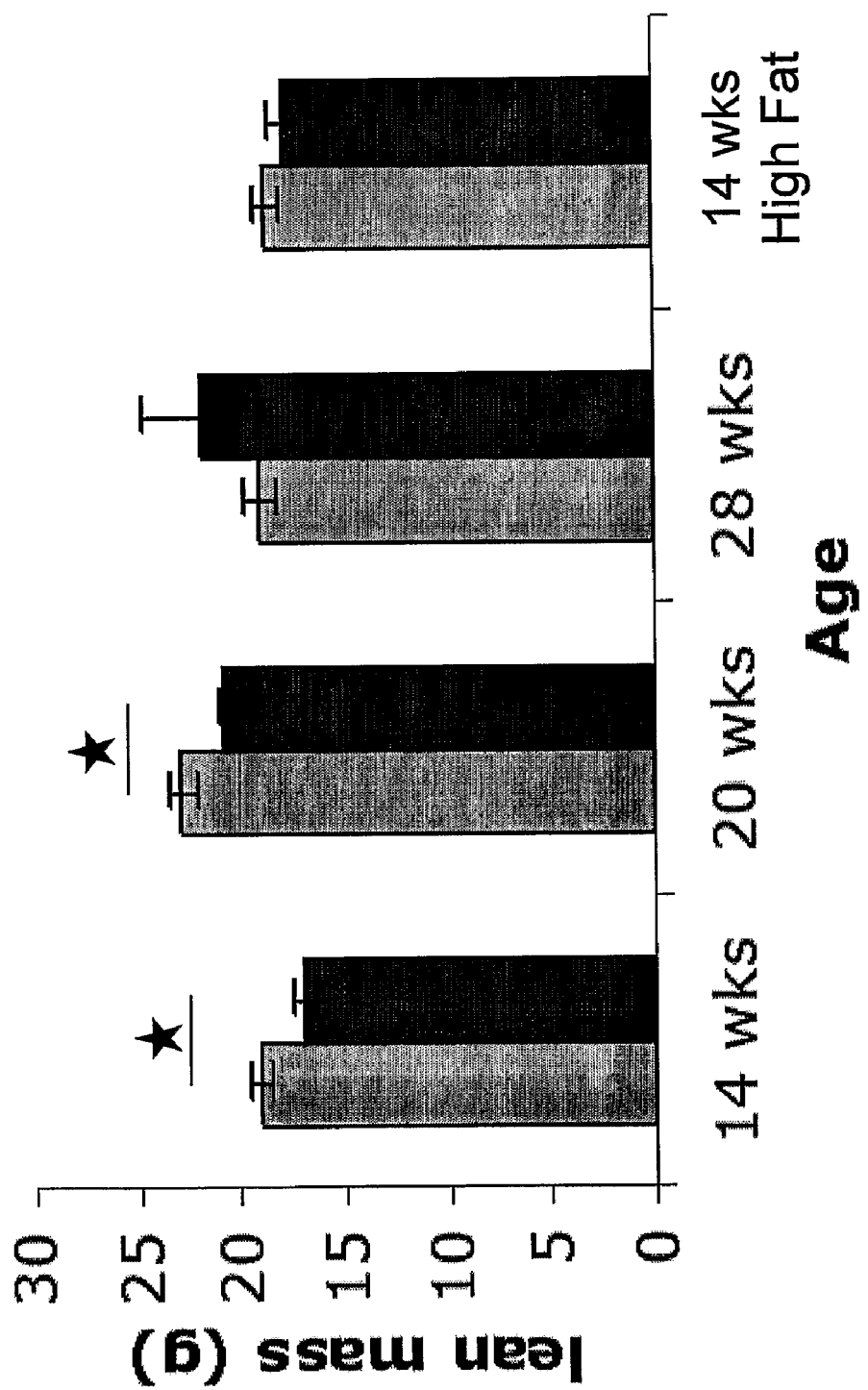
FIG. 2e is a graphical representation showing the effect of PYY deficiency on lean mass (g) of male mice fed, as determined by dual-energy x-ray absorptiometry (DXA). Lean masses were determined for $PYY^{-/-}$ male mice (filled bars) or wild-type male mice (open bars) after feeding to 14 weeks or 20 weeks or 28 weeks of age on a chow-diet, and after feeding to 14 weeks of age on a high-fat diet. Data represents the mean±SEM of 3-8 mice per group. $^{H}p<0.05$ and $^{HH}p<0.01$ versus wild type mice.
Figure 2F:
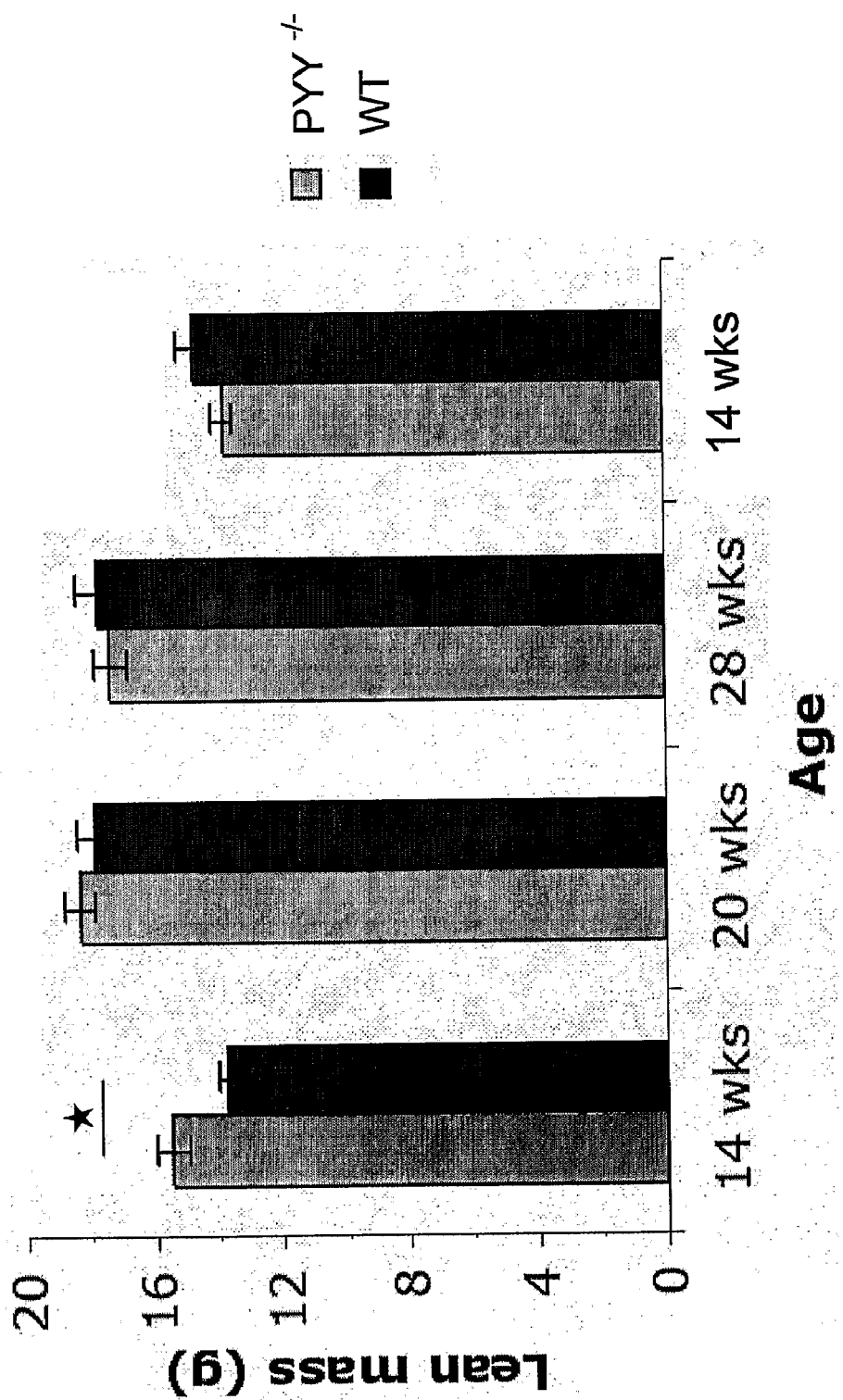
FIG. 2f is a graphical representation showing the effect of PYY deficiency on lean mass (g) of female mice fed on a high fat diet, as determined by dual-energy x-ray absorptiometry (DXA). Lean masses were determined for $PYY^{-/-}$ female mice (filled bars) or wild-type female mice (open bars) after feeding to 14 weeks or 20 weeks or 28 weeks of age on a chow-diet, and after feeding to 14 weeks of age on a high-fat diet. Data represents the mean±SEM of 3-8 mice per group. $^{H}p<0.05$ and $^{HH}p<0.01$ versus wild type mice.
Figure 2G:
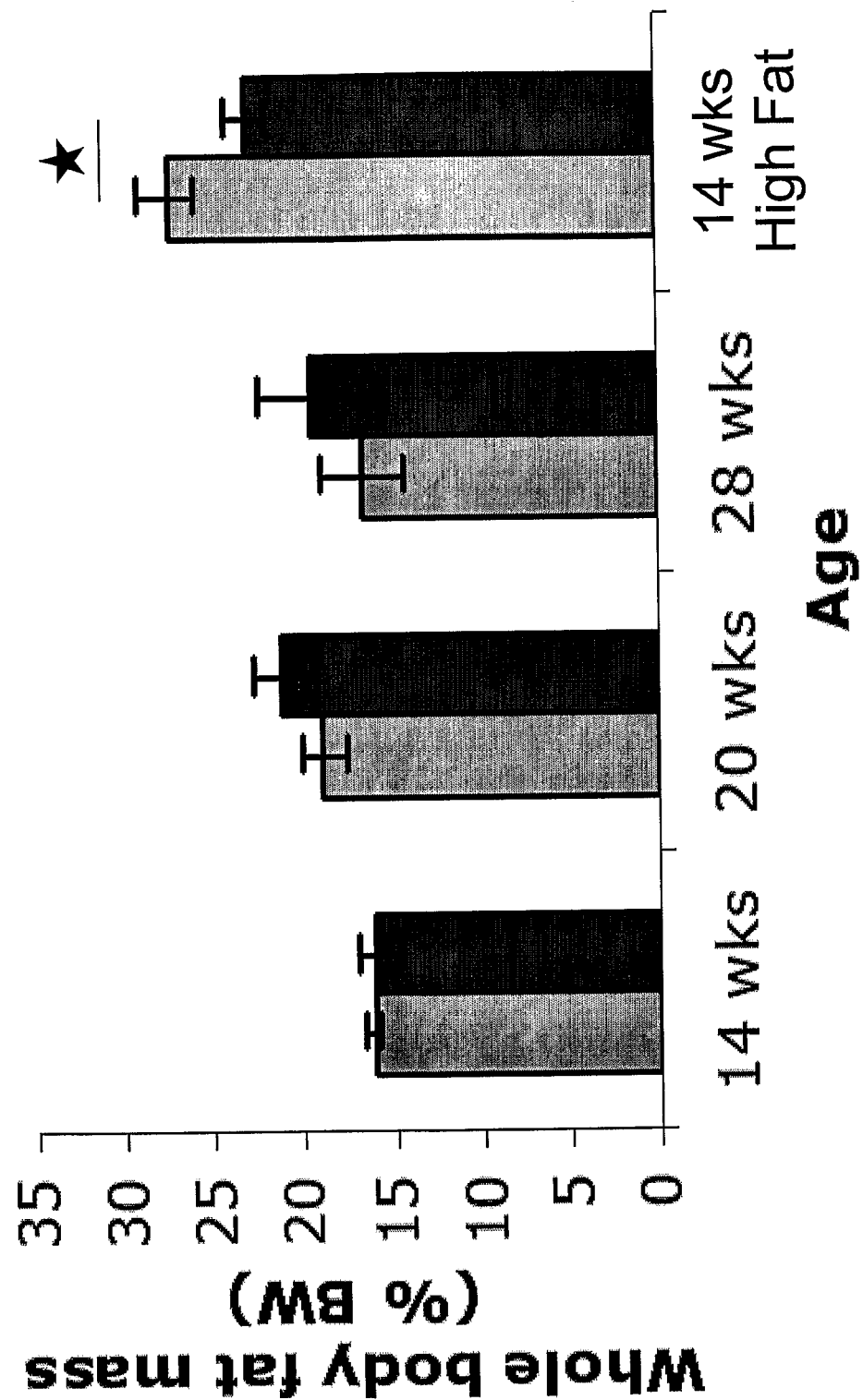
FIG. 2g is a graphical representation showing the effect of PYY deficiency on whole body fat mass (g) of male mice fed on a high fat diet, as determined by dual-energy x-ray absorptiometry (DXA). Whole body fat masses were determined for $PYY^{-/-}$ mice (filled bars) or wild-type male mice (open bars) after feeding to 14 weeks or 20 weeks or 28 weeks of age on a chow-diet, and after feeding to 14 weeks of age on a high-fat diet. Data represents the mean±SEM of 3-8 mice per group. $^{H}p<0.05$ and $^{HH}p<0.01$ versus wild type mice.
Figure 2H:
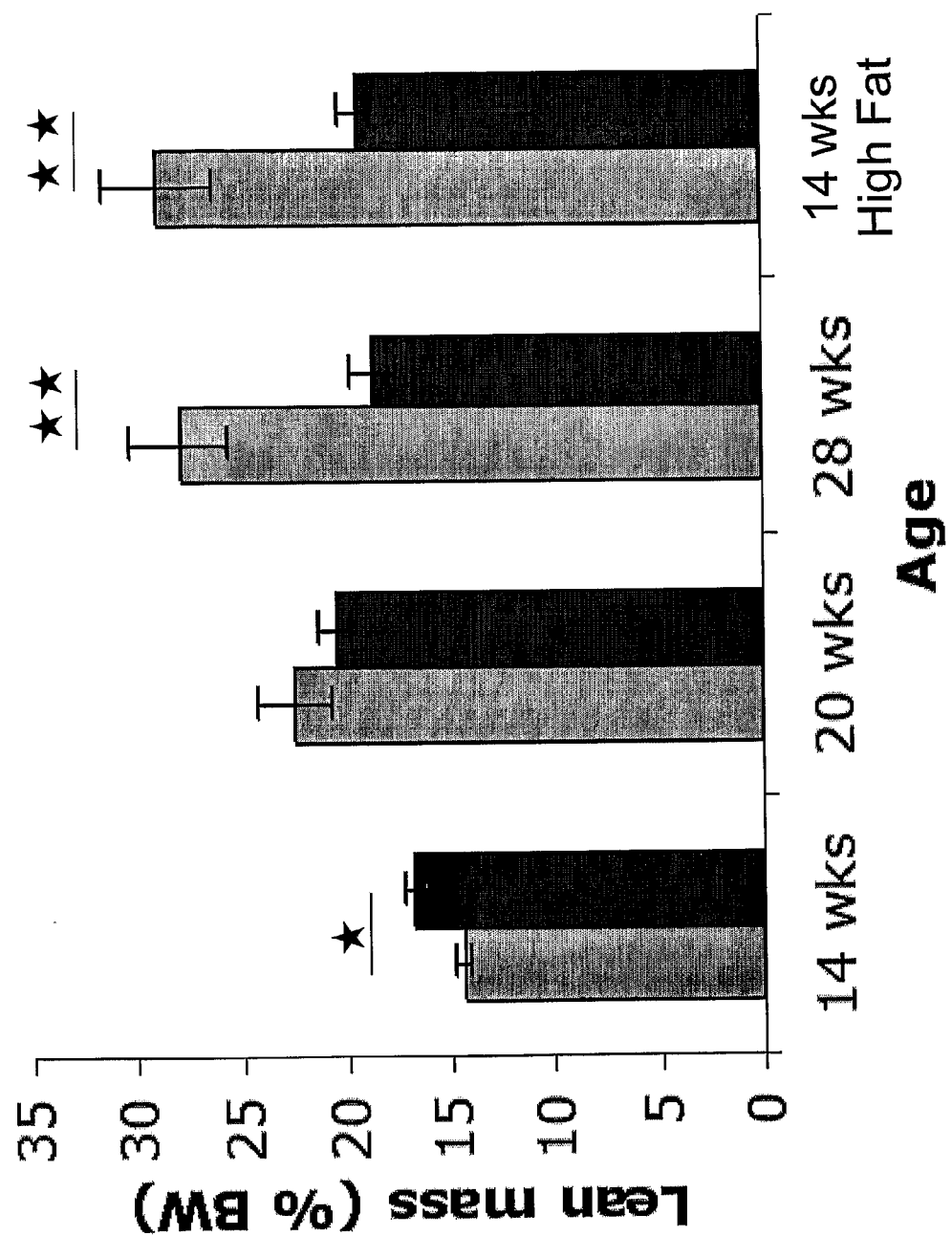
FIG. 2h is a graphical representation showing the effect of PYY deficiency on whole body fat mass (g) of female mice fed on a high fat diet, as determined by dual-energy x-ray absorptiometry (DXA). Whole body fat masses were determined for $PYY^{-/-}$ female mice (filled bars) or wild-type female mice (open bars) after feeding to 14 weeks or 20 weeks or 28 weeks of age on a chow-diet, and after feeding to 14 weeks of age on a high-fat diet. Data represents the mean±SEM of 3-8 mice per group. $^{H}p<0.05$ and $^{HH}p<0.01$ versus wild type mice.

When fed on a high-fat diet, the effect of PYY knockout to increase body weight was more marked, the difference being statistically significant in both male and female mice from 7 or 9 weeks of age onwards, respectively (FIG. 2c, FIG. 2d). In high fat-fed male and female $PYY^{-/-}$ mice, the increased body weight was associated with a significant increase in total body fat mass (FIG. 2g, FIG. 2h). Male $PYY^{-/-}$ mice fed a high fat diet showed a significant increase in the weight of the epididymal (gonadal) fat depot, and female $PYY^{-/-}$ mice fed a high fat diet showed a significant increase in the weight of inguinal, gonadal and mesenteric fat depots (Table 1).

Despite the increases in body mass in $PYY^{-/-}$ mice, there was no significant effect of PYY ablation on actual food intake, either under chow-fed or high fat-fed conditions (Table 1). We determined food intake as the amount of food removed from the hopper per day minus the amount of food that was spilled on the cage floor. When fed a chow diet, male and female $PYY^{-/-}$ mice spilled less food in their cage than wild type mice, which was significant in the females, but the amount of food actually eaten was not different from that of chow-fed wild type animals. When fed a high-fat diet, there was no significant difference between $PYY^{-/-}$ and wild type mice with respect to the amount of food taken from the food hopper, or the amount of food spilled on the cage floor, indicating that the amount of high fat diet eaten by $PYY^{-/-}$ mice was no different from wild types. When chow-fed or fat-fed animals were subject to a 24 hour fast, there was no difference between knockout and wild type mice with respect to the amount of food actually eaten in the first 24, 48, or 72 hours post fasting.

Water intake in the chow-fed male and female $PYY^{-/-}$ mice was significantly reduced compared to wild type mice suggesting a regulatory function for PYY in water homeostasis (Table 1). Consistent with a role of PYY in inhibiting gut motility, fecal weight was significantly increased in the male but not female $PYY^{-/-}$ mice fed on a chow diet (Table 1).

EXAMPLE 5

Effect of Reduced PYY Expression on Glucose Homeostasis

To determine whether PYY ablation affects serum insulin levels and glucose tolerance, in vivo glucose tolerance tests were performed. We performed these tests in chow fed animals at 13 and 20 weeks of age, and in high fat-fed animals at 13 weeks of age.

Figure 3A:
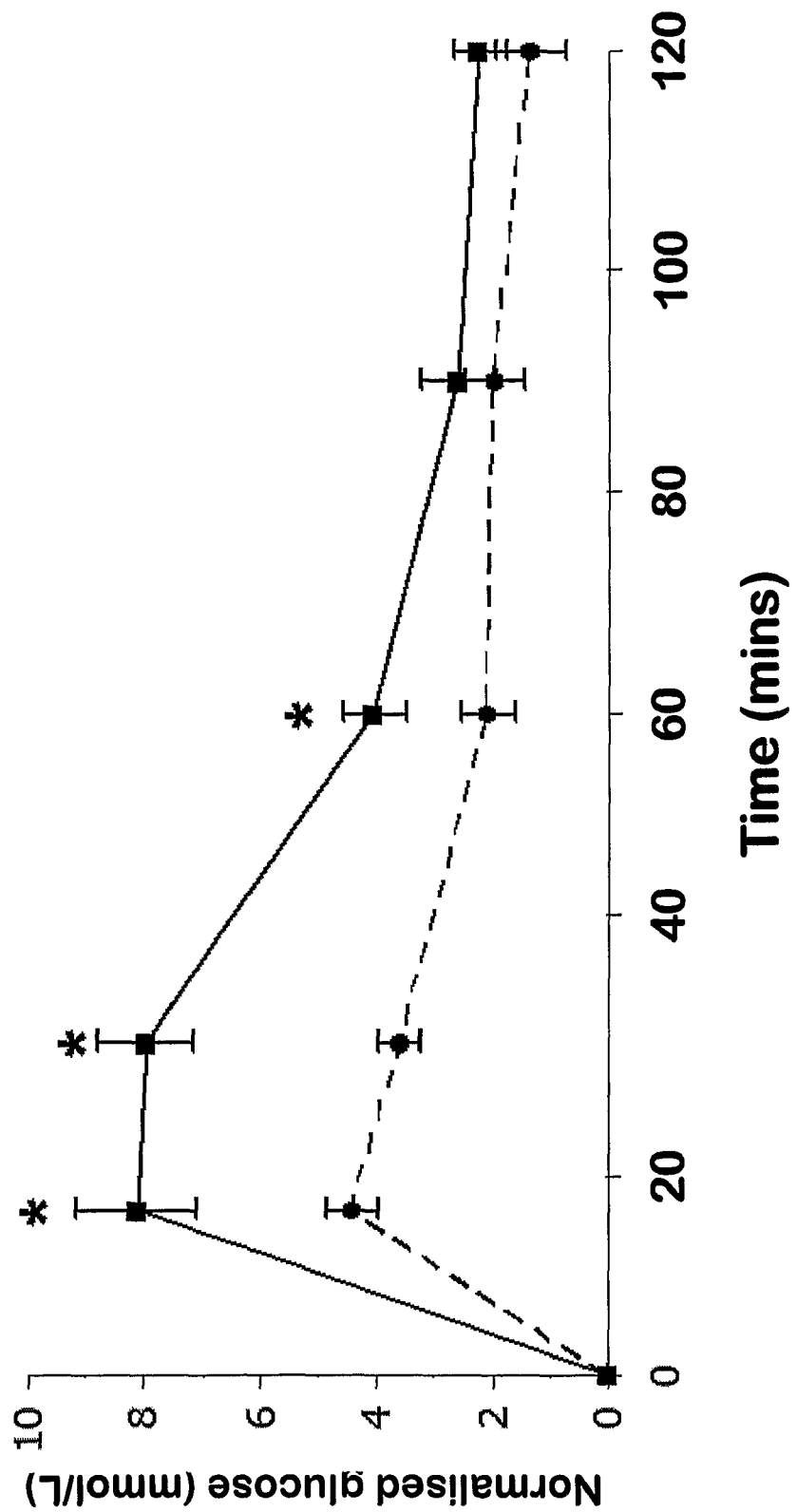
FIG. 3a is a graphical representation showing the effect of PYY deficiency on glucose homeostasis in males, as determined by a comparing serum glucose in 24 h-fasted chow-fed $PYY^{-/-}$ male mice (circles) and wild type male mice (squares) after intraperitoneal glucose injection (1.0 mg/kg). Data represent means±SEM of 7-8 mice per group. $^{H}p<0.05$ and $^{HH}p<0.01$ versus wild type mice.

In chow-fed animals, PYY deficiency improves glucose tolerance. In 13 week-old male chow-fed $PYY^{-/-}$ mice the peak in glycemia was significantly lower than that of wild type mice (FIG. 3a), and the area under the glucose response curve was significantly decreased compared to wild types (Table 1).

Even at 20 weeks of age, when the glucose tolerance of male wild type animals had noticeably deteriorated compared to 13 week-old wild types, the glucose tolerance of male $PYY^{-/-}$ mice was markedly and significantly improved compared to age-matched controls (Table 1).

Figure 3B:
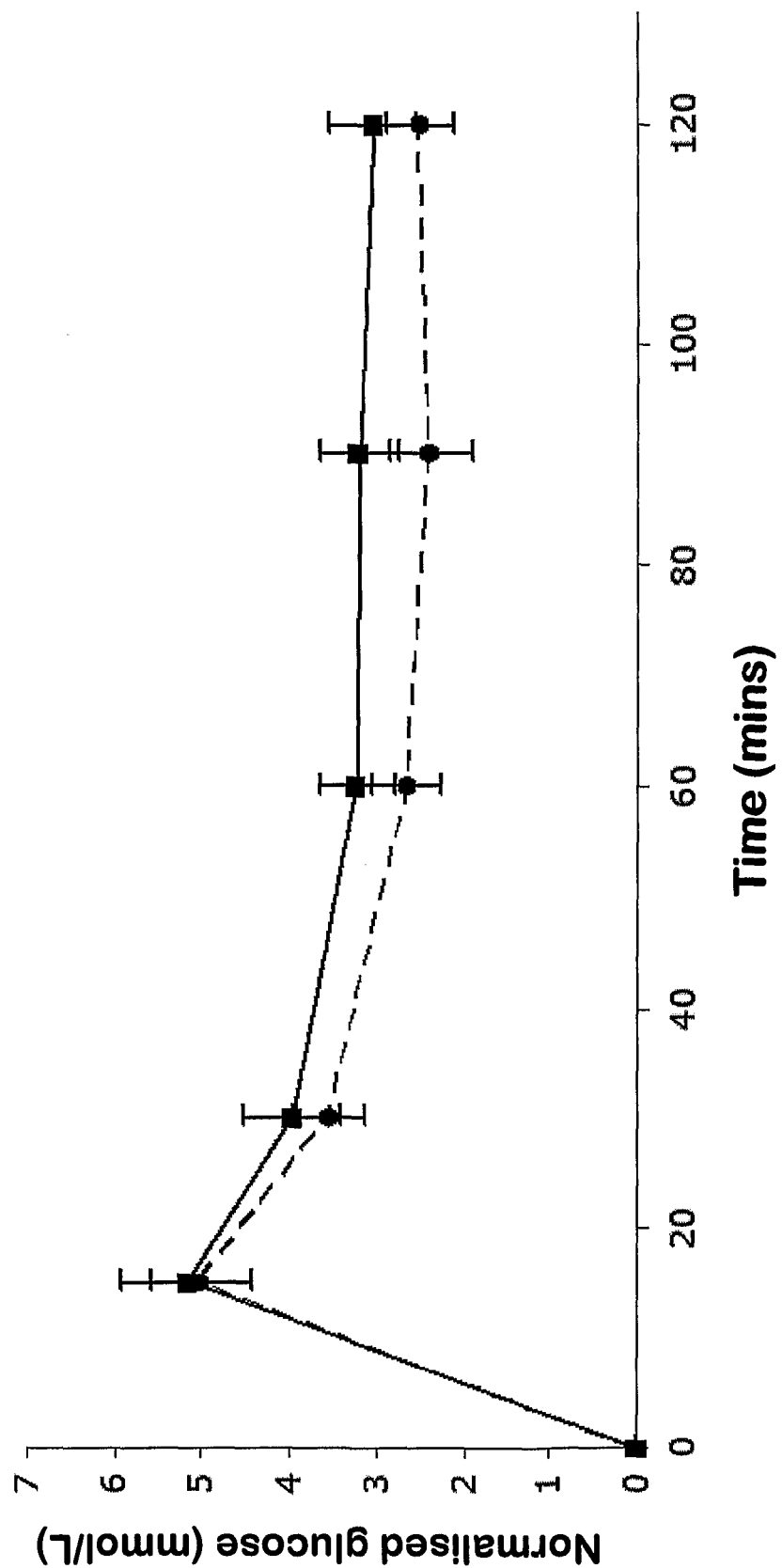
FIG. 3b is a graphical representation showing the effect of PYY deficiency on glucose homeostasis in females, as determined by a comparing serum glucose in 24 h-fasted chow-fed $PYY^{-/-}$ female mice (circles) and wild type female mice (squares) after intraperitoneal glucose injection (1.0 mg/kg). Data represent means±SEM of 7-8 mice per group. $^{H}p<0.05$ and $^{HH}p<0.01$ versus wild type mice.

A similar result was seen in 20 week-old female $PYY^{-/-}$ mice (Table 1), but with no difference in glucose tolerance at 13 weeks of age (FIG. 3b and Table 1).

Figure 3C:
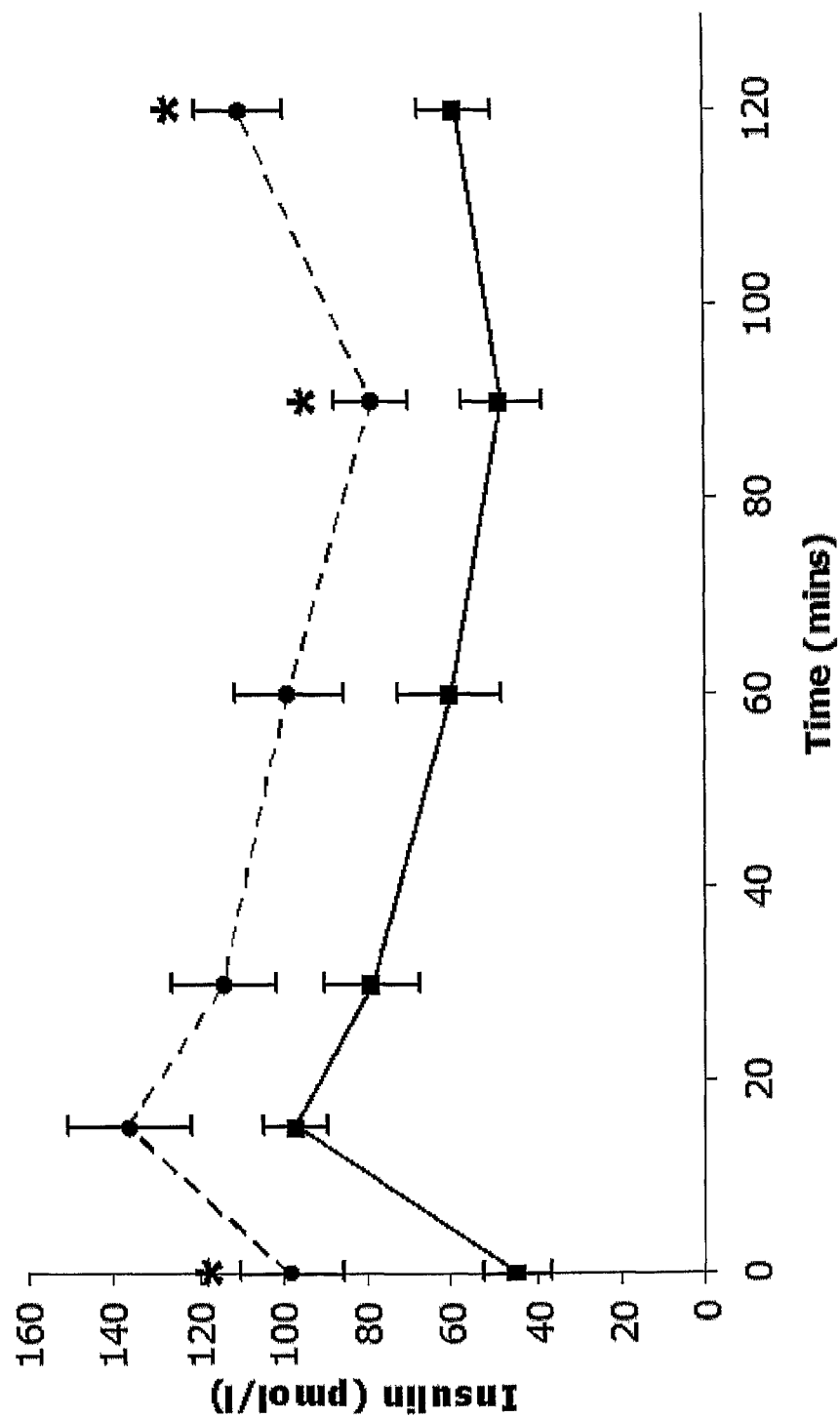
FIG. 3c is a graphical representation showing the effect of PYY deficiency on insulin homeostasis in males, as determined by a comparing serum insulin in 24 h-fasted chow-fed $PYY^{-/-}$ male mice (circles) and wild type male mice (squares) after intraperitoneal glucose injection (1.0 mg/kg). Data represent means±SEM of 7-8 mice per group. $^{H}p<0.05$ and $p<0.01$ versus wild type mice.
Figure 3D:
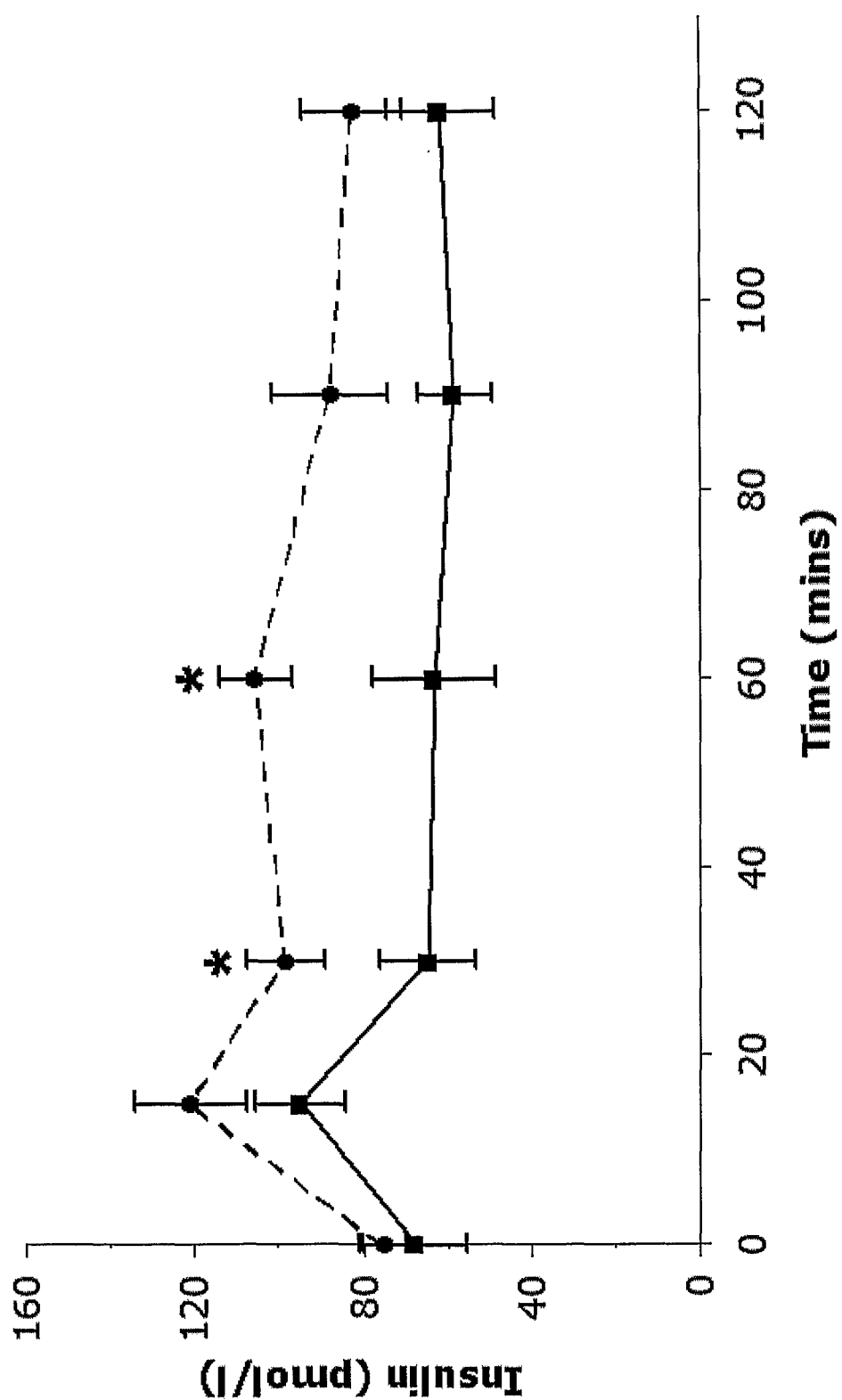
FIG. 3d is a graphical representation showing the effect of PYY deficiency on insulin homeostasis in females, as determined by a comparing serum insulin in 24 h-fasted chow-fed $PYY^{-/-}$ female mice (circles) and wild type female mice (squares) after intraperitoneal glucose injection (1.0 mg/kg). Data represent means±SEM of 7-8 mice per group. $^{H}p<0.05$ and $^{HH}p<0.01$ versus wild type mice.

In 13-week old chow-fed animals, the changes in glucose tolerance observed in $PYY^{-/-}$ mice were associated with significant increases in glucose-induced serum insulin levels (FIG. 3c, FIG. 3d). Moreover, male but not female $PYY^{-/-}$ mice had a significantly greater fasting serum insulin level than wild type controls (FIG. 3c, FIG. 3d). However by 20 weeks of age, the stimulatory effect of PYY deficiency on serum insulin levels was no longer observed, and the fasting or glucose-induced serum insulin levels of both male and female mice was not significantly different from that of wild type controls (data not shown). Therefore, the improved glucose tolerance of aged PYY$^{-/-}$ mice appears to be due to increased insulin sensitivity rather than increased insulin secretion.

Figure 3E:
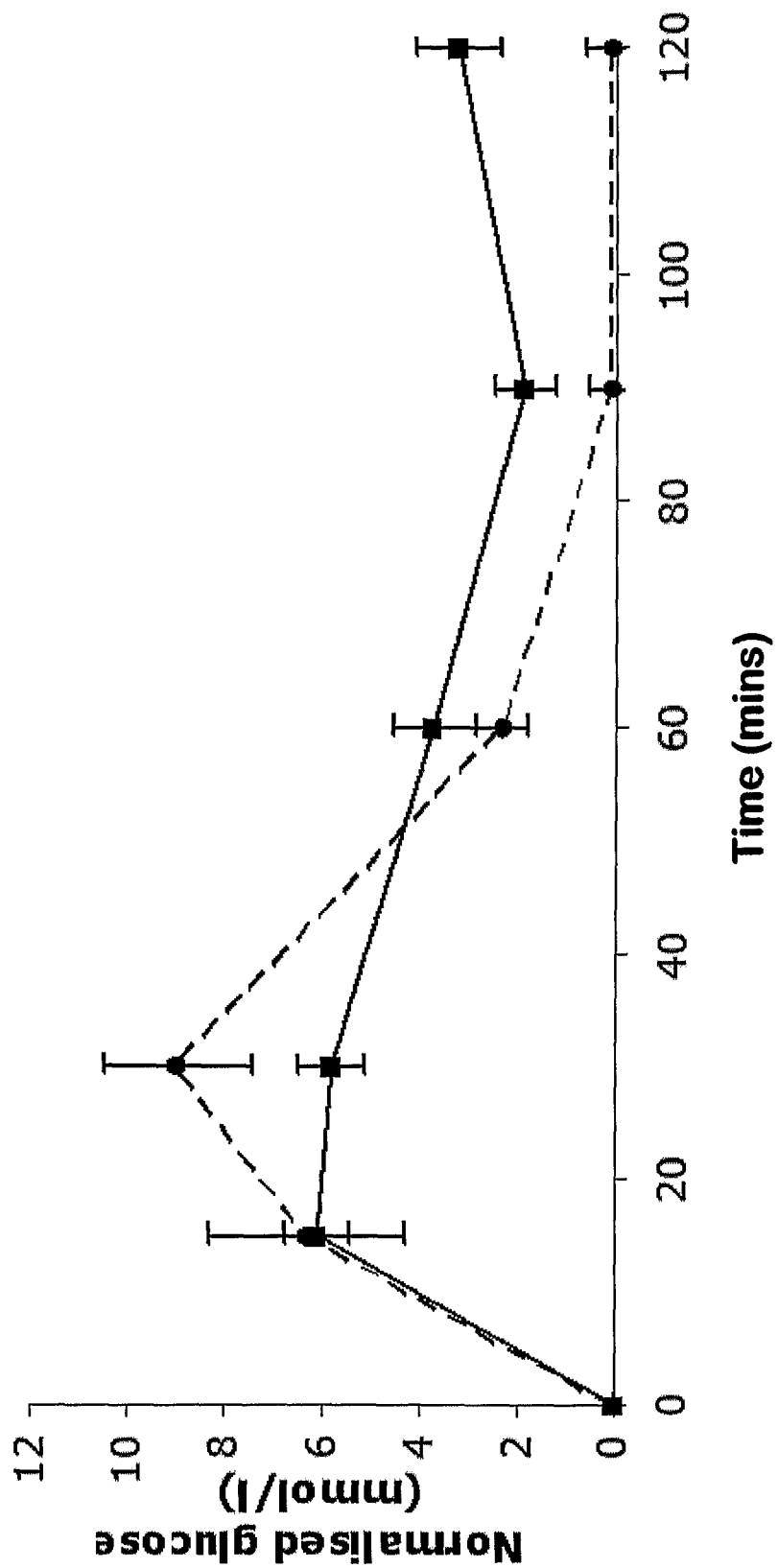
FIG. 3e is a graphical representation showing the effect of PYY deficiency on glucose homeostasis in males, as determined by a comparing serum glucose in 24 h-fasted high-fat-fed $PYY^{-/-}$ male mice (circles) and wild type male mice (squares) after intraperitoneal glucose injection (1.0 mg/kg). Data represent means±SEM of 7-8 mice per group. $^{H}p<0.05$ and $^{HH}p<0.01$ versus wild type mice.
Figure 3F:
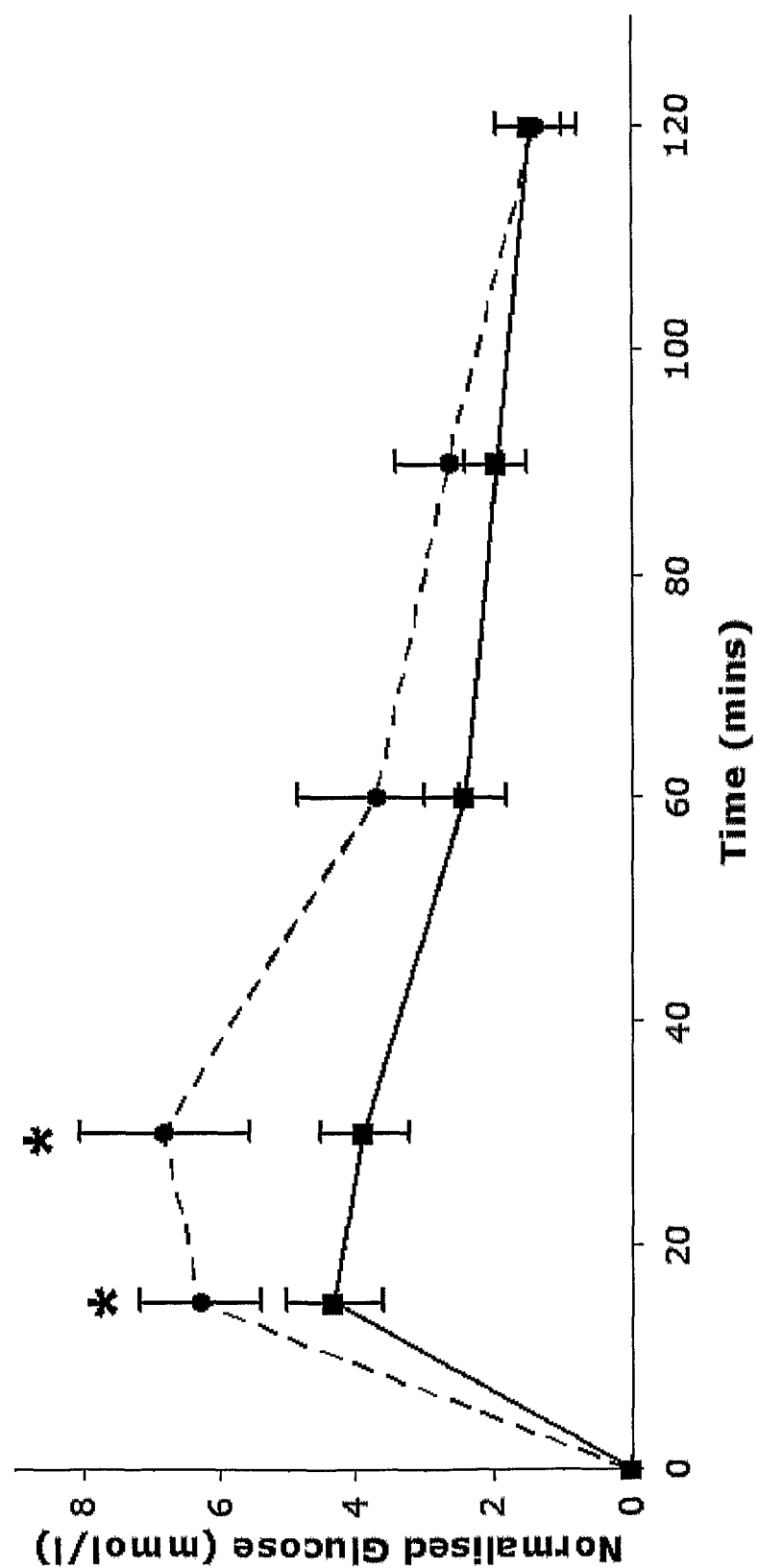
FIG. 3f is a graphical representation showing the effect of PYY deficiency on glucose homeostasis in females, as determined by a comparing serum glucose in 24 h-fasted high-fat-fed $PYY^{-/-}$ female mice (circles) and wild type female mice (squares) after intraperitoneal glucose injection (1.0 mg/kg). Data represent means±SEM of 7-8 mice per group. $^{H}p<0.05$ and $^{HH}p<0.01$ versus wild type mice.
Figure 3G:
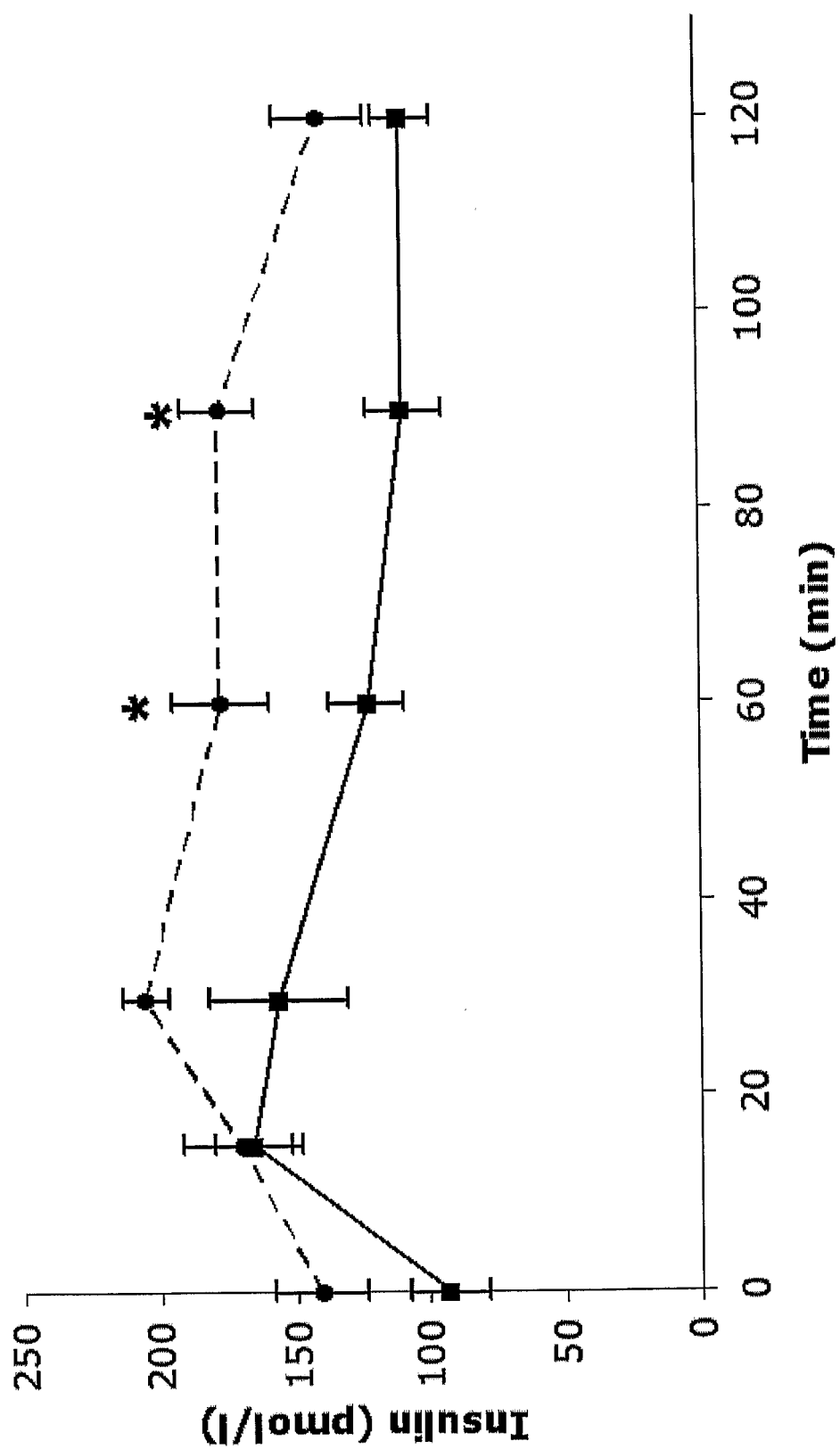
FIG. 3g is a graphical representation showing the effect of PYY deficiency on insulin homeostasis in males, as determined by a comparing serum insulin in 24 h-fasted high-fat-fed $PYY^{-/-}$ male mice (circles) and wild type male mice (squares) after intraperitoneal glucose injection (1.0 mg/kg). Data represent means±SEM of 7-8 mice per group. $^{H}p<0.05$ and $^{HH}p<0.01$ versus wild type mice.
Figure 3H:
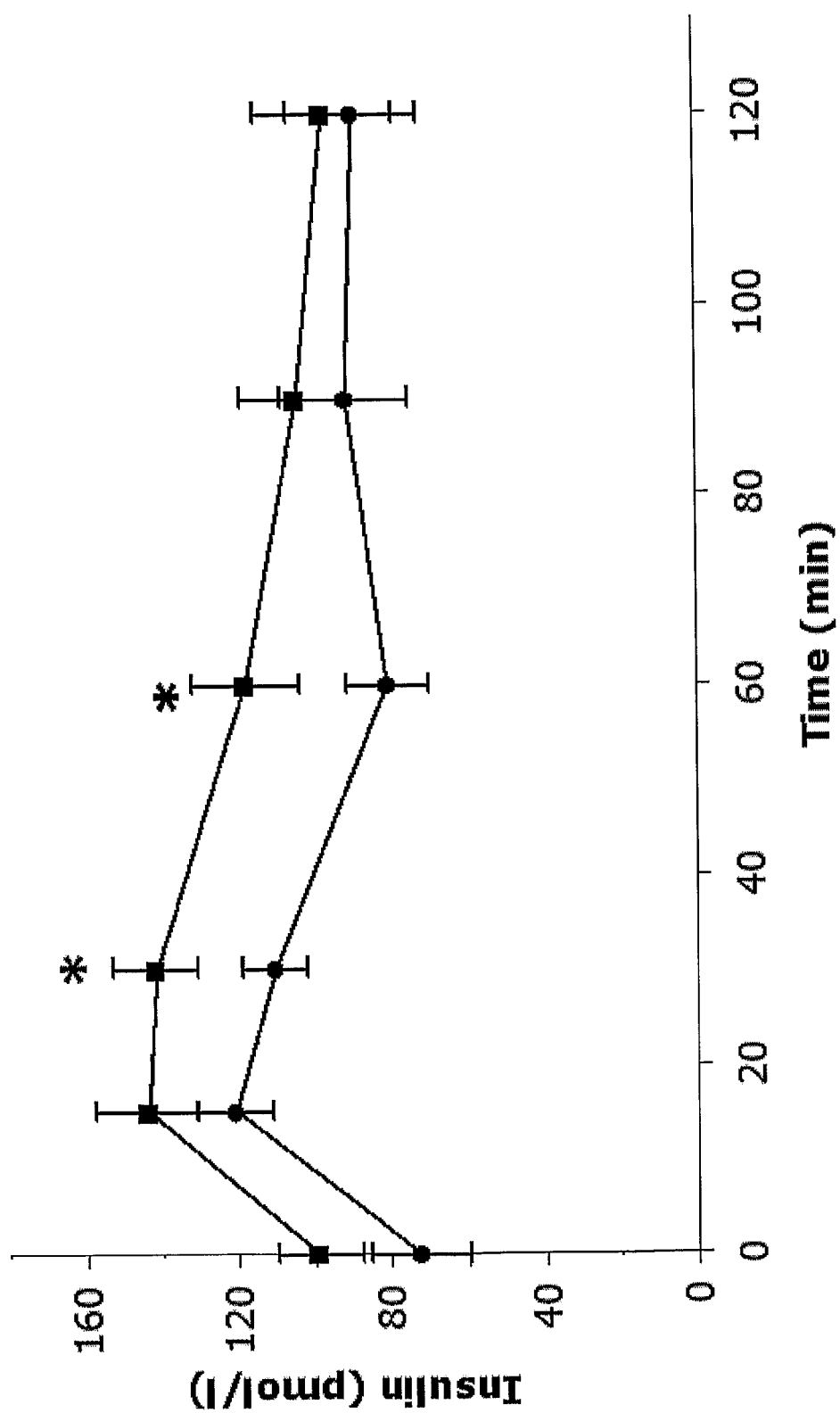
FIG. 3h is a graphical representation showing the effect of PYY deficiency on insulin homeostasis in females, as determined by a comparing serum insulin in 24 h-fasted high-fat-fed $PYY^{-/-}$ female mice (circles) and wild type female mice (squares) after intraperitoneal glucose injection (1.0 mg/kg). Data represent means±SEM of 7-8 mice per group. $^{H}p<0.05$ and $^{HH}p<0.01$ versus wild type mice.

Under conditions of high fat feeding, female but not male PYY$^{-/-}$ mice developed impaired glucose tolerance (FIG. 3f, FIG. 3h; Table 1). In female knockout mice these changes were associated with a significant decrease in glucose-induced serum insulin levels (FIG. 3h). Therefore the pronounced, 50% increase in adiposity in high fat-fed female PYY$^{-/-}$ mice was associated with glucose intolerance, and impaired glucose-induced insulin levels. No such phenotype was observed in the male high fat-fed knockouts, in which glucose tolerance were normal (FIG. 3e; Table 1), and glucose-induced serum insulin levels remained significantly greater than that of wild type control mice (FIG. 3g).

EXAMPLE 6

Effect of Reduced PYY Expression on Serum Hormone and Metabolite Concentrations In wild type mice, feeding a high fat diet resulted in significant increases in the serum concentrations of free fatty acids or triglycerides (FIG. 4a-d). Interestingly, this increase was not observed in fat-fed PYY$^{-/-}$ mice, in which the serum concentrations of these lipids were not significantly different from chow-fed knockout values (FIG. 4a-d). Indeed, serum levels of free fatty acids or triglycerides were significantly reduced in fat-fed PYY$^{-/-}$ versus high fat-fed wild types.

Figure 4A:
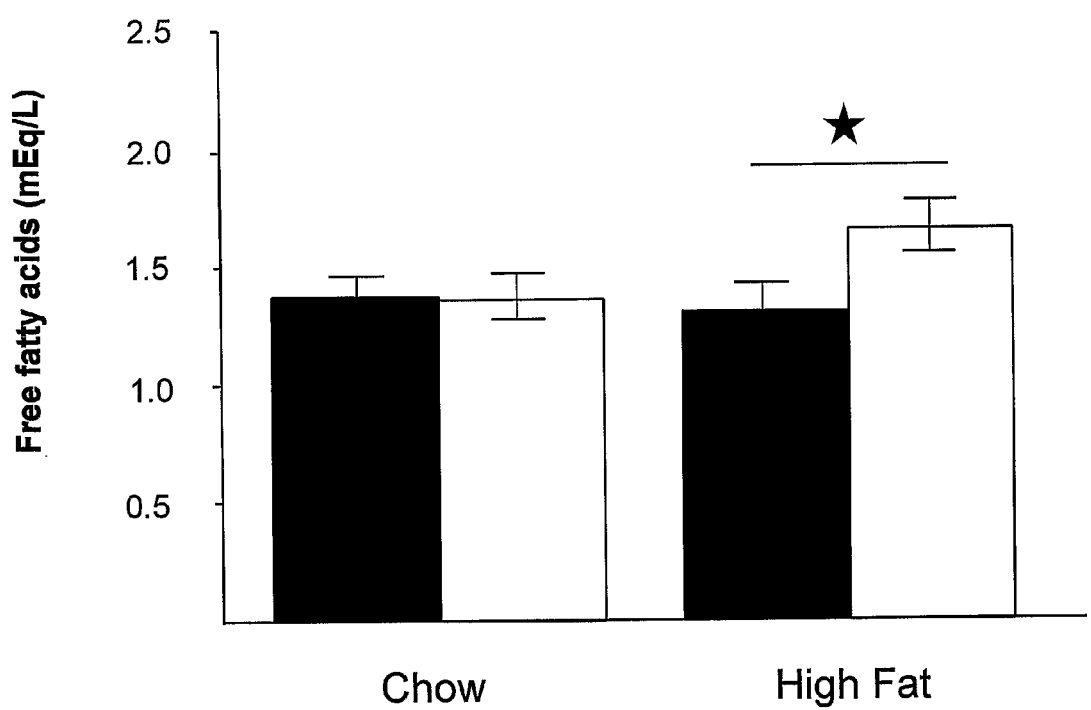
FIG. 4a is a graphical representation showing the effect of PYY deficiency on basal free fatty acid (FFA) levels in 14 week-old male $PYY^{-/-}$ mice (filled bars) and wild type mice (open bars) fed on a chow diet (left pair of bars) or high fat diet (right pair of bars). Data represent means±SEM of 8-12 mice per group. $^{H}p<0.05$, $p<0.01$, $^{HHH}p<0.001$ versus the comparison shown by horizontal bars.
Figure 4B:
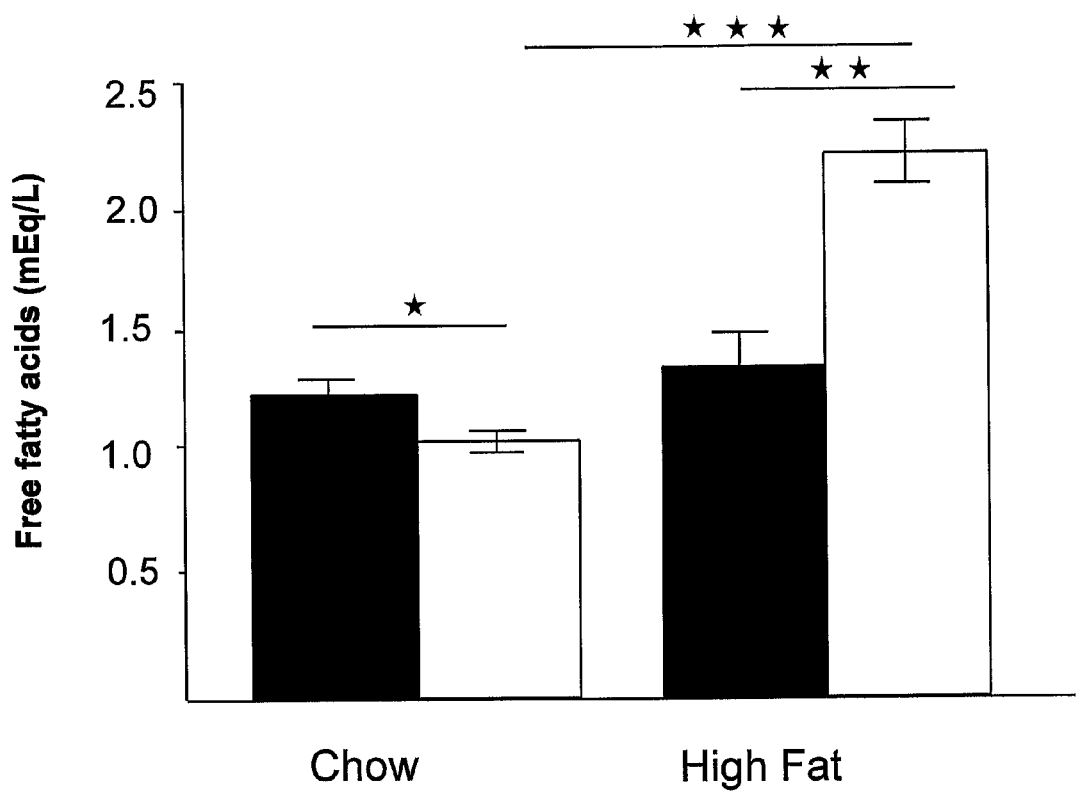
FIG. 4b is a graphical representation showing the effect of PYY deficiency on basal free fatty acid (FFA) levels in 14 week-old female PYY$^{-/-}$ mice (filled bars) and wild type female mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.
Figure 4C:
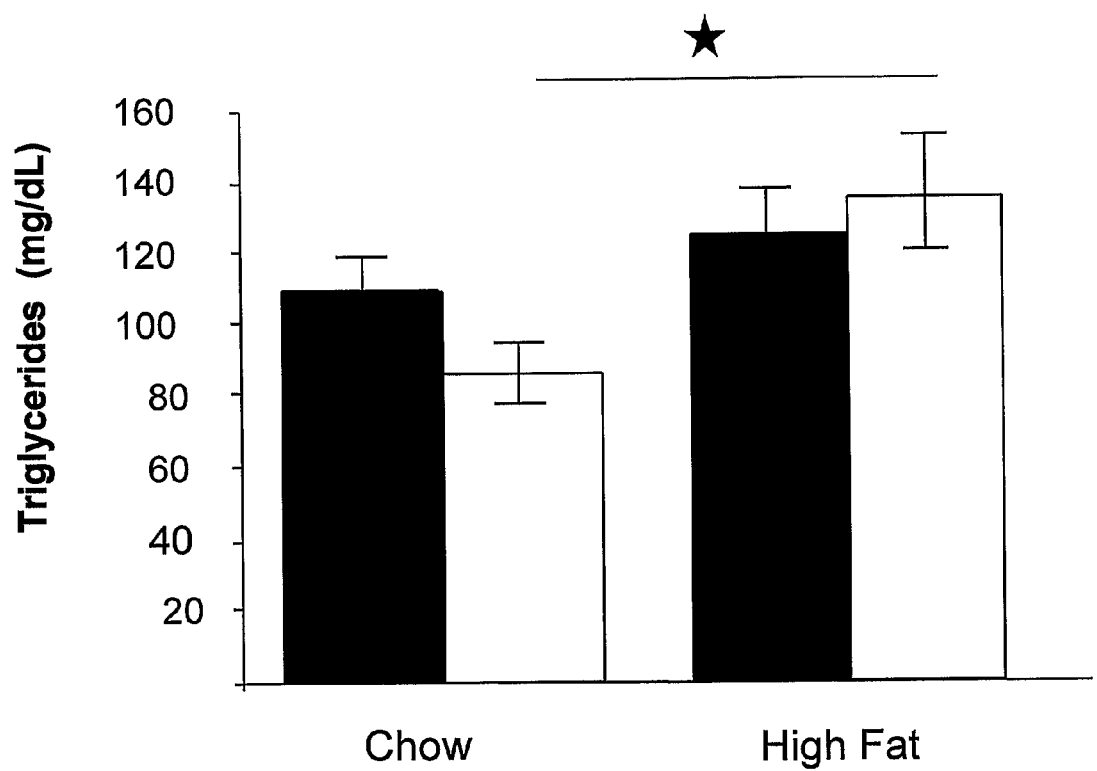
FIG. 4c is a graphical representation showing the effect of PYY deficiency on triglyceride levels in 14 week-old male PYY$^{-/-}$ mice (filled bars) and wild type mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.
Figure 4D:
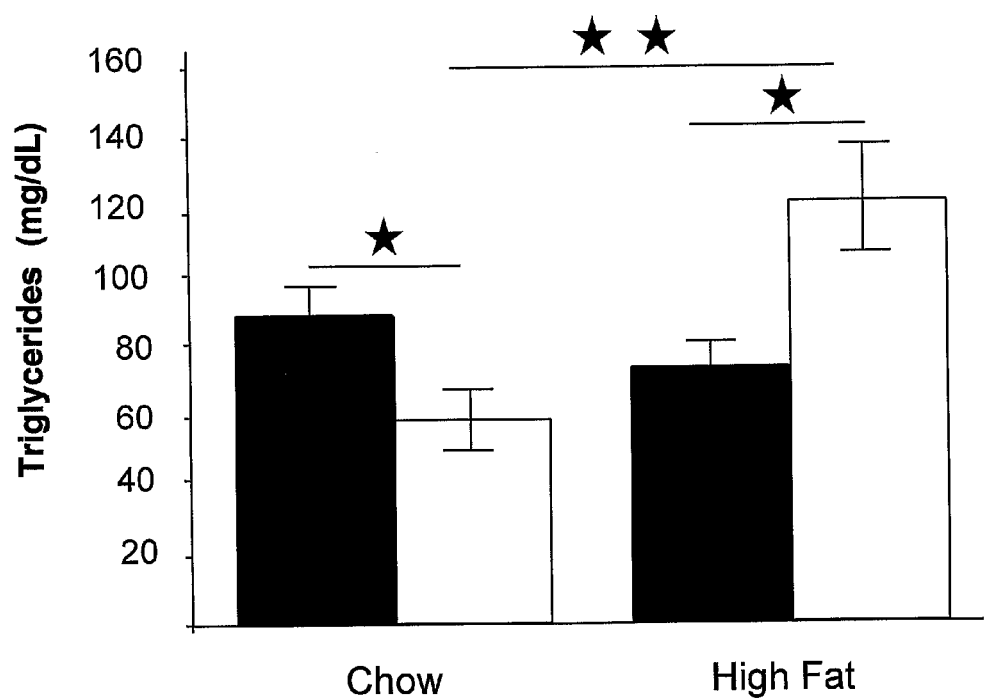
FIG. 4d is a graphical representation showing the effect of PYY deficiency on triglyceride levels in 14 week-old female PYY$^{-/-}$ mice (filled bars) and wild type female mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.
Figure 4E:
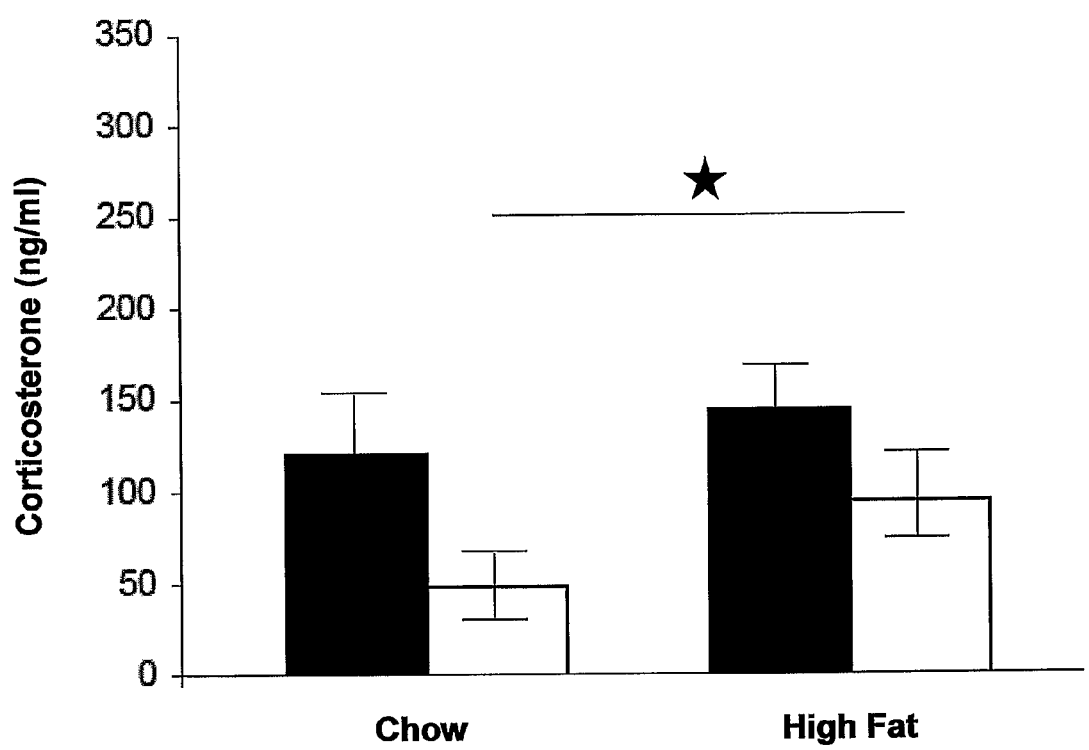
FIG. 4e is a graphical representation showing the effect of PYY deficiency on corticosterone levels in 14 week-old male PYY$^{-/-}$ mice (filled bars) and wild type mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.
Figure 4F:
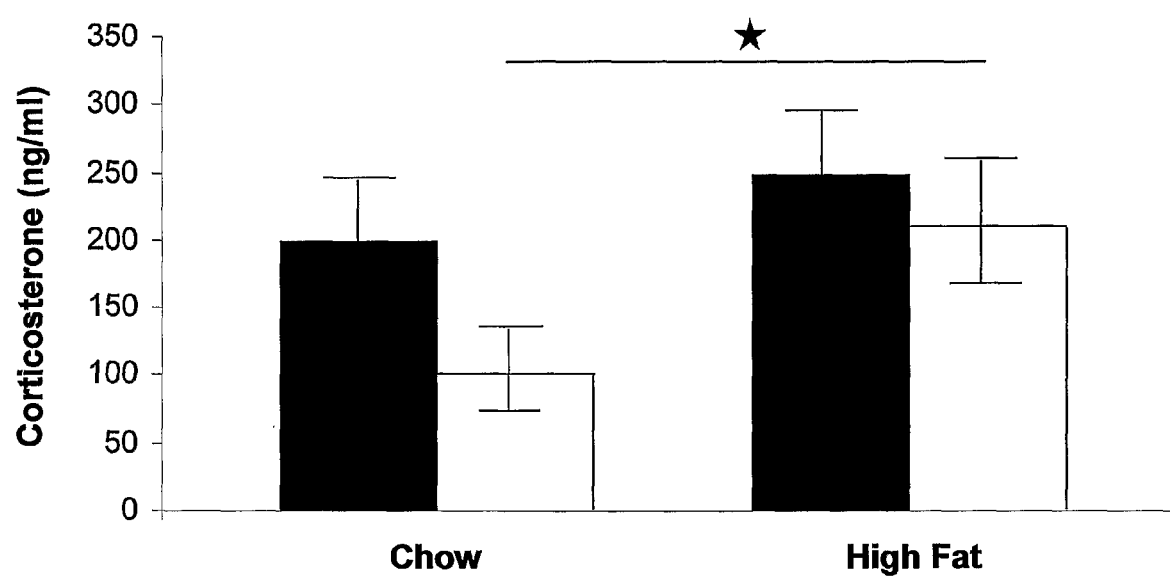
FIG. 4f is a graphical representation showing the effect of PYY deficiency on corticosterone levels in 14 week-old female PYY$^{-/-}$ mice (filled bars) and wild type female mice (open bars) fed on a chow diet (left pair of bars) or high fat diet (right pair of bars). Data represent means±SEM of 8-12 mice per group. $^{H}p<0.05$, $^{HH}p<0.01$, $^{HHH}p<0.001$ versus the comparison shown by horizontal bars.
Figure 4G:
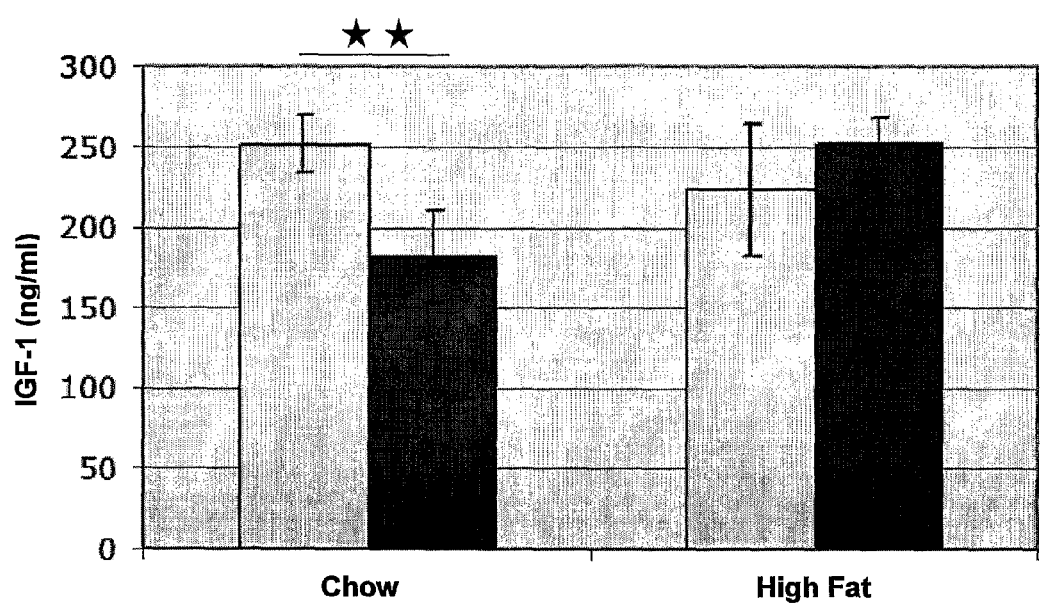
FIG. 4g is a graphical representation showing the effect of PYY deficiency on IGF-1 levels in 14 week-old male PYY$^{-/-}$ mice (filled bars) and wild type mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.

Under both chow- and fat-fed conditions, PYY$^{-/-}$ mice showed a tendency to increased serum levels of corticosterone, albeit the difference did not reach statistical significance (FIG. 4e-f). Interestingly, whereas wild type animals showed a significant increase in serum corticosterone levels in response to the high fat diet, this effect of fat feeding was not observed in PYY knockouts (FIG. 4 e-f).

Figure 4H:
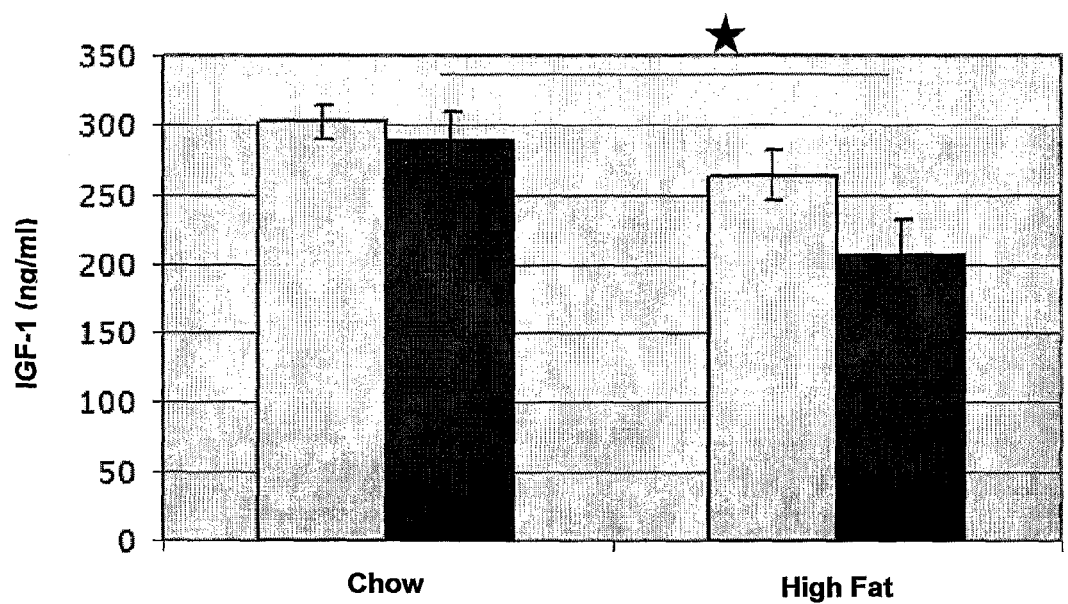
FIG. 4h is a graphical representation showing the effect of PYY deficiency on IGF-1 levels in 14 week-old female PYY$^{-/-}$ mice (filled bars) and wild type female mice (open bars) fed on a chow diet (left pair of bars) or high fat diet (right pair of bars). Data represent means±SEM of 8-12 mice per group. $^{H}p<0.05$, $^{HH}p<0.01$, $^{HHHH}p<0.001$ versus the comparison shown by horizontal bars.
Figure 4I:
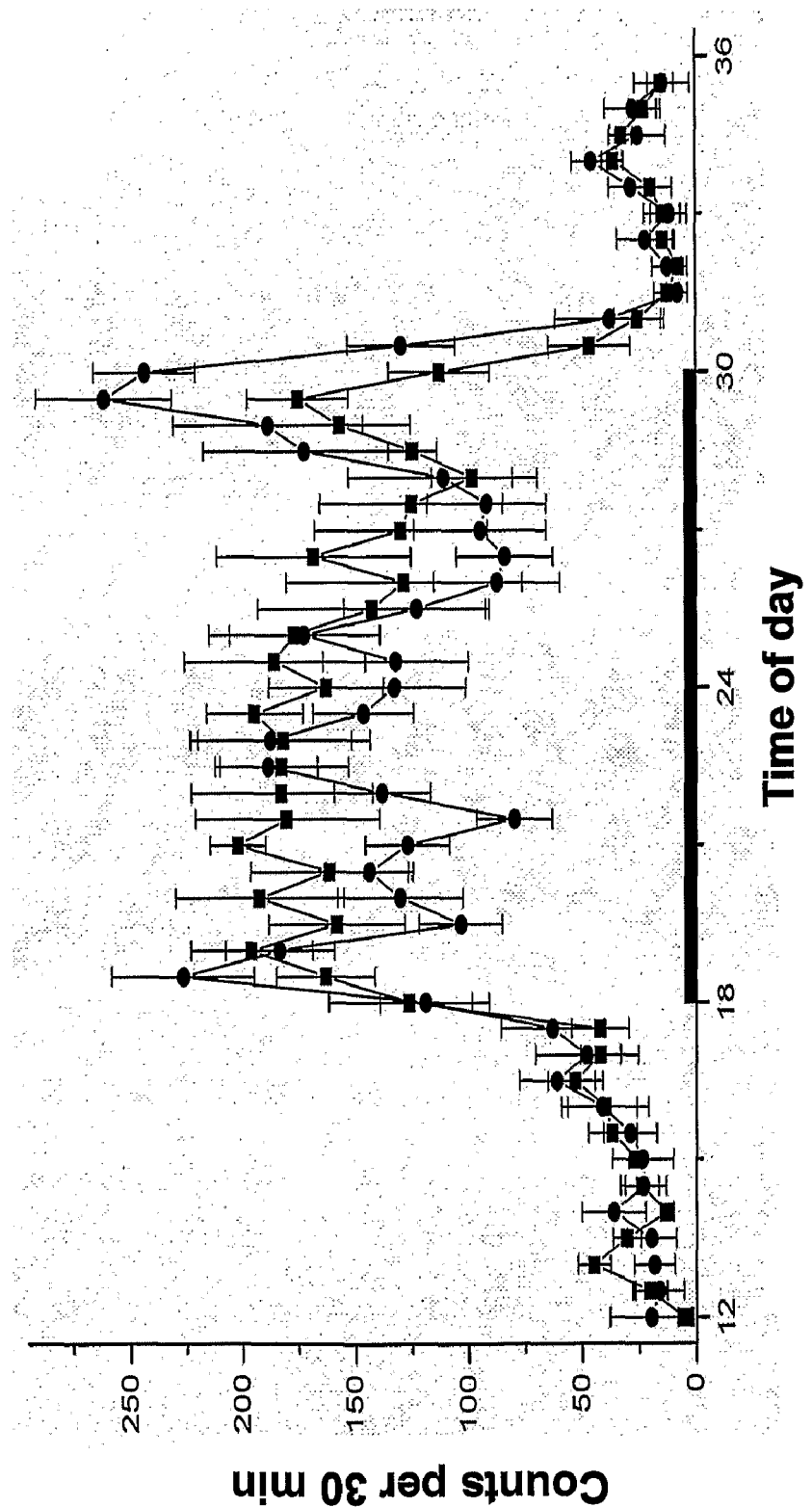
FIG. 4i is a graphical representation showing the 24-hour activity pattern of PYY$^{-/-}$ male mice (circles) and wild type male mice (squares). The dark bar on the x-axis represents night phase. Data represent means±SEM of 8-12 mice per group. $^{H}p<0.05$, $^{HHH}p<0.01$, $^{HHHH}p<0.001$ versus the comparison shown by horizontal bars.
Figure 4J:
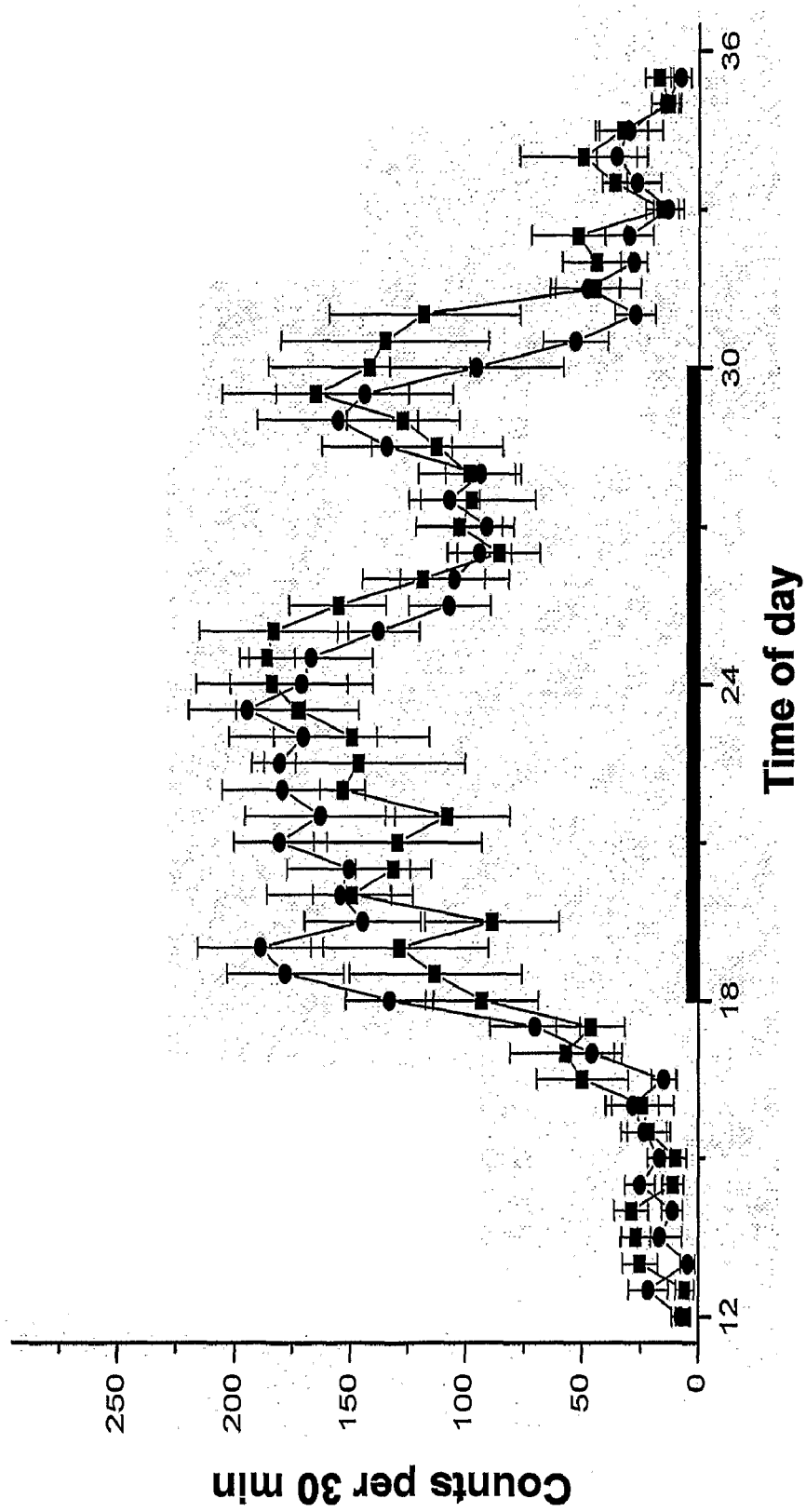
FIG. 4j is a graphical representation showing the 24-hour activity pattern of PYY$^{-/-}$ female mice (circles) and wild type female mice (squares). The dark bar on the x-axis represents night phase. Data represent means±SEM of 8-12 mice per group. $^{H}p<0.05$, $^{HH}p<0.01$, $^{HHHH}p<0.001$ versus the comparison shown by horizontal bars.

Since PYY knockout increases lean mass in male and female animals (FIG. 2 e-f), we investigated serum concentrations of IGF-1, the main mediator of the growth effects of growth hormone. Indeed, serum IGF-1 levels were significantly increased in male PYY$^{-/-}$ mice under chow-fed but not high fat-fed conditions (FIG. 4g), consistent with the pattern of change in total body lean mass (FIG. 2e). There was no significant effect of PYY deficiency on serum IGF-1 levels in female mice (FIG. 4h).

Serum concentrations of testosterone were increased in male PYY$^{-/-}$ mice both under chow-fed and fat-fed conditions, and the difference attained statistical significance in the chow-fed animals (Table 1).

Serum levels of leptin were not influenced by PYY ablation in 14-week old chow-fed male and female PYY$^{-/-}$ mice, but on a high fat diet male knockouts showed a significant increase in serum leptin levels compared to wild type counterparts (Table 1).

There was no significant effect of PYY deletion on serum glucagon concentrations (Table 1), consistent with the observation that our PYY knockout did not alter the morphology or number of glucagon-staining beta-cells in the islets of Langerhans (FIG. 1d, panels (vii) and (viii)).

As an index of hypothalamo-pituitary-thyroid function (which is an important determinant of resting metabolic rate), serum free T4 levels were measured in PYY and wild type mice. There was no significant effect of PYY knockout on serum free T4 levels in PYY$^{-/-}$ mice of either gender or dietary condition. However, there was a significant reduction in body temperature in chow-fed female PYY$^{-/-}$ mice (Table 1), potentially contributing to the development of obesity.

Analysis of the weight (as a percentage of body weight) of different tissues revealed a significant increase in liver weight in male PYY$^{-/-}$ mice compared to wild types (Table 1). Significant changes of other PYY-associated gastrointestinal tissue weights and sizes in PYY$^{-/-}$ mice are summarized in Table 1.

EXAMPLE 7

Effects of Reduced PYY Expression on Motor Activity

To investigate whether PYY deficiency might affect energy expenditure due to physical activity, mice were tested for general activity as well as for different motor activity tasks over a period of 14 days. Our data indicate that 14-16 week-old male and female PYY$^{-/-}$ and wild type mice are indistinguishable in the amount and pattern of activity (FIG. 4 i-j). Furthermore, motor activity assessed in the open field test was not different between male and female PYY$^{-/-}$ and wild type mice, suggesting that locomotion is not altered in these mice.

EXAMPLE 8

Effects of Reduced PYY Expression on Hypothalamic Neuropeptide mRNA Expression To assess possible central mechanisms for changes in energy homeostasis in PYY$^{-/-}$ mice, we analyzed the expression of neuropeptides known to regulate energy balance such as NPY, proopiomelanocortin (POMC), and growth-hormone releasing hormone (GHRH) in the hypothalamus of these mice. As there was a significant effect of PYY ablation on water intake, we also measured the expression of vasopressin (VP).

Figure 5:
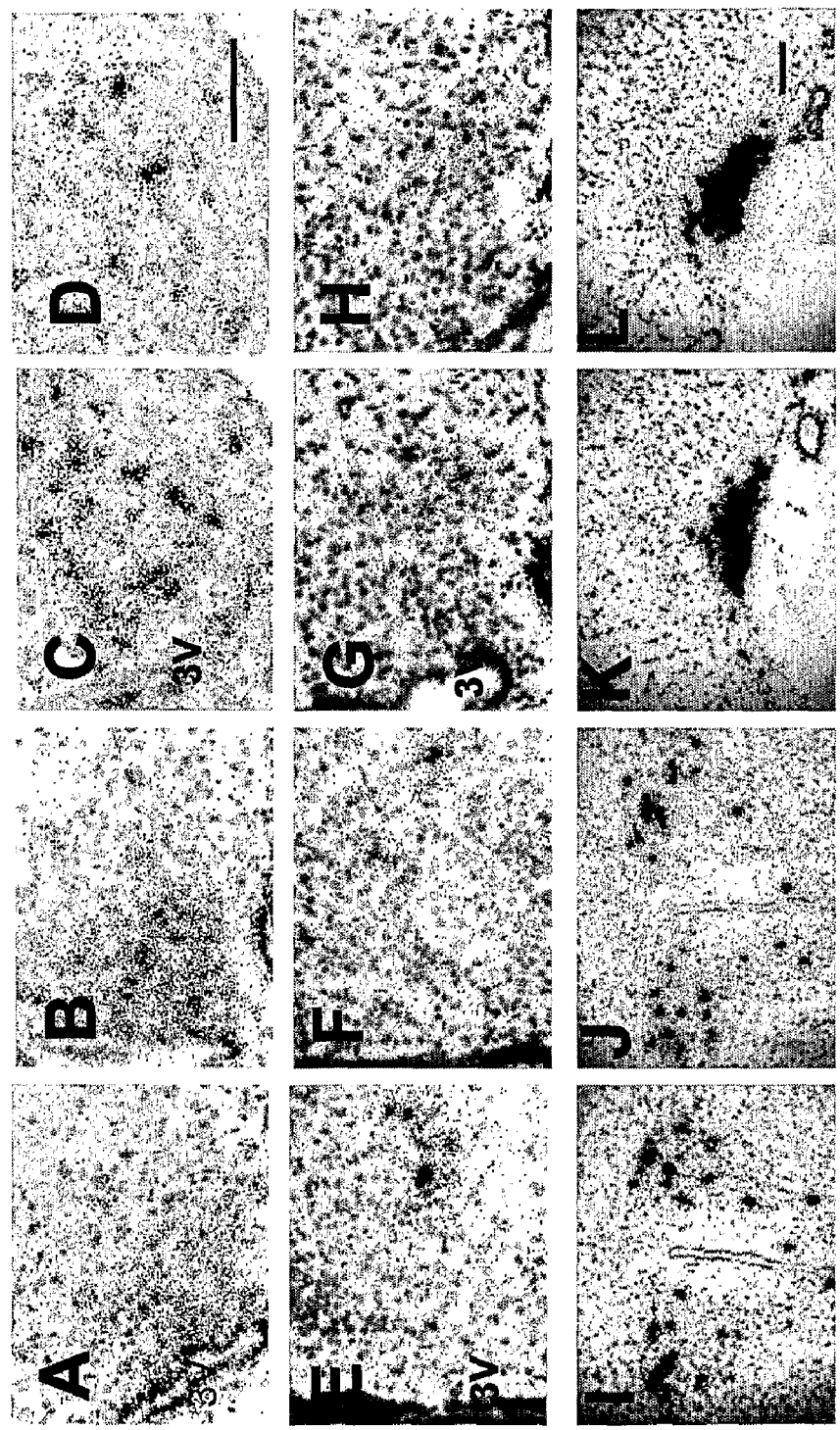
FIG. 5a is a copy of a photographic representation showing the effect of PYY deletion on NPY expression in the arcuate hypothalamic nucleus, as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 µm.
FIG. 5b is a copy of a photographic representation showing the effect of PYY deletion on NPY expression in the arcuate hypothalamic nucleus, as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 µm.
FIG. 5c is a copy of a photographic representation showing the effect of PYY deletion on POMC expression in the arcuate hypothalamic nucleus, as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 µm.
FIG. 5d is a copy of a photographic representation showing the effect of PYY deletion on POMC expression in the arcuate hypothalamic nucleus, as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 µm.
FIG. 5e is a copy of a photographic representation showing the effect of PYY deletion on GHRH expression in the ventromedial nucleus, as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 µm.
FIG. 5f is a copy of a photographic representation showing the effect of PYY deletion on GHRH expression in the ventromedial nucleus, as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 µm.
FIG. 5g is a copy of a photographic representation showing the effect of PYY deletion on GHRH expression in the arcuate hypothalamic nucleus, as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 µm.
FIG. 5h is a copy of a photographic representation showing the effect of PYY deletion on GHRH expression in the arcuate hypothalamic nucleus, as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 µm.
FIG. 5i is a copy of a photographic representation showing the effect of PYY deletion on vasopressin expression in the paraventricular nucleus, as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 μm.
FIG. 5j is a copy of a photographic representation showing the effect of PYY deletion on vasopressin expression in the paraventricular nucleus, as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 μm.
FIG. 5k is a copy of a photographic representation showing the effect of PYY deletion on vasopressin expression in the supraoptic nucleus (SON), as determined by measuring mRNA levels in the hypothalamus of 14 week-old PYY$^{-/-}$ male mice by in situ hybridization. Data show high-power bright-field photomicrographs of dipped sections obtained from wild type and PYY$^{-/-}$ mice after in-situ hybridization. Scale bars=10 μm.
FIG. 5l is a copy of a photographic representation showing the effect of PYY deletion on vasopressin expression in the supraoptic nucleus (SON), as determined by measuring mRNA levels in the hypothalamus of 14 week-old wild type male mice by in situ hybridization. Data show high-power bright-field photomicrographs of dipped sections obtained from wild type and PYY$^{-/-}$ mice after in-situ hybridization. Scale bars=10 μm.

14 week-old male PYY$^{-/-}$ mice show a significant 21% reduction in NPY and a significant 25% increase in POMC mRNA expression levels in the arcuate nucleus compared to wild types (FIG. 5, a-d; Table 2). Interestingly, these changes were not associated with reductions in food intake. The mRNA expression of the growth-promoting neuropeptide, GHRH, was unaltered in the arcuate nucleus, but showed a significant increase in the ventro-medial hypothalamic nucleus (VMH) of PYY$^{-/-}$ mice, consistent with an activation of the somatotropic axis and the significantly higher serum levels of IGF-1 (Table 1) and increased lean mass (FIG. 2e) in the chow-fed male PYY$^{-/-}$ mice (FIG. 5, e-h). Vasopressin mRNA levels in the PVN and superoptic nuclei (SON) did not change in the PYY$^{-/-}$ mice, indicating that other mechanisms are responsible for the observed decrease in water intake (FIG. 5, Table 2).

EXAMPLE 9

Effects of Reduced PYY Expression on Bone Mineral Density and Bone Mineral Content To assess possible effects of changing PYY expression on bone development and/or bone density and/or bone remodeling and/or bone growth, we determined the bone mineral density and bone mineral content of male and female mice having either wild-type PYY expression or alternatively, a disrupted PYY gene that ablates PYY expression.

Figure 6:
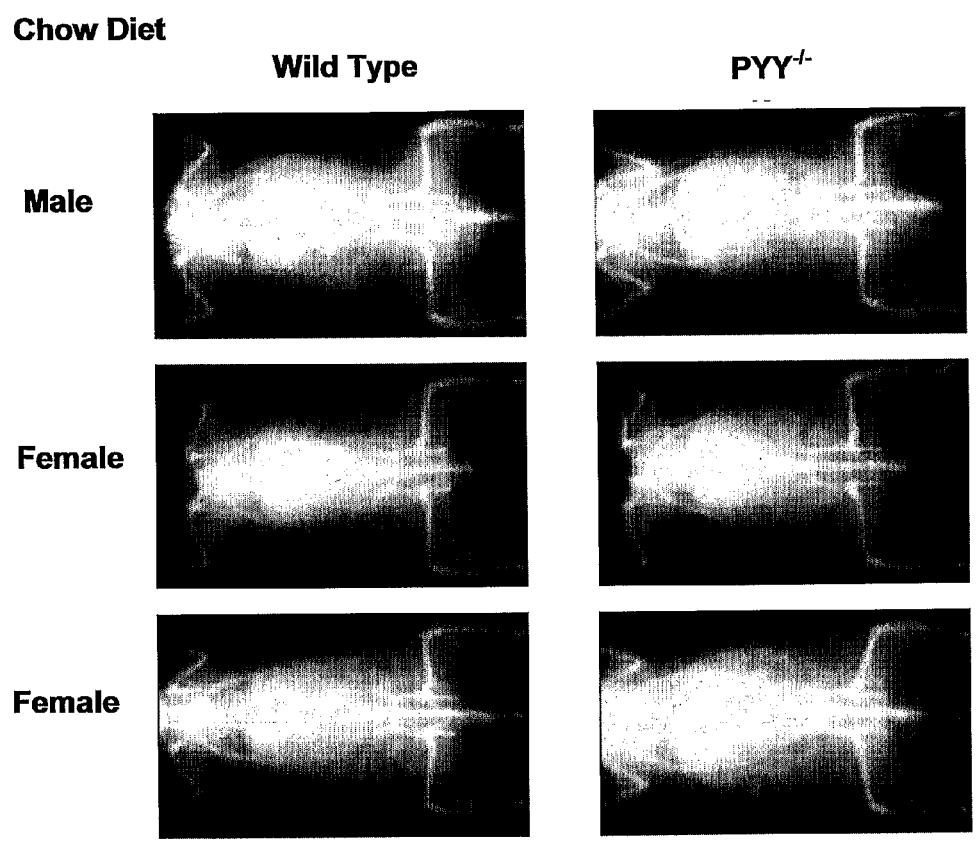
FIG. 6 provides photographic representations of dual energy X-ray absorptiometry (DXA) showing fat and bone content and density of male and female mice fed on a chow diet, wherein the mice have either wild type PYY gene expression, or comprising a deletion in their endogenous PYY gene (PYY$^{-/-}$).
Figure 7:
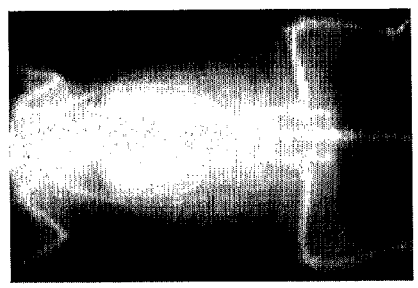
FIG. 7 provides photographic representations of dual energy X-ray absorptiometry (DXA) showing fat and bone content and density of male and female mice fed on a high fat diet, wherein the mice have either wild type PYY gene expression, or comprising a deletion in their endogenous PYY gene (PYY$^{-/-}$).
Figure 7:
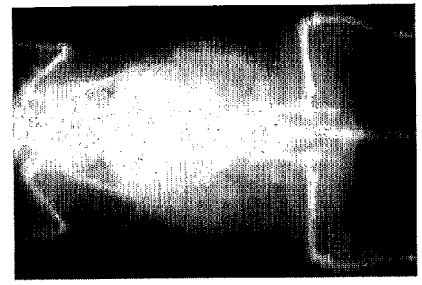
Figure 7:
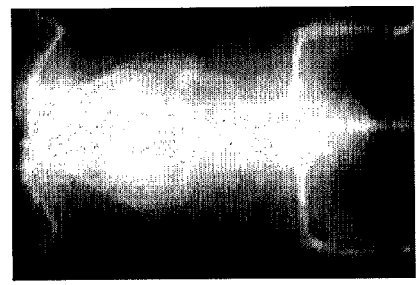
Figure 7:
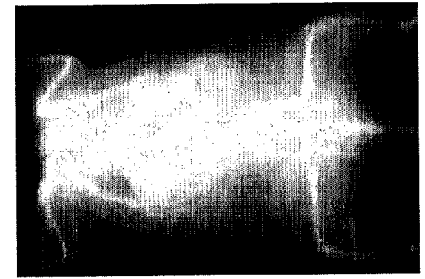
Figure 8:
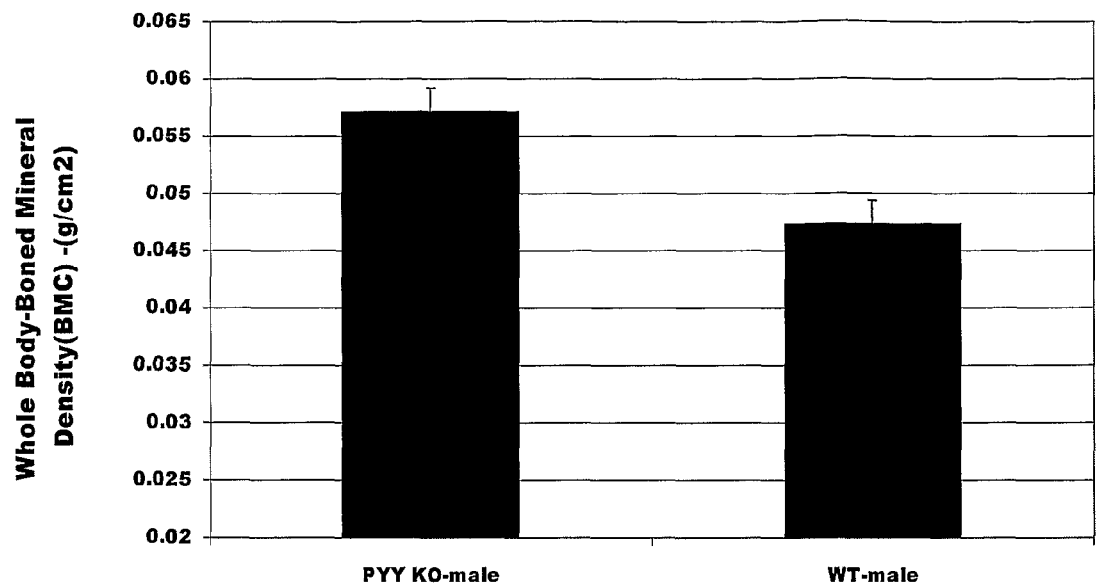
FIG. 8 is a graphical representation showing whole body mineral density (BMD) for male mice having either wild type PYY gene expression, or comprising a deletion in their endogenous PYY gene (PYY$^{-/-}$). Data show significantly higher bone mineral density for PYY knockout animals compared to wild type animals (P<0.003).
Figure 9:
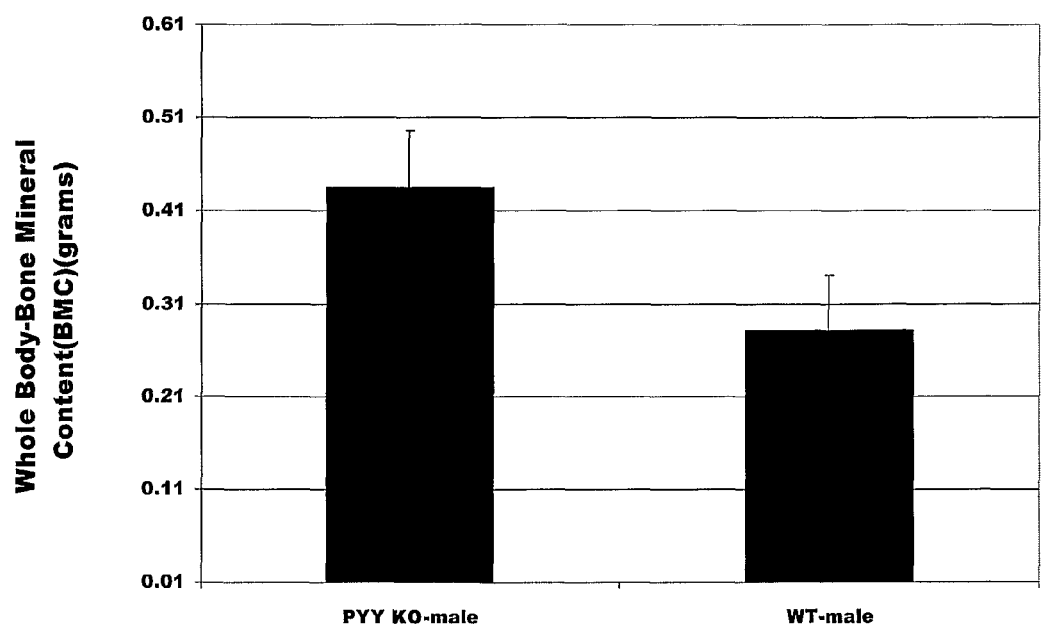
FIG. 9 is a graphical representation showing whole body mineral content (BMC) for male mice having either wild type PYY gene expression, or comprising a deletion in their endogenous PYY gene (PYY$^{-/-}$). Data show significantly higher bone mineral content for PYY knockout animals compared to wild type animals (P<0.002).
Figure 10:
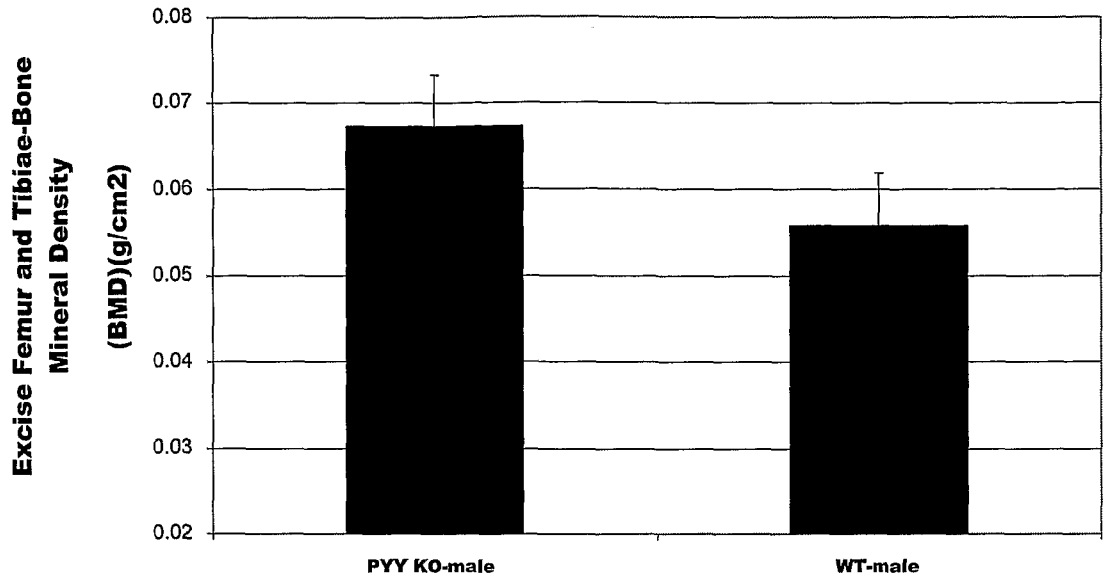
FIG. 10 is a graphical representation showing bone mineral density (BMD) of excised femurs and tibiae for male mice having have either wild type PYY gene expression, or comprising a deletion in their endogenous PYY gene (PYY$^{-/-}$). Data show comparable BMD for PYY knockout animals and to wild type animals.
Figure 11:
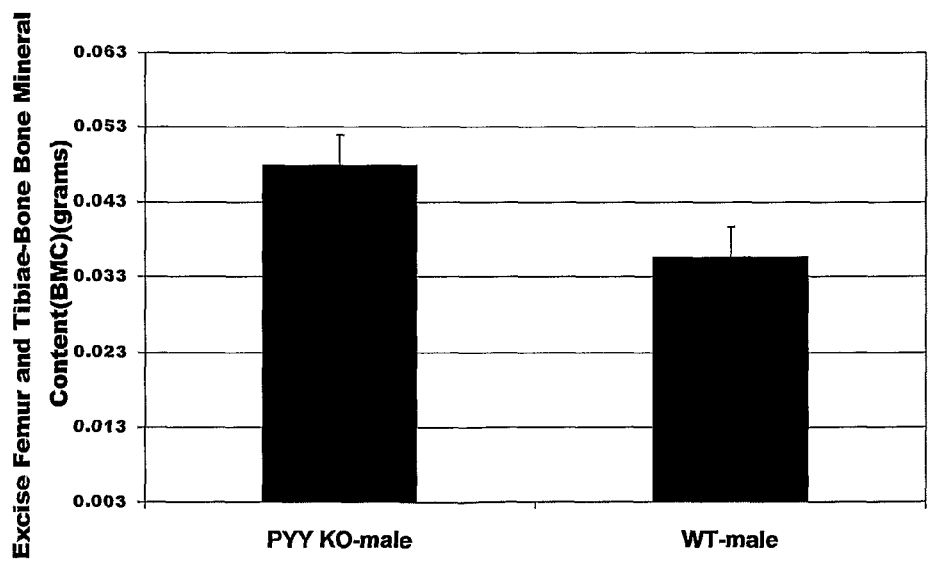
FIG. 11 is a graphical representation showing bone mineral content (BMC) of excised femurs and tibiae for male mice having have either wild type PYY gene expression, or comprising a deletion in their endogenous PYY gene (PYY$^{-/-}$). Data show comparable BMC for PYY knockout animals and to wild type animals.
Figure 12:
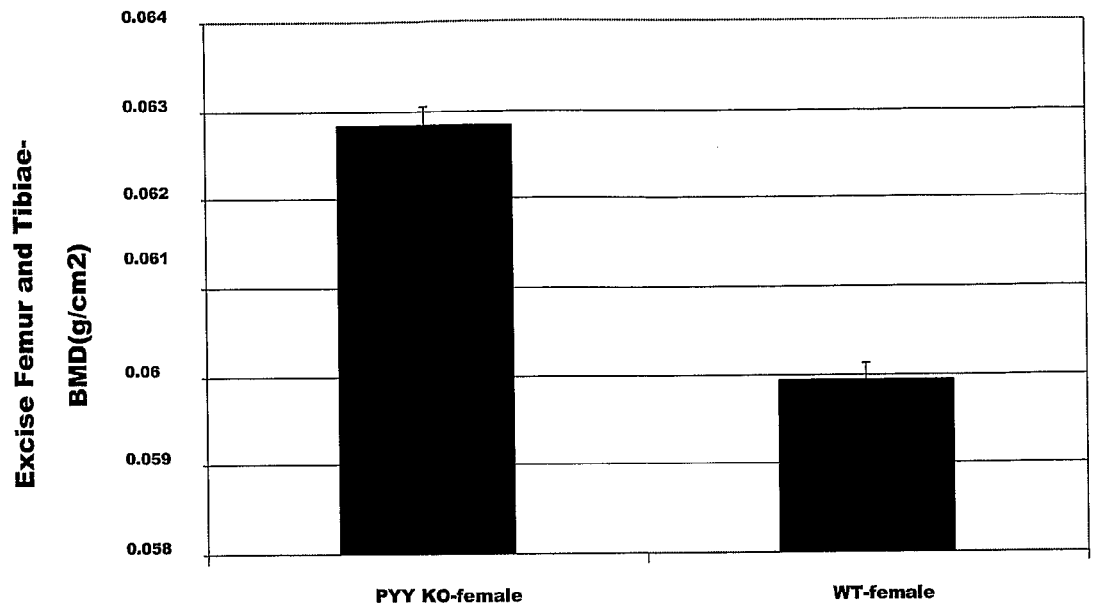
FIG. 12 is a graphical representation showing bone mineral density (BMD) of excised femurs and tibiae for female mice having have either wild type PYY gene expression, or comprising a deletion in their endogenous PYY gene (PYY$^{-/-}$). Data show higher BMD for PYY knockout animals and to wild type animals.
Figure 13:
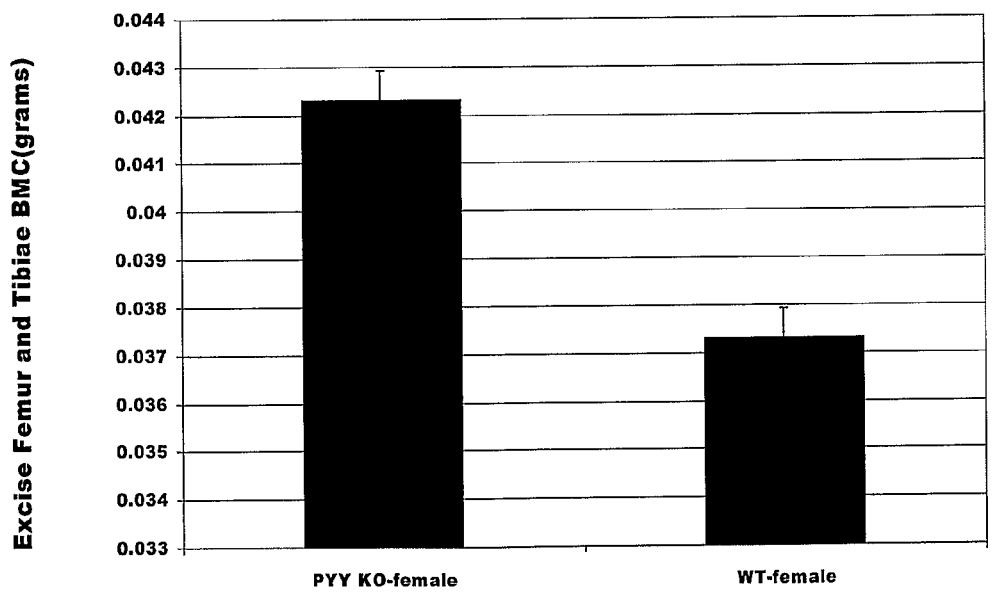
FIG. 13 is a graphical representation showing bone mineral content (BMC) of excised femurs and tibiae for female mice having have either wild type PYY gene expression, or comprising a deletion in their endogenous PYY gene (PYY$^{-/-}$). Data show higher BMC for PYY knockout animals and to wild type animals.

Data presented in FIGS. 6 and 7 show that male PYY$^{-/-}$ mice maintained on a chow diet show a higher bone density and fat content when compared to similarly-fed wild type male and female animals, as determined by whole body DXA. Similarly, whole body bone mineral density and whole body bone mineral content are elevated in male PYY$^{-/-}$ mice compared to their wild-type counterparts (FIGS. 8 and 9). In contrast, there were no apparent differences in bone mineral density or bone mineral content of excised tibiae and femurs of male PYY$^{-/-}$ and wild type animals (FIGS. 10 and 11).

In females, there is no apparent difference between whole body bone mineral density and whole body bone mineral content of PYY$^{-/-}$ mice compared to wild-type mice, however there is a noticeable tendency for PYY$^{-/-}$ mice to have elevated bone mineral density and bone mineral content of their femurs and tibiae (FIGS. 6, 7, 12 and 13).

EXAMPLE 10

Implications of Reducing PYY Expression in Animals and Humans

We demonstrate that PYY-mediated pathways are critical for the long-term regulation of energy balance and glucose homeostasis, since PYY ablation results in late-onset obesity in female mice, and that exposure to a high fat diet leads to a more severe, early-onset obesity syndrome associated with glucose intolerance and impaired glucose-induced insulin levels. Male knockouts also develop obesity when fed on a high fat diet, in association with normal glucose tolerance and elevated glucose-induced serum insulin levels but are less affected under chow fed conditions.

It is intriguing that male mice are less prone to develop obesity in response to PYY deficiency. This may be related to the fact that male but not female PYY knockouts showed a significant increase in serum levels of IGF-1, in addition to a significant increase in serum testosterone concentrations. In particular, the significant increase in lean mass and serum concentrations of IGF-1 as, well as the markedly elevated mRNA expression of GHRH in the VMH of male PYY$^{-/-}$ mice demonstrates that PYY can influence the hypothalamo-pituitary-somatotropic axis. Our findings suggest a novel feedback inhibition loop between PYY and the hypothalamo-pituitary-somatotropic axis.

Germ line deletion of PYY did not alter absolute food intake or the expression of these orexigenic and anorexigenic peptides in a predicted way. However, the significantly decreased NPY expression and significantly increased POMC mRNA expression in the arcuate nucleus of PYY$^{-/-}$ mice is consistent with the reduced drive to remove food from the hopper and a tendency towards a reduction in spillage.

Our finding of increases of total fat mass in the absence of hyperphagia in PYY$^{-/-}$ mice suggests an important role of PYY in regulating metabolic processes that influence energy balance independently of food intake. For example, PYY deficiency appears to result in more rapid clearance of fat from the circulation and channels circulating lipids into white adipose tissue for storage. In keeping with this, PYY knockouts, in contrast to wild types, did not show any increase in serum free fatty acid or triglyceride levels during consumption of the high fat diet.

A prominent feature observed in both male and female PYY$^{-/-}$ mice before the onset of obesity is a significant improvement in glucose tolerance. In young mice, this improved glucose tolerance is associated with a significant increase in fasting or glucose-induced serum insulin levels, but by 20 weeks of age such hyperinsulinemia was no longer apparent. These data suggest that PYY not only plays a critical role in regulating insulin release under fasting and glucose-stimulated conditions, but that it may also directly reduce tissue insulin sensitivity in non-obese animals. It is possible that PYY has different effects on insulin sensitivity or glucose tolerance in lean versus obese animals. Indeed, obese fat-fed female PYY$^{-/-}$ mice had marked glucose intolerance, whereas non-obese PYY$^{-/-}$ mice exhibited significant increases in glucose tolerance compared to wild type mice.

The elevated serum insulin levels seen in our PYY$^{-/-}$ mice may be due to the lack of direct PYY1-36 inhibitory action on Y1 receptors in the pancreas, as well as indirectly via a lack of PYY3-36 stimulation of Y2 receptors in the brain stem, which can alter vagal output. The early hyperinsulinemia observed in young PYY knockout animals may be involved in their eventual development of obesity, since hyperinsulinemia is causally linked to the etiology of obese, insulin resistant states.

Inhibition of PYY expression, especially PYY[3-36], may also lead to elevated bone mineral density and/or bone mineral content, at least in males, suggesting that antagonists of PYY processing or PYY[3-36] activity have utility in the treatment of bone disorders or diseases associated with reduced bone remodeling activity or enhanced bone resorption, such as, for example, osteomalacia, hyperostosis, osteoporosis, including involutional osteoporosis, postmenopausal osteoporosis, senile osteoporosis and steroid (glucocorticoid osteoporosis). Each of these diseases is characterized by low bone mass and structural deterioration of the bone tissue resulting in bone fragility and an increased risk of fracture, especially of the hip, spine and wrist. The most common of the bone diseases, osteoporosis, is a systemic skeletal disease, characterized by low bone mass and deterioration of bone tissue, with a consequent increase in bone fragility and susceptibility to fracture. It is the most common type of metabolic bone disease in the U.S., and the condition has been estimated to affect approximately 10 million people in the United States alone. In addition to those suffering from diagnosed osteoporosis, it is estimated that up to 3 to 4 times this number may have low bone mass placing them at an increased risk of bone fracture. It is also within the scope of the present invention to treat bone conditions characterized by a need to enhance bone formation, such as, for example, bone segmental defects, periodontal defects, metastatic bone disease, and osteolytic bone disease (such as, for example, myeloma).

In summary, the absence of PYY may be a causative factor for the development of obesity and/or complications associated with obesity, including type II diabetes, and disorders of bone metabolism. The obesity-related effects of PYY deficiency are particularly evident during long-term consumption of a high fat diet, suggesting that a predisposition to low circulating PYY levels in humans combined with a high fat diet could accelerate the development of obesity, especially in females. Early diagnosis of low PYY levels combined with a reduced fat diet may therefore represent a valuable strategy for the prevention of obesity in individuals that are at risk.

TABLE 1

| | | Chow-fed | | High fat-fed | |
|---|---|---|---|---|---|
| | | PYY−/− | Wild Type | PYY−/− | Wild Type |
| Food removed (g/24 h) | Male | 6.86 ± 0.77 | 7.61 ± 0.82 | 2.97 = 0.50 | 2.97 ± 0.16 |
| | Female | 4.73 ± 0.43* | 7.71 ± 022 | 2.6 = 0.37 | 2.96 ± 0.22 |
| Spillage (g/24 h) | Male | 4.62 ± 0.71 | 5.79 ± 0.67 | 1.67 ± 0.33 | 1.73 ± 0.16 |
| | Female | 2.60 ± 0.48*** | 5.91 ± 0.47 | NO | NO |
| Actual food Intake (g/24 h) | Male | 2.24 ± 0.15 | 1.82 ± 0.24 | 1.30 ± 0.19 | 1.24 ± 0.09 |
| | Female | 1.65 ± 0.21 | 1.81 ± 0.10 | NO | NO |
| Water Intake (g/24 h) | Male | 3.75 ± 0.10* | 5.03 ± 0.41 | 3.33 ± 0.31 | 3.35 ± 0.13 |
| | Female | 3.76 ± 0.17 | 4.65 ± 0.34 | 3.423 ± 0.17 | 3.793 ± 0.17 |
| Faeces (g/24 h) | Male | 0.78 ± 0.04* | 0.65 ± 0.04 | 0.13 ± 0.02 | 0.19 ± 0.01 |
| | Female | 0.60 ± 0.07 | 0.60 ± 0.04 | NO | NO |
| Temperature (* C.) | Male | 35.8 ± 0.15 | 35.9 ± 0.12 | 36.03 ± 0.13 | 36.02 ± 0.19 |
| | Female | 35.6 ± 0.13** | 37.0 ± 0.07 | 36.63 ± 0.11 | 36.94 ± 0.13 |
| Glucose Area (mM/min) GTT (14 wks) | Male | 288 ± 48** | 576 ± 90 | 346 ± 44 | 467 ± 64 |
| | Female | 322 ± 39 | 382 ± 54 | 513 ± 108* | 241 ± 34 |
| Glucose Area (mM/min) GTT (20 wks) | Male | 268 ± 69*** | 809 ± 94 | | |
| | Female | 259 ± 53* | 490 ± 40 | | |
| WAT inguinal (g) | Male | 0.14 ± 0.01 | 0.13 ± 0.01 | 0.33 ± 0.02 | 0.027 ± 0.03 |
| | Female | 0.11 ± 0.005* | 0.14 ± 0.01 | 0.28 ± 0.03* | 0.20 ± 0.02 |
| WAT gonadal (g) | Male | 0.15 ± 0.01 | 0.15 ± 0.01 | 0.53 ± 0.05* | 0.37 ± 0.04 |
| | Female | 0.12 ± 0.01 | 0.13 ± 0.02 | 0.36 ± 0.06** | 0.16 ± 0.02 |
| WAT mesenteric (g) | Male | 0.20 ± 0.01 | 0.13 ± 0.02 | 0.43 ± 0.04 | 0.32 ± 0.02 |
| | Female | 0.15 ± 0.01 | 0.16 ± 0.01 | 0.30 ± 0.03** | 0.17 ± 0.01 |
| WAT retroperitoneal (g) | Male | 0.04 ± 0.004 | 0.04 ± 0.004 | 0.14 ± 0.01 | 0.12 ± 0.02 |
| | Female | 0.03 ± 0.002 | 0.02 ± 0.003 | 0.07 ± 0.01 | 0.04 ± 0.005 |
| WAT inguinal (g) (28 wks) | Male | ND | ND | | |
| | Female | 0.30 ± 0.04** | 0.16 ± 0.012 | | |
| WAT gonadal (g) (28 wks) | Male | ND | ND | | |
| | Female | 0.52 ± 0.07** | 0.20 ± 0.04 | | |
| WAT mesenteric (g) (28 wks) | Male | ND | ND | | |
| | Female | 0.37 ± 0.05 | 0.18 ± 0.02 | | |
| WAT retroperitoneal (g) (28 wks) | Male | ND | ND | | |
| | Female | 0.08 ± 0.01 | 0.03 ± 0.01 | | |
| Free T4 (pmol/L) | Male | 18.04 ± 1.18 | 19.45 ± 1.68 | 16.18 ± 1.32 | 16.21 ± 1.43 |
| | Female | 23.87 ± 1.24 | 26.94 ± 1.77 | 20.55 ± 1.04 | 24.58 ± 3.49 |
| Leptin (ng/ml) | Male | 3.16 ± 0.31 | 3.55 ± 0.37 | 10.62 ± 1.50* | 6.72 ± 0.59 |
| | Female | 4.00 ± 0.33 | 4.22 ± 0.20 | 8.88 ± 0.91 | 8.28 ± 0.67 |
| Glucagon (pg/mL) | Male | 32.21 ± 7.91 | 25.40 ± 11.8 | | |
| | Female | 6.78 ± 1.05 | 9.08 ± 1.97 | | |
| Testosterone (n/M) | Male | 20.80 ± 6.86 | 1.95 ± 0.75 | 18.40 ± 7.15 | 3.47 ± 1.07 |
| Intestinal length (cm) | Male | 38.84 ± 0.49** | 36.54 ± 0.60 | 37.83 ± 0.56* | 35.56 ± 0.77 |
| | Female | 38.23 ± 0.49 | 37.05 ± 0.37 | 35.85 ± 0.37*** | 33.0 ± 0.56 |
| Intestinal weight (% BW) | Male | 2.65 ± 0.07 | 2.65 ± 0.07 | 1.84 ± 0.10* | 2.19 ± 0.10 |
| | Female | 3.15 ± 0.10 | 3.40 ± 0.32 | 2.29 ± 0.14** | 1.74 ± 0.11 |
| Colon length (cm) | Male | 7.39 ± 0.14 | 7.5 ± 0.15 | 7.17 ± 0.14* | 6.31 ± 0.33 |
| | Female | 7.23 ± 0.15** | 6.50 ± 0.30 | 6.15 ± 0.11 | 5.88 ± 0.08 |
| Colon weight (% BW) | Male | 0.63 ± 0.03 | 0.61 ± 0.02 | 0.38 ± 0.01 | 0.49 ± 0.06 |
| | Female | 0.77 ± 0.02*** | 0.65 ± 0.02 | 0.49 ± 0.02 | 0.48 ± 0.01 |
| Liver (% B/W) | Male | 4.56 ± 0.09*** | 4.00 ± 0.09 | 4.39 ± 0.10 | 4.26 ± 0.13 |
| | Female | 4.40 ± 0.10 | 4.25 ± 0.08 | 4.28 ± 0.09 | 4.07 ± 0.20 |

ND, not determined;
WAT, white adipose tissue;
WT, wild type mice.

Data in Table 1 represent means±SEM of 7-12 mice per group. $^{H}$p<0.05, $^{HH}$ p<0.01, $^{HHH}$p<0.001 versus wild type mice on the same diet.

TABLE 2

Effect of PYY deficiency on mRNA levels of various orexigenic and anorexic peptide neurotransmitters in the hypothalamus.

| mRNAs | PYY± | Wild type | Difference |
|---|---|---|---|
| NPY | 79 = 4.04 | 100 = 3.03 | 0.021 (−21.2%)** |
| POMC | 125 = 3.79 | 100 = 6.33 | 0.019 (+25.3%)** |
| VP (SO) | 95 = 9.05 | 100 = 2.81 | 0.012 (+5.4%) |
| VP (PVN) | 90 = 2.64 | 100 = 4.53 | 0.025 (−10.2%) |
| GHRH (Arc) | 109 = 5.08 | 100 = 6.78 | 0.005 (+8.47%) |
| GHRH (VMHDM) | 132 = 6.25 | 100 = 5.28 | 196.9 (+32.3%)** |

Data represents mean ± SEM of 5 mice per group.
**p < 0.01

EXAMPLE 11

Production of Hybridomas Expressing Antibodies that Bind Specifically to the N-Terminal Portion of Human PYY [1-36] but not at High Affinity to Human PYY[3-36]

Selecting and Synthesizing an Immunogen

A nonapeptide PYY[1-9] (SEQ ID NO: 29) comprising amino acid residues 1-9 of human PYY[1-36] was selected as an immunogen. This portion of PYY comprises the N-terminus of the full-length human PYY protein, to maximize the likelihood of obtaining monoclonal antibodies that bind specifically to the first 1 or 2 or 3 residues of the full-length PYY, thereby having utility in specifically binding to PYY[1-36] i.e., binding at higher affinity to PYY[1-36] than to PYY [3-36]. The PYY[1-9] peptide was conjugated to keyhole limpet hemocyanin (KLH) for immunization.

Generation of Mouse Monoclonal Antibodies

Groups of 10 to 12 week old female BALB/c mice were each immunized by intraperitoneal injection of 50 µg PYY [1-9]-KLH conjugate emulsified with Freund's Complete Adjuvant, followed by two intraperitoneal injections of 25 µg PYY[1-9]-KLH conjugate emulsified with Freund's Incomplete Adjuvant. Immunizations were at standard intervals. Blood samples were collected after booster injections to monitor the immune response. After a suitable rest period, mice showing a high antibody titer were given a final intravenous booster injection of 50 µg PYY[1-9]-KLH conjugate in phosphate buffered saline (PBS) 3 days prior to cell fusion. Spleens were removed aseptically. Spleen cells were collected through a 70 µm mesh cell strainer, and fused with SP2/0 myeloma cells by polyethylene glycol $PEG_{3000-3700}$.

Hybridoma cells were selected using HAT-medium (Hypoxanthine, Aminopterine, Thymidine-medium), and arrayed on 10×384 well plates, according to standard procedures.

Antibody Characterization

Supernatants from growing cells were assayed for the presence of PYY[1-9] antibodies by ELISA according to standard techniques (Harlow 1988). Briefly, 10×384-well Maxisorp EIA plates (NUNC) were coated with unconjugated PYY peptide. The plates were blocked using 1% (w/v) bovine serum albumin (BSA) in PBS, and, following plate washing according to standard procedures, the hybridoma supernatants were added. Following further washing of the plates according to standard procedures, goat anti-mouse IgG(H+L) antibody conjugated to horseradish peroxidase was added. TMB (Frey, Meckelein et al. 2000) was then added as substrate. After about 30 min, the colour reaction was stopped with the addition of 100 uL 1 M phosphoric acid and absorbances were measured at 450 nm in a iEMS microplate reader (Thermo-Labsystems, Helsinki, Finland). Several positive hybridomas were selected, including the hybridoma designated 7K11, and sub-clones designated 7K11-F9, 7K11-G3 and 7K11-C8.

Antibody Cross-Reactivity

Figure 14:
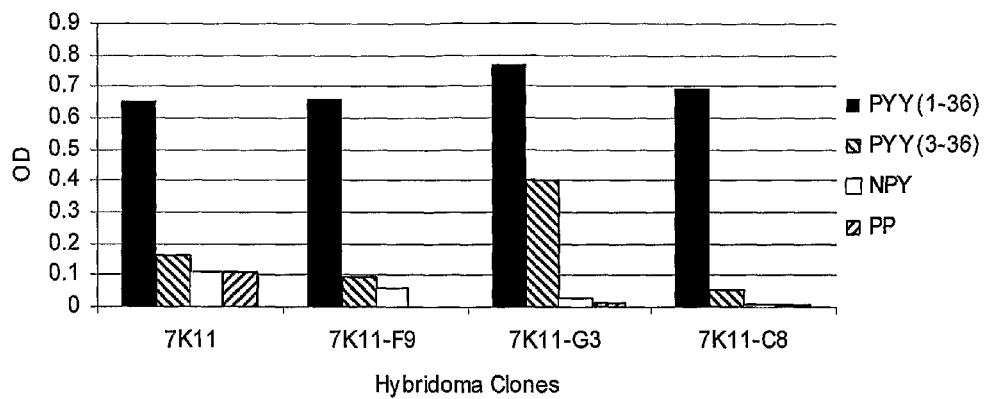
FIG. 14 is a graphical representation showing the immunoreactivity of monoclonal antibodies produced by immunization of Balb/c mice with the nonapeptide PYY[1-9] (SEQ ID NO: 29), to peptide PYY[1-36] (SEQ ID NO: 27), PYY [3-36] (SEQ ID NO: 28), NPY and PP. Antibodies produced by the hybridoma clones designated 7K11, 7K11-F9, 7K11-G3 and 7K11-C8 were shown to bind specifically to human PYY[1-36].
Figure 16:
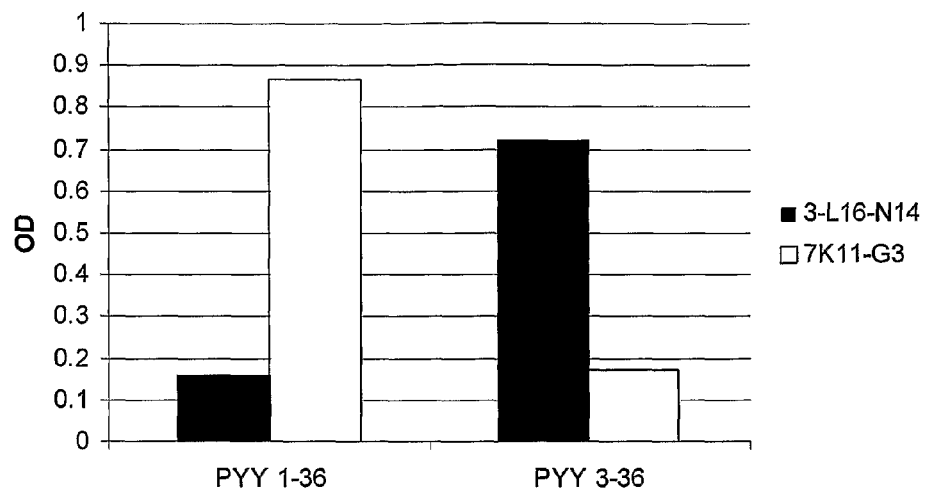
FIG. 16 is a graphical representation showing the immunoreactivity of monoclonal antibodies produced by the deposited hybridomas 3L16-N14 and 7K11-G3 to PYY[1-36] (SEQ ID NO: 27) and PYY[3-36] (SEQ ID NO: 28) in ELISA using anti-IgM-biotin and streptavidin-conjugated horseradish peroxidase (HRP) as detection reagents. Hybridoma culture supernatants were incubated with 2.5 μg PYY peptide as indicated on the x-axis coated onto immunoplates. Data indicate that antibodies produced by hybridoma 3L16-N14 bind specifically to human PYY[3-36] and antibodies produced by hybridoma 7K11-G3 bind specifically to human PYY[1-36].

To determine specificity of the monoclonal antibodies produced by hybridomas designated 7K11, 7K11-F9, 7K11-G3 and 7K11-C8 for full length PYY, ELISA was performed against the antigens PYY[1-36], PYY[3-36], NPY and pancreatic peptide (PP) under identical conditions as described herein above. As shown in FIG. 14, the binding affinity of the monoclonal antibodies to PYY[3-36], NPY and PP were low compared to their binding to PYY[1-36], suggesting strongly that the expressed monoclonal antibodies bind specifically to residues at the N-terminus of full-length PYY, e.g., amino acids 1 and/or 2 and/or 3 of full length PYY. These data were confirmed for the monoclonal antibody expressed by hybridoma 7K11-G3 (FIG. 16).

Figure 17:
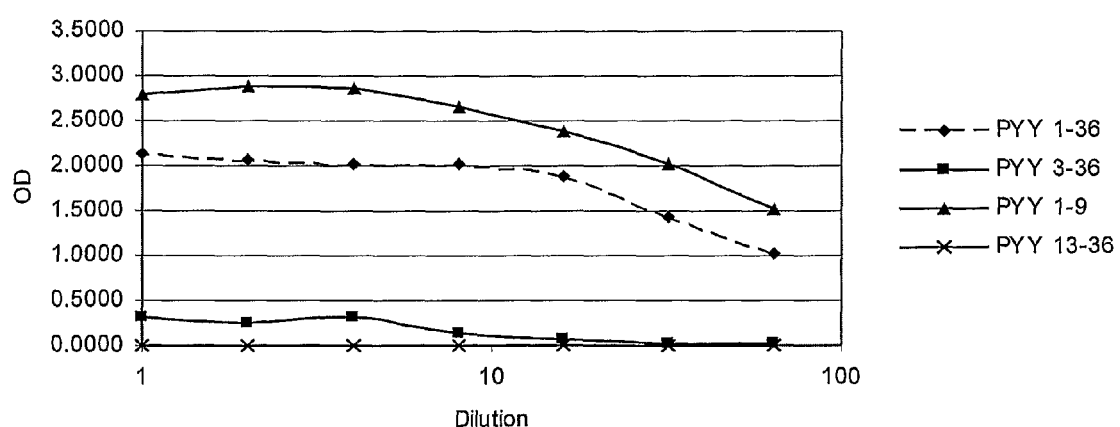
FIG. 17 provides graphical representations showing the titers of monoclonal antibodies produced by the deposited hybridoma 7K11-G3 in ELISA using anti-IgM conjugated with alkaline phosphatase as a detection reagent. Hybridoma culture supernatants were diluted serially up to 1/100-fold and incubated with 2.5 μg of PYY[1-36] peptide (SEQ ID NO: 27; filled diamonds), PYY[3-36] peptide (SEQ ID NO: 28; filled squares) or PYY[1-9] peptide (SEQ ID NO: 29; white triangles), or alternatively, with 1.0 μg of PYY[13-36] peptide (SEQ ID NO: 31; white crosses) coated onto immunoplates. Data indicate that antibodies produced by hybridoma 7K11-G3 bind specifically to human PYY[1-36] over all concentration ranges tested.

Direct ELISA were also performed to determine the antibody titers of monoclonal antibodies produced by the deposited hybridoma 7K11-G3, using anti-IgM conjugated with alkaline phosphatase as a detection reagent. Hybridoma culture supernatants were diluted serially up to 1/100-fold and incubated with 2.5 µg of PYY[1-36], PYY[3-36], or PYY[1-9], or alternatively, with 1.0 µg of PYY[13-36] being coated onto immunoplates. Data in FIG. 17 indicate that antibodies produced by hybridoma 7K11-G3 bind specifically to PYY [1-9] and PYY[1-36] over all concentration ranges tested. These data again confirm the specificity of monoclonal antibodies produced by hybridoma 7K11 and sub-clones thereof, especially 7K11-G3 for full-length PYY. The inability of the antibody to bind at high affinity to PYY[3-36] indicates that the antibody recognizes the N-terminal portion of PYY[1-36] that is processed to yield PYY[3-36].

EXAMPLE 12

Production of Hybridomas Expressing Antibodies that Bind Specifically to Human PYY[3-36]

Selecting and Synthesizing an Immunogen

PYY[3-36] comprising amino acid residues 3-36 of full-length human PYY (i.e., SEQ ID NO: 28) was selected as an immunogen. This portion of PYY comprises that portion of full-length PYY remaining after the N-terminal two amino acids are cleaved. The PYY[3-36] peptide was conjugated to keyhole limpet hemocyanin (KLH) for immunization.

Generation of Mouse Monoclonal Antibodies

Groups of 10 to 12 week old $PYY^{-/-}$ mice were each immunized by intraperitoneal injection of 50 µg PYY[3-36]-KLH conjugate emulsified with Freund's Complete Adjuvant, followed by two intraperitoneal injections of 25 µg PYY[3-36]-KLH conjugate emulsified with Freund's Incomplete Adjuvant. Immunizations were at standard intervals. Blood samples were collected after booster injections to monitor the immune response. After a suitable rest period, mice showing a high antibody titer were given a final intravenous booster injection of 50 µg PYY[3-36]-KLH conjugate in phosphate buffered saline (PBS) 3 days prior to cell fusion. Spleens were removed aseptically. Spleen cells were collected through a 70 µm mesh cell strainer, and fused with SP2/0 myeloma cells by polyethylene glycol $PEG_{3000-3700}$.

Hybridoma cells were selected using HAT-medium (Hypoxanthine, Aminopterine, Thymidine-medium), and arrayed on 10×384 well plates, according to standard procedures.

Antibody Characterization

Supernatants from growing cells were assayed for the presence of PYY[3-36] antibodies by ELISA according to standard techniques (Harlow 1988). Briefly, 10×384-well Maxisorp EIA plates (NUNC) were coated with unconjugated PYY peptide. The plates were blocked using 1% (w/v) bovine serum albumin (BSA) in PBS, and, following plate washing according to standard procedures, the hybridoma supernatants were added. Following further washing of the plates according to standard procedures, goat anti-mouse IgG(H+L) antibody conjugated to horseradish peroxidase was added. TMB (Frey, Meckelein et al. 2000) was then added as substrate. After about 30 min, the colour reaction was stopped with the addition of 100 uL 1 M phosphoric acid and absorbances were measured at 450 nm in a iEMS microplate reader (Thermo-Labsystems, Helsinki, Finland). Several positive hybridomas were selected, including the hybridomas designated 8C19, 2F3, 6C1, 4M20, 3L16, 3K17 and 8A10.

Antibody Cross-Reactivity

Figure 15:
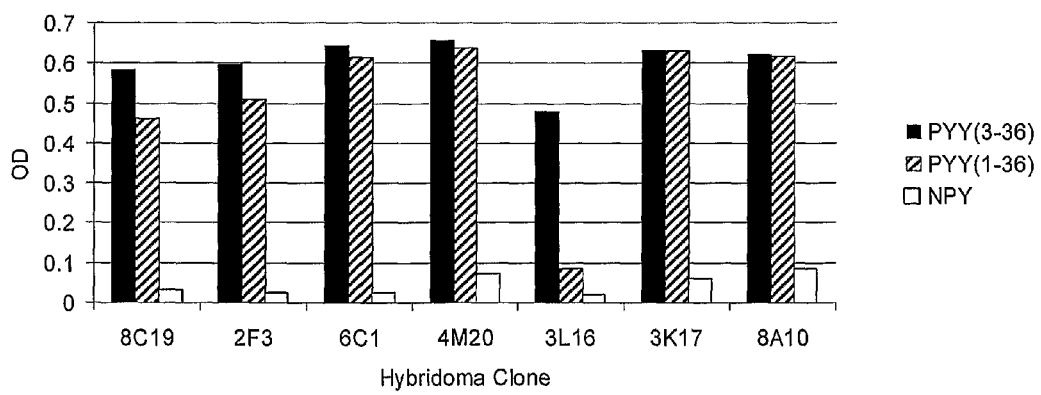
FIG. 15 is a graphical representation showing the immunoreactivity of monoclonal antibodies produced by immunization of PYY-knockout mice with the C-terminal peptide PYY[3-36] (SEQ ID NO: 28), to peptide PYY[1-36] (SEQ ID NO: 27), PYY[3-36] (SEQ ID NO: 28) and NPY. Antibodies produced by the hybridoma clone designated 3L16 were shown to bind specifically to human PYY[3-36], whilst antibodies produced by the hybridomas designated 8C19, 2F3, 6C1, 4M20, 3K17 and 8A10 were shown to bind with approximately equal affinity to both human PYY[1-36] and human PYY[3-36]. None of the antibodies produced bound significantly above background to NPY.

To determine specificity of the monoclonal antibodies produced by hybridomas designated 8C19, 2F3, 6C1, 4M20, 3L16, 3K17 and 8A10 for PYY[3-36], direct ELISA was performed against the antigens PYY[1-36], PYY[3-36] and NPY under identical conditions as described herein above. As shown in FIG. 15, most antibodies bound with equal affinity to PYY[1-36] and PYY[3-36]. However, the binding affinity of a single monoclonal antibody designated 3L16 to PYY[1-36] and NPY was low compared to its binding to PYY[3-36], suggesting strongly that the monoclonal antibody expressed by hybridoma 3L16 binds specifically to PYY[3-36]. These data were confirmed for the monoclonal antibody expressed by the sub-clone designated 3L16-N14 (FIG. 16).

Figure 18:
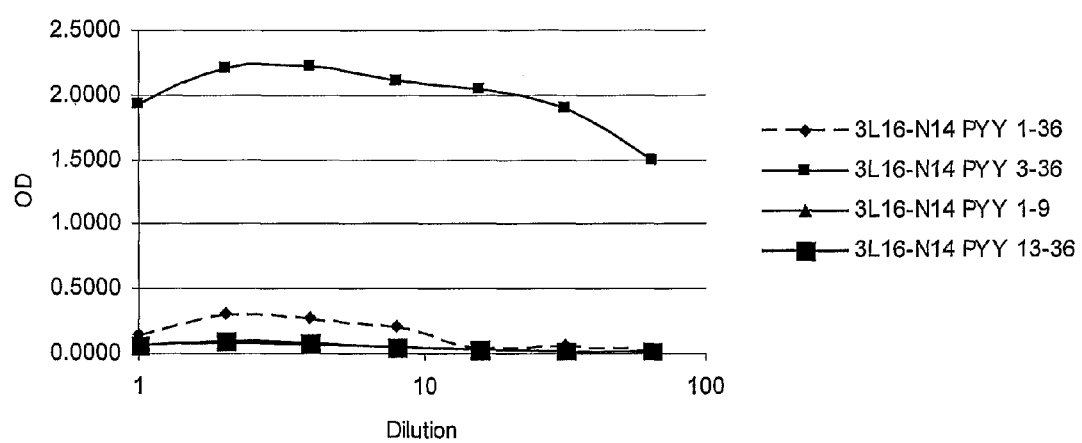
FIG. 18 provides graphical representations showing the titers of monoclonal antibodies produced by the deposited hybridoma 3L16-N14 in ELISA using anti-IgM conjugated with alkaline phosphatase as a detection reagent. Hybridoma culture supernatants were diluted serially up to 1/100-fold and incubated with 2.5 μg of PYY[1-36] peptide (SEQ ID NO: 27; filled diamonds), PYY[3-36] peptide (SEQ ID NO: 28; filled squares) or PYY[1-9] peptide (SEQ ID NO: 29; white triangles), or alternatively, with 1.0 μg of PYY[13-36] peptide (SEQ ID NO: 31; white crosses) coated onto immunoplates. Data indicate that antibodies produced by hybridoma 3L16-N14 binds specifically to human PYY[3-36] over all concentration ranges tested.

Direct ELISA were also performed to determine the antibody titer of the monoclonal antibodies produced by the deposited hybridoma 3L16-N14, using anti-IgM conjugated with alkaline phosphatase as a detection reagent. Hybridoma culture supernatants were diluted serially up to 1/100-fold and incubated with 2.5 μg of PYY[1-36], PYY[3-36], or PYY[1-9], or alternatively, with 1.0 μg of PYY[13-36] being coated onto immunoplates. Data indicate that antibodies produced by hybridoma 3L16-N14 bind specifically to PYY[3-36] but not at high affinity to PYY[1-36], PYY[1-9] or PYY[13-36] over all concentration ranges tested. These data again confirm the specificity of monoclonal antibodies produced by hybridoma 3L16-N14 and indicate binding of the antibodies to a region within residues from about position 3 to about position 13 of full-length PYY i.e., PYY[1-36] (FIG. 18).

EXAMPLE 13

Immunoassay for Determining Amounts of PYY[1-36] and PYY[3-36] in Sera

Sandwich ELISA

Plates are coated for 16 h at 20° C. with 100 μL of purified monoclonal or polyclonal antibodies that bind with approximately equal affinity to PYY[1-36] and PYY[3-36] as a capture reagent. Antibodies are at a concentration of about 1 μg/well in 50 mM carbonate buffer, pH 9.6. All subsequent steps are carried out at 20° C. The wells are washed 3 times with PBS containing Tween20 detergent (i.e., PBST) and non-specific binding sites blocked with 1% BSA in PBS for 1 hour.

Sera are diluted with carbonate buffer pH 9.6, added to the wells in duplicate (about 100 μl/well), and incubated for about 1 h. The wells are then washed 3 times with PBST, and then 100 μL of HRP-labelled monoclonal antibody 3L16-N14 (diluted 1:5000 in PBST) is added to one replicate set of the wells and 100 μL of HRP-labelled monoclonal antibody 7K11-G3 (also diluted 1:5000 in PBST) is added to the other replicate set of the wells. Plates are then incubated for about 30 min.

The dilution of labelled antibody used is determined by direct ELISA to provide an absorbance at 450 nm of between 1.0 and 1.5. Plates are washed as before and ABTS substrate is added to all wells. The reaction is stopped after about 20 min and absorbance values are measured. The amount of PYY[1-36] in sera is determined by binding of antibody 7K11-G3, and the amount of PYY[3-36] in sera is determined by binding of antibody 3L16-N14. The relative amounts of PYY[1-36] and PYY[3-36] are generally expressed as the ratio PYY[3-36]/PYY[1-36] or alternatively, the ratio PYY[3-36]/PYY[total] wherein PYY[total] is the amount of PYY[1-36] and PYY[3-36] in the sample.

Monoclonal and polyclonal antibodies are tested as capture and/or detection antibodies in the plate sandwich ELISA, using a wide range of concentrations (0.001-10 ug/mL) of sample.

We claim:

1. An isolated monoclonal or recombinant antibody, or an antigen-binding fragment thereof, wherein the antibody or antigen-binding fragment thereof specifically binds to human PYY [1-36] and binds to human PYY [1-36] more strongly or tightly than it binds to human PYY [3-36].

2. The isolated antibody or antigen binding fragment according to claim 1, wherein said antibody or antigen binding fragment has the binding affinity of a monoclonal antibody produced by the hybridoma designated 7K11 G3 (ECACC Accession No. 06022101).

3. The isolated antibody according to claim 1, wherein said antibody is produced by the hybridoma designated 7K11 G3 (ECACC Accession No. 06022101).

4. The isolated antibody or antigen binding fragment according to claim 1, wherein the antibody does not bind NPY and/or PP at a level significantly above background.

5. The isolated antibody or antigen binding fragment according to claim 1, wherein said antibody or antigen binding fragment does not detectably bind PYY[3-36].

6. The isolated antibody or antigen binding fragment according to claim 1, wherein said antibody or antigen binding fragment binds to an epitope comprising at least the first three amino acids of PYY as set out in SEQ ID NO: 10.

7. The isolated antibody or antigen binding fragment according to claim 1, wherein said antibody or antigen binding fragment binds to an epitope present in the peptide of SEQ ID NO: 29.

8. An isolated monoclonal or recombinant antibody or an antigen binding fragment thereof, wherein the antibody or antigen binding fragment thereof has the binding affinity of a monoclonal antibody produced by the hybridoma designated 3L16-N14 (ECACC Accession No. 06022102).

9. The antibody according to claim 8, wherein said antibody is produced by the hybridoma designated 3L16-NI4 (ECACC Accession No. 06022102).

10. A cell line capable of producing a monoclonal antibody according to claim 1.

11. A kit comprising one or more isolated antibodies or antigen binding fragments according to claim 1 and one or more reagents selected from the group consisting of (i) an antibody that binds equally to both human PYY [1-36] and human PYY [3-36] polypeptides; (ii) a PYY[1-36] peptide; (iii) a PYY[3-36] peptide; (iv) a reagent for performing an immunoassay; and (v) combinations of (i) to (iii).

12. A method comprising contacting a sample with an antibody according to claim 1 for a time and under conditions sufficient for an antigen-antibody complex to form and then detecting the complex, wherein the presence of detectable complex indicates the presence of PYY [1-36], and wherein the absence of detectable complex indicates that the sample does not express PYY [1-36].

13. The method of claim 12 further comprising:
determining the amount of the complex formed, wherein the amount of the complex correlates positively with the amount of PYY[1-36] in the sample.

14. The method according to claim 12 comprising:
(i) contacting a sample with a known amount of labelled PYY[1-36];
(ii) contacting the combined sample and labelled PYY with one or more antibodies according to claim 1 for a time and under conditions sufficient for an antigen-antibody complex to form; and
(iii) detecting the amount of labelled PYY [1-36] in the antigen-antibody complex, wherein the amount of labelled PYY [1-36] in the complex is inversely proportional to the amount of PYY [1-36] in the sample.

15. The method according to claim 13 or 14 additionally comprising a first step comprising contacting the sample with an antibody that binds to both PYY[1-36] and PYY[3-36] for a time and under conditions sufficient for an antigen-antibody complex to form to thereby capture total PYY in the sample.

16. The method according to claim 13 or 14 additionally comprising determining the amount of PYY[3-36], PYY[total], or both in the sample.

17. A process for determining the propensity of a subject to become obese or to develop a complication or medical condition associated with obesity, said process comprising obtaining a biological sample from a subject, performing the method according to claim 16 on the biological sample, wherein a low level of PYY[3-36] in the biological sample relative to the amount of PYY[3-36] in a normal or healthy human subject is indicative of a propensity for the subject to become obese or to develop one or more complications associated with obesity.

18. A process for determining the propensity of a subject to become obese or to develop a complication or medical condition associated with obesity, said process comprising obtaining a biological sample from a subject, performing the method according to claim 16 on the biological sample, wherein a low level of PYY[total] in the biological sample relative to the amount of PYY[total] in a normal or healthy human subject is indicative of a propensity for the subject to become obese or to develop one or more complications associated with obesity.

19. A process for determining the propensity of a subject to become obese or to develop a complication or medical condition associated with obesity, said process comprising obtaining a biological sample from a subject, performing the method according to claim 16 on the biological sample, wherein a high level of PYY[3-36] in the biological sample relative to the amount of PYY[3-36] in a normal or healthy human subject is indicative of a low risk of obesity or a low propensity for developing one or more complications associated with obesity.

* * * * *

SEQUENCE LISTING

<160> NUMBER OF SEQ ID NOS: 31

<210> SEQ ID NO 1
<211> LENGTH: 511
<212> TYPE: DNA
<213> ORGANISM: Mus musculus
<220> FEATURE:
<221> NAME/KEY: CDS
<222> LOCATION: (37)..(333)

<400> SEQUENCE: 1

```
cctcctgctc atcttgcttc ggaagctgta gctgct atg gtg gcg gtg cgc agg        54
                                       Met Val Ala Val Arg Arg
                                       1               5 cct tgg ccc gtc acg gtc gca atg ctg cta atc ctg ctc gcc tgt ctg       102
Pro Trp Pro Val Thr Val Ala Met Leu Leu Ile Leu Leu Ala Cys Leu
            10                  15                  20 gga gcc ctg gtg gac gcc tac cct gcc aaa cca gag gct ccc ggc gaa       150
Gly Ala Leu Val Asp Ala Tyr Pro Ala Lys Pro Glu Ala Pro Gly Glu
        25                  30                  35 gac gcc tcc ccg gag gag ctg agc cgc tac tac gcc tcc ctg cgc cac       198
Asp Ala Ser Pro Glu Glu Leu Ser Arg Tyr Tyr Ala Ser Leu Arg His
    40                  45                  50 tac ctc aac ctg gtc acc cgg cag cgg tat gga aaa aga gat gtc ccc       246
Tyr Leu Asn Leu Val Thr Arg Gln Arg Tyr Gly Lys Arg Asp Val Pro
55                  60                  65                  70 gca gct ctg ttc tcc aaa ctg ctc ttc aca gac gac agc gac agc gag       294
Ala Ala Leu Phe Ser Lys Leu Leu Phe Thr Asp Asp Ser Asp Ser Glu
                75                  80                  85 aac ctc ccc ttc agg cca gaa ggt ttg gac cag tgg tga agactccccc        343
Asn Leu Pro Phe Arg Pro Glu Gly Leu Asp Gln Trp
                90                  95 aaggcctcct gcgagatgtg ttaactacac cgacttcact tgcatgtttg gtttaagaag    403
```

```
agggcacttc atatctcggt gtctcggaca cccagactgg agggctgtgt gtgttcattt    463
ccctgtccct aaataaaaag caaatttcgc acaaaaaaaa aaaaaaaa                511

<210> SEQ ID NO 2
<211> LENGTH: 98
<212> TYPE: PRT
<213> ORGANISM: Mus musculus

<400> SEQUENCE: 2

Met Val Ala Val Arg Arg Pro Trp Pro Val Thr Val Ala Met Leu Leu
1               5                   10                  15

Ile Leu Leu Ala Cys Leu Gly Ala Leu Val Asp Ala Tyr Pro Ala Lys
            20                  25                  30

Pro Glu Ala Pro Gly Glu Asp Ala Ser Pro Glu Glu Leu Ser Arg Tyr
        35                  40                  45

Tyr Ala Ser Leu Arg His Tyr Leu Asn Leu Val Thr Arg Gln Arg Tyr
    50                  55                  60

Gly Lys Arg Asp Val Pro Ala Ala Leu Phe Ser Lys Leu Leu Phe Thr
65                  70                  75                  80

Asp Asp Ser Asp Ser Glu Asn Leu Pro Phe Arg Pro Glu Gly Leu Asp
                85                  90                  95

Gln Trp

<210> SEQ ID NO 3
<211> LENGTH: 10095
<212> TYPE: DNA
<213> ORGANISM: mus musculus

<400> SEQUENCE: 3
ggctgggcgt ctgcctttaa tcacagccct caggaggcag aggtggacgt atctctgtgg     60
gttcaaggac ggtctggtct atagaactag ttccaggaca gccagggcta tacagagaaa    120
ccgtgtcttg aaaacaacag cagcaacaac aacaacaaac aacaaatcat aaggcaaact    180
gaagacaagg actgcatctt catcaagttg ggccacctgg ttaaggacat aaagatcaaa    240
cccctggcag agatccattt gttctccctg tccatcaagg agtcagaagc cattgtcttc    300
tcctagccgc atcccttagg gatgaggctc tgttaccatg gcagtgcgga agtagactca    360
ggttcaaggc ttttgtcatt gttgggaact gccatggtca cgttggtgtg aatgttaagt    420
gttccgagaa aggtagcctc tgccatctga ggtaccacat ctctgtccat cttttcattg    480
tctcggtgca gagaggctgc cagggcaaca gggtggataa accccacact gaccatgcag    540
gcaacaggct gctgtggctc tgttctggtg ggattcatct ctggcccag agacacaagc     600 actgtctcgg ctgccatgcc caaagagctg ctgctgcagc tgtggggtgc ctggctggca    660
ctgttgtctg ctacacatta ttcagggact acactgtcac tctgagcaat gttgccaggc    720
cacctttgat ctatctaaga gctacacaca gccatctgac ctgggatctc tgggaaagaa    780
gcaagtttaa ctaagtctct ctagcagaaa tccagccatc ttgtgaaacc cacagagagt    840
ctccatgcag agatcccagg ttccagctgt gtttaccaca cagggttttt aatagaagaa    900
tcagaagggt tggagaaatg gctcagcggt taagaacacc gactgctctt ccagaggtcc    960
tgagttcaat cccagcaac cacagggtgg ctcacgacca tctgtaatgg gatctgatgc    1020
cctcttctgg tgcgtctgaa ggccagaggt ggcctctctg aagagagtaa tggtgtactc    1080
atgtacataa aataaataaa tcttaaaaaa agaagaagaa gaatcagaaa ttaaattaaa    1140
tcctgcttct ttaaaaaaag acgtttgctg agtgtggtgg cacacacttt tcattccagt    1200
```

```
acttggaagg cagaaacagg tggatttgta cgatttcaag tctagcctga tctacattgt    1260
gaggtccggg tcatccagga ctacaaaata aaacctagtc taaaaacaca acaaaacaaa    1320
caaacaagca aacaaacaaa ctccccacca ccggccaaat gtattgtctg tgctggaaag    1380
atttctcttt ttctattttc tttttaact tgtgtggtgt ggtgtggtgt ggtgtggtgt    1440
ggtgtggtgt gtgtgtgtgt gtgtgtgtgt gtgtgtacat gtgccccagt gcatgtgtgg    1500
tcagaggaca gctttgtgga gttgactctt ttcttccacc tttatgccgg ttccagggat    1560
agaactcagg cctgcagagc tagggccttt accagttgag ccgtctcaca caccctcatg    1620
cctgcttttc cttagcaaca aatttgaatg gattaagttt ttagatttgt tacagtcctg    1680
ttctaaaagg tacttagaaa ccatctcgtt aaagactgcc catccctctc tggtgtctgt    1740
tttcactcag tatctcttac tttggggaa atccctgccc agctctgcat agacacgtta    1800
agcatcaggg accgtctgca gacttatctc atcctcttaa acggaagaca cggagataac    1860
cagagcttcc aaacctgcca ttaccttggg ttccaggaac aacggagcct tgctggctca    1920
ttcccagatg agggcaacca tccacaaggg tggggcttgt accctggaga atgagtcacc    1980
atctcctgag aaccagcctg tctcctcagg tgacaggac gtctttggac atcttgaaga    2040
attgaaactg agactatggt caccagatta tgccttgact aaatctgctt gggttcaatt    2100
ctggtcatca gggttggtgg caagtacctt tacctgctga gctatttac cagatttcct    2160 cttctttcct tcccccacct ctggcctttc atcctttcta cagggtct ccatcctggc    2220 tagttttatg tcatcattat acaagctaga atcacctgaa aggagggaag ctcaattgag    2280
aaaatgcctc cataagatac atctgtagcc cattttcttc attagtgatt gacagaggag    2340
gactcaaccc atcttgggtg gtgctatccc tgggctggtg gtcctgggtt ttacaataaa    2400
gcaggaggag ttagccatga ggagcaagcc agtaagcagc atccctccat ggcctctgca    2460
tcagctcctg cctccaggtt cttgccctga ttcatttcct gtcctgatgt tctttgagag    2520
ttaaactgtg atgtggaagt gtcagccaaa taaagtctgc ctccccaact tccttggtt    2580 actgtgtttc atcatgccat agtgaccata attaagatat cctgggatag cctcaagctc    2640
ttaatatagc caaaaacata cacgctaaac ttccgatctt gcttctacat ctggagtact    2700
gggggttcta gatgtgtggt ggggatccct gctaatgctg ggggtcaatc tctgagatct    2760
gtgcatgcta agtaagaact agacccgaga cacaccacca cttcctcttg ttattttgtt    2820
ctgaacaagg tgacattaca tagcccaggc tggcctggaa cttgagatcc ctctagtgct    2880
gggattacag gttatgcacc cacgtctgta aggaatgact cttttcctgcc agtgactttg    2940 cttggggagg agtcattggc aatgtcctgt ctatcagagg tcctgttgta gatactgggt    3000
tcgggtgacc actggtatgt tacagaaggc taagtcactt aggataagtg gacttgatat    3060
gactagacaa gacgagtgat tttccgaggt tcaggtctct aacctccttg acctgggttg    3120 gttttatta tgtcctctga ggacgaagag caatggaatc ccagcaattc tgtctctgta    3180
tccttcaagg agaggttgga ggctggtcct ggtctcaagt gcacagtaac aattgttttg    3240
gaagtttgcc ctcacaggtg tcgtcaccca gtttgcagac ttgtctcatg gaggctgagt    3300
caccggtcga tgatgatggg gggcactcag tggggccagc caagtctatt gatcgagggc    3360
tgagacatcc tccccactaa tcaacagtta attaagtctt tgatgagggg gtggtgatta    3420
atgactagaa ggcctgtcct gtaattgggg catggaggga ataccaagat gcacagaggg    3480
gctttgtgag gatgggggag gctggttcct ggtccacact gagggacacc cccttgggct    3540
cagcttgctt tcatacactg aatctaggca tctaggcctt tccttatatc ctctggcttc    3600
```

```
tccacccttt cccctttcct tctttccttg aaccttgcat tccctaagac cagggttgag    3660
ggctggggag gtagggggt agggacattc aggcatggca gatcctctgt gttccttttt    3720
tttttgttaa ttaggtattt tcctcgttta cattttcaat gctatcccaa aggtccccca    3780
tacccacccc cccaatcccc tccccccccc cactctctgt gttcctctta caagctcctt    3840
tgtctctgtc tggggttggt gcacctgcaa cctcctcact accaaatgcc cattcccatc    3900
tcctgtccct tgtagcctat agtgtccttg tctatctagg ctccagcctc tgtgatcaca    3960
cctgccctag ccagcaccca ggttatcctc tcctgagcga gcacctgtca tgtcatccca    4020
cgacatttgg ttttccctaa agggttagaa ttcttgtact tctgttatct tctctccaaa    4080
cagaacatcg gctggcctct ctgtaactgt tctggggtct tttaagactg ggagtccctg    4140
ctgggtggtg gtggctcaca cctttgatcc cagcacttgg gaggcagagg caggcggatt    4200
tctgagttca aggccagcct ggtctacaaa gtgggttcca ggacagccag ggatatacag    4260 agaaccctg tctcaaaaat accagaaaaa aaaaaaaaa agactgggcg tccccatgga    4320
tgtggctctc ctgagatgag ggtccttgga ggacaaagct gtgacttgac ctccagatac    4380
aggctcccta aggagaactg tgtctctctt ttctccaagg ctgggctaca tgtcctctca    4440
tcctgatctt ttccacttcc gtgctcagca ggatgtccca gttcttcttc tgttacaggg    4500
gggcccctgt gggacctggc tggctgataa ggatccattt ccggagagtg caggtgactg    4560
aacccataaa aaaggtgatt gaagaagccc tggatgctcc atctcaggtg agttctaaaa    4620
atagcatcca cagccatctg tcctgggaat tggaagggct ggcccagaac tagggggcctg    4680 ggcaagatgg ttctccctgt ttccatgggc tagaagtggt ggagactctg gcagggctgg    4740
gagaaggacc cagaaagggt tggacttcct atggtcctct cttcttggtt aagcaggtgg    4800
gtctgatagg gctcttcccc atggggctgg tggtctgggg tccttccctc tctcagccaa    4860
tcagagtagg ctgacactgc ccactcctgc ccccgagtgt aactcctgag cttccgggtc    4920
acacgcctat ccactgtcag cactgagaag actgttccct ccggtttgtc tgtccttgtc    4980
ccattagagc catggatggc ccctcagaac ttctgctttc tcactgatgg gacactctgg    5040
atattgtgca ggaattgatg tgttacgcag cacaaaatcc atgctaaata atcatttatg    5100
gttgcccctc ttctgcaggc cttccctcgt gggcccagag tccagagat ggctgtagtg    5160 ggcttaaaca gtgtcatgcc ctgtgtcacc ttggcatcag ttgcaaaaga cagctatgtc    5220
ctgaaggtct cttggtcaga gaagggcttc tgccttggga gggcactctg tcagggtgt    5280 gtagctggcc cgtcccgagt ctgactgttc taagctgaac tatgcaagca gctgatgaag    5340
ctgcttctgc aaagtgaact aggtttttac ctccctgtct ctctttcaat ggagaaagga    5400
cacaatggaa tgtctgtcca gtgaagcctc atccttacaa tgtcataacc aggttgggag    5460
gcgaggacac atgatcctat ctctgccttc agcagaaaaa gtcttccccc acaggtccag    5520
tcagccctgg gaccttctcc aaacagaagc acacagggct gcttccagaa aggagctatc    5580
ccaggttgca caggctggag gaacggcatt tcccatctcc atcccatcct atgaacaggc    5640
taaggaagat gggatctcac tcctggtttt gccttattag tctagatcca aactctagat    5700
tgccttaggg tgaacaccgg attcaggcaa ggcaccctt ccagaaggac cccagtccga    5760
agatgggact gccccctcag cttctgctga ggtggagaga cagcacgtac tggctgggtg    5820
taaagtcagc gattggcagg ggtggaggga gggaggagac aagccctccc ctgctggctc    5880
ccctcccctg gactcccccc tccctttcca agtgggatat aagccccgca gggaagctct    5940
gagcagaggc cacggagttc agtagctgtc gagccttcga gcttctccca ccttccatct    6000
```

```
cctcctgctc atcttgcttc ggaagctgta gctgctgtga gtgactggga tcaggaatag   6060
tctggtatca tgatattttg tggggaaact gaggtcgggt ctctggaaac tgggactgag   6120
tggttgcgag ctgggtgggc agggtttagc tgaggtgaga tggagaagcc ggtggggcac   6180 tcggtgtca tcgcagcttt cttccctcat ctacctcttt gcgtattagc gggagtgggg    6240
aggcaagcag gacttacagc tgtctgacag atggggaaac tgaggctaga gatggtgcaa   6300
ggcggtagaa gactaggtga atcctgtggt tgggacaaac agattattga gacgtgggcc   6360
cgacgcctcc cgccttggag gatccaggtt cagaatgacc cacccaccaa agctttcctc   6420
ctagatggtg gcggtgcgca ggccttggcc cgtcacggtc gcaatgctgc taatcctgct   6480
cgcctgtctg ggagccctgg tggacgccta ccctgccaaa ccagaggctc ccggcgaaga   6540
cgcctccccg gaggagctga ccgctacta cgcctccctg cgccactacc tcaacctggt   6600
cacccggcag cggtgagcgc tggagagggc aggcgggtgg acccagcca ccggggttgc    6660 ttcctctccc cagatccacc tggaggcctg accacgcccc ctttgtggtc ccgccccag    6720 gtatggaaaa agagatgtcc ccgcagctct gttctccaaa ctgctcttca cagacgacag   6780
cgacagcgag aacctcccct tcaggtctcg gtagaaaaca cccctcccca ctcatgccct   6840
ggagtgtggc ctgcccccat cacttacaac cctgccttcc tattcaattc atttccttt    6900 cctcctgcag gccagaaggt ttggaccagt ggtgaagact cccccaaggc ctcctgcgag   6960
atgtgttaac tacaccgact tcacttgcat gtttggttta agaagagggc acttcatatc   7020
tcggtgtctc ggacacccag actggagggc tgtgtgtgtt catttccctg tccctaaata   7080
aaaagcaaat ttcgcacaaa atacccgtgt gttttttcca tcctgaagcg tcagtgtgta   7140
aggtgacttg agccccagga aagacaggtg gctaagaaaa tgactctgag gacaaggaga   7200
gggcatggtg gggaagttta acatagaaac ctcatctcag ccaggggctc ccaaaggacc   7260
tgggaaggca ctctggggg aagggagcct aggagagtgg gtgcagtgga ttctgaacgg    7320
gaggaggcaa aagggtgtgg atggagagga gtttaaggtc caggagagca tctgggggaa   7380
ggctagacac cactccctgg ggagttgccc tgagcagccg tggagaactg gaagatggca   7440
tctaggatga gaccctgaag gaagagacct tggagaggcg atatggaatg ggtgcagaag   7500
tcacttccct cgcaccttga gcaggagaag cagcaggagt gtagaggtct ccattctttc   7560
agcaacagtg ggaattccct gtaatgctga atgcaggctg gatagctatg actaactgtg   7620
cctttctggt ggaaaggcat gggggcaccc accaattcct cgctgtcccc attaaacacc   7680
gaggtctaaa gtgttgtggg tgtttaaact gtaggctaac ccgagtccct ggatatctct   7740
tattgcagga agcccattaa ttagaatttc ctgccctctc aggccaccca gtgctctctc   7800
ttgctacttc cctgctcact atgaaatgtg tccatcattc tgtgtcttgt tttcctaggt   7860
cttgaggggg gtggtgctgg aggaggggca tatgttcccc atcctttgtt gagcagcacc   7920
tgcccaggag gaaggctagg ggatggggga ggaggtacca tgttgaagcc aagaatacag   7980
atccacagaa atggtgtcat ccaggaagac tgggtgctat cactgtgtgg atgggagaga   8040
catgcagggc tccttgcagc ctgctggccc tggaaggaga gtggcctctg gtataacact   8100
ttctgtaggg ggaacaatga gacccccaca tctaccttct ggggttgctt ttccccttca   8160
cagggaaagg atgaagaagc aatcctgggg cccaacatat gtcatagact gcatgggttc   8220
tgggctccac agtgtttgct tgcattgctt tctttctctc ctgcctggaa agaccctctt   8280
gtattatggt catcttctag aagccgttcc tggttcccct ttggtggcgt tagtctctct   8340
gttgtctttc cttgcagcat tcccgttact caagattccc cttctggtc ccctgttcct    8400
```

```
ctactgctcc aagcttgcag tgactgcttg tatggttgag tagtaaggac tgtgtgtctg    8460
gatgttggta tctgtggtcc tctgtcttct ggtctgtctg gggaagttgg ggccagtttg    8520
aagctaatgc aggagagacc tggagagaca tattctcgac cacagtcagt ttgtataaag    8580
tgtcctgtct agttaactct tagtgaggtg acctcatttc tggtttactc tggggcattt    8640
tgagcaggag tgtgatccgg agctgatcag cttactcaat acaggggtca ggaagaaact    8700
tagatatgat aatagttaac aaagatagta acaatgatta actttgcaaa aagttctcct    8760
taaaattgat attgattttt attgtataag atgtatgtgc cacagcctat ggagtgaaga    8820
ggacaacttt gggtagtcaa cccaaagttc aatctttaca tgggtcctga gggatcatat    8880
tcaagtcacc aagcctgcgt tgtcagtcag caagcctcag atatcagttt tgttttgaga    8940
cagagctcta tgtagctcta ctgtcctgga gctcactggg tagagcaggc tggcctcgaa    9000
tcagcagaga tccaccttcc tctgccttct gagtactgga attaaagatg tgtaccaccg    9060
tgcctggttc aaacagctct tctttatgtg ttagaccatt agctaattat ttcacataca    9120
gcatagtact atgatattga tttggttctg tgtgtgtgtg cacatgtata acatggtact    9180
catgtggcgg tcaaaggaca acttttttgaa gttggttctt tccttctgct gtgggttttg    9240
gggattgaac tcaggtcctg ctgaatgcct tgccagccca aagcgatacc tatgagggat    9300
cttttgagga aggatctgaa gtacagtcct aggagaagga tggctatacc tgcctcctcc    9360
ctattttagt gacctcatct ttacaaaagt agtaaataaa aggctggctg agccttcttt    9420
gcctttgagc tctttgaaga acccccccctt cctcatcccc tcctgatgtc cctgagacat    9480
atgtacaagt tgggcacaat gacacatttg ggaggctgag gcaagaggat cacaactttc    9540
aagactatcc tggttacat agtgatatgc acctcaaaaa ttacaaagca gagcaccgaa    9600
gagatggctc agcggttaaa agcactgact gttcttccag aggtcctaag ttcaattccc    9660
agcaaccaca tggtggctcc caaccatctg taaagggatc cgatgcgatg cgctcttttg    9720
tttttttttc ttcgagacag ggtttctctg tatagccctg gctgtcctgg aactcactct    9780
gtagaccagg ctggcctcga actcagaaat ccacctgcct ctgcctcccc agtgctggga    9840
ttagaggcgt gagccactac gtccagcttc cgacgccctc ttctggtgtg tctgaaaaga    9900
accacagtgt gctcatatgc ataaaataaa taaataaata ttaaaaaaaa ttataaagca    9960
gaggcctgga gagataattc agttggtaaa gtacttccca ccagcgtaag gaccccgaat   10020
ccacagcact catggaggaa ggcagtccta gtggtacata agtatgattc cagcataaga   10080
gcagtgagac aggtg                                                   10095
```

<210> SEQ ID NO 4
<211> LENGTH: 1069
<212> TYPE: DNA
<213> ORGANISM: homo sapiens
<220> FEATURE:
<221> NAME/KEY: CDS
<222> LOCATION: (542)..(835)

<400> SEQUENCE: 4

```
gcccctggag gaactgaacc cactatcggt catggggccg agactaaatg tggcgggttg      60
tctttaatct gctgccaaga ggaaactcat tcaggcaagt tcagcccttt atgaggaatt     120
cccctgtggt cacattccaa ttcctggacc tgctgccacc ctcagaactg catgctcctt     180
cttcagactt tctaagaatg actcaggtca ttggtggagt gaagtcaaga tttccaactc     240
agtcacctga agagatggag ataccattca tggagctgga ggtccctgga gatttgggaa     300
```

```
ttcagataac aagctaagat aaggagtttg cctacctctg tcctagagcg aagcctgagc    360
cttgggcgcg cagcacacca caagtatctg ttactgtgtt ttgcagaagc ttcaggcggg    420
gatataaacc ccacaaggaa agcgctgagc agaggaggcc tcagcttgac ctgcggcagt    480
gcagcccttg ggacttccct cgccttccac ctcctgctcg tctgcttcac aagctatcgc    540 t atg gtg ttc gtg cgc agg ccg tgg ccc gcc ttg acc aca gtg ctt ctg    589
  Met Val Phe Val Arg Arg Pro Trp Pro Ala Leu Thr Thr Val Leu Leu
  1               5                  10                 15 gcc ctg ctc gtc tgc cta ggg gcg ctg gtc gac gcc tac ccc atc aaa      637
Ala Leu Leu Val Cys Leu Gly Ala Leu Val Asp Ala Tyr Pro Ile Lys
            20                  25                  30 ccc gag gct ccc ggc gaa gac gcc tcg ccg gag gag ctg aac cgc tac      685
Pro Glu Ala Pro Gly Glu Asp Ala Ser Pro Glu Glu Leu Asn Arg Tyr
 35                  40                  45 tac gcc tcc ctg cgc cac tac ctc aac ctg gtc acc cgg cag cgg tat      733
Tyr Ala Ser Leu Arg His Tyr Leu Asn Leu Val Thr Arg Gln Arg Tyr
 50                  55                  60 ggg aaa aga gac ggc ccg gac agg ctt ctt tcc aaa acg ttc ttc ccc      781
Gly Lys Arg Asp Gly Pro Asp Arg Leu Leu Ser Lys Thr Phe Phe Pro
65                  70                  75                  80 gac ggc gag gac cgc ccc gtc agg tcg cgg tcg gag ggc cca gac ctg      829
Asp Gly Glu Asp Arg Pro Val Arg Ser Arg Ser Glu Gly Pro Asp Leu
                85                  90                  95 tgg tga ggaccctga ggcctcctgg gagatctgcc aaccacgccc acgtcatttg        885
Trp catacgcact cccgacccca gaaacccgga ttctgcctcc cgacggcggc gtctgggcag    945
ggttcgggtg cggccctccg cccgcgtctc ggtgcccccg cccctgggc tggagggctg   1005 tgtgtggtcc ttccctggtc ccaaaataaa gagcaaattc cacagaaaaa aaaaaaaaa   1065 aaaa                                                                1069

<210> SEQ ID NO 5
<211> LENGTH: 97
<212> TYPE: PRT
<213> ORGANISM: homo sapiens

<400> SEQUENCE: 5

Met Val Phe Val Arg Arg Pro Trp Pro Ala Leu Thr Thr Val Leu Leu
1               5                   10                  15

Ala Leu Leu Val Cys Leu Gly Ala Leu Val Asp Ala Tyr Pro Ile Lys
            20                  25                  30

Pro Glu Ala Pro Gly Glu Asp Ala Ser Pro Glu Glu Leu Asn Arg Tyr
 35                  40                  45

Tyr Ala Ser Leu Arg His Tyr Leu Asn Leu Val Thr Arg Gln Arg Tyr
 50                  55                  60

Gly Lys Arg Asp Gly Pro Asp Arg Leu Leu Ser Lys Thr Phe Phe Pro
65                  70                  75                  80

Asp Gly Glu Asp Arg Pro Val Arg Ser Arg Ser Glu Gly Pro Asp Leu
                85                  90                  95

Trp

<210> SEQ ID NO 6
<211> LENGTH: 288
<212> TYPE: DNA
<213> ORGANISM: Pan troglodytes
<220> FEATURE:
<221> NAME/KEY: CDS
<222> LOCATION: (1)..(288)
```

-continued

```
<400> SEQUENCE: 6 atg tcg cct tcc cag atg gtg ttc gtg cgc agg ccg tgg ccc gcc ttg      48
Met Ser Pro Ser Gln Met Val Phe Val Arg Arg Pro Trp Pro Ala Leu
1               5                   10                  15 acc aca gtg ctt ctg gcc ctg ctc gtc tgc ctg ggg gcg ctg gtc gac      96
Thr Thr Val Leu Leu Ala Leu Leu Val Cys Leu Gly Ala Leu Val Asp
            20                  25                  30 gcc tat ccc atc aaa ccc gag gct ccc ggc gaa gac gcc tcc ccg gag     144
Ala Tyr Pro Ile Lys Pro Glu Ala Pro Gly Glu Asp Ala Ser Pro Glu
        35                  40                  45 gag ctg aac cgc tac tac gcc tcc ctg cgc cac tac ctc aac ctg gtc     192
Glu Leu Asn Arg Tyr Tyr Ala Ser Leu Arg His Tyr Leu Asn Leu Val
50                  55                  60 acc cgg cag cgg tat ggg aaa aga gac cgc ccg gac ccg cta ctt tcg     240
Thr Arg Gln Arg Tyr Gly Lys Arg Asp Arg Pro Asp Pro Leu Leu Ser
65                  70                  75                  80 aaa tcg ttc ttc ccc gac ggc gag gac cgc cca gtt ggg tcg agg taa     288
Lys Ser Phe Phe Pro Asp Gly Glu Asp Arg Pro Val Gly Ser Arg
                85                  90                  95

<210> SEQ ID NO 7
<211> LENGTH: 95
<212> TYPE: PRT
<213> ORGANISM: Pan troglodytes

<400> SEQUENCE: 7

Met Ser Pro Ser Gln Met Val Phe Val Arg Arg Pro Trp Pro Ala Leu
1               5                   10                  15

Thr Thr Val Leu Leu Ala Leu Leu Val Cys Leu Gly Ala Leu Val Asp
            20                  25                  30

Ala Tyr Pro Ile Lys Pro Glu Ala Pro Gly Glu Asp Ala Ser Pro Glu
        35                  40                  45

Glu Leu Asn Arg Tyr Tyr Ala Ser Leu Arg His Tyr Leu Asn Leu Val
    50                  55                  60

Thr Arg Gln Arg Tyr Gly Lys Arg Asp Arg Pro Asp Pro Leu Leu Ser
65                  70                  75                  80

Lys Ser Phe Phe Pro Asp Gly Glu Asp Arg Pro Val Gly Ser Arg
                85                  90                  95

<210> SEQ ID NO 8
<211> LENGTH: 518
<212> TYPE: DNA
<213> ORGANISM: Rattus norvegicus
<220> FEATURE:
<221> NAME/KEY: CDS
<222> LOCATION: (70)..(360)

<400> SEQUENCE: 8
gtccagccct cgagcttctc ctgccttcca tctcctcctg ctcatctcgc ttcaggagct     60 gtagctgct atg gtg gcg gta cgc agg cct tgg ccc gtt atg gtc gca atg    111
           Met Val Ala Val Arg Arg Pro Trp Pro Val Met Val Ala Met
           1               5                   10 ctg cta gtc ctg ctc gcc tgc ctg gga gcg ctg gtg gac gcc tac ccc     159
Leu Leu Val Leu Leu Ala Cys Leu Gly Ala Leu Val Asp Ala Tyr Pro
15                  20                  25                  30 gct aaa cca gag gct ccg ggc gaa gat gcc tcc ccg gag gag ctg agc     207
Ala Lys Pro Glu Ala Pro Gly Glu Asp Ala Ser Pro Glu Glu Leu Ser
            35                  40                  45 cgc tac tat gct tcc ctg cgc cac tac ctc aac ctg gtc acc cgg cag     255
Arg Tyr Tyr Ala Ser Leu Arg His Tyr Leu Asn Leu Val Thr Arg Gln
        50                  55                  60
```

```
cgg tat ggg aaa aga gaa gtc ccc gca gct ctg ttc tcc aaa ctg ctc     303
Arg Tyr Gly Lys Arg Glu Val Pro Ala Ala Leu Phe Ser Lys Leu Leu
            65                  70                  75 ttc aca gac gac agc gat aat ctc ccc ttc agg tct cgg cca gaa ggt     351
Phe Thr Asp Asp Ser Asp Asn Leu Pro Phe Arg Ser Arg Pro Glu Gly
 80                  85                  90 gtg gac cag tggtgaagac ccccaaggcc tcccgtgaga tgtgctaact              400
Val Asp Gln
 95 acaccgactt cacttgcatg tttggtttaa gaagagggga cttcgtgtct cagacaccca    460 ggctggaggg ctgtgtgtgt tcatgtcccc gtcctcaaat aaaaagcaaa tttcgcac      518
```

<210> SEQ ID NO 9
<211> LENGTH: 97
<212> TYPE: PRT
<213> ORGANISM: Rattus norvegicus

<400> SEQUENCE: 9

```
Met Val Ala Val Arg Pro Trp Pro Val Met Val Ala Met Leu Leu
 1               5                  10                  15

Val Leu Leu Ala Cys Leu Gly Ala Leu Val Asp Ala Tyr Pro Ala Lys
            20                  25                  30

Pro Glu Ala Pro Gly Glu Asp Ala Ser Pro Glu Glu Leu Ser Arg Tyr
        35                  40                  45

Tyr Ala Ser Leu Arg His Tyr Leu Asn Leu Val Thr Arg Gln Arg Tyr
    50                  55                  60

Gly Lys Arg Glu Val Pro Ala Ala Leu Phe Ser Lys Leu Leu Phe Thr
65                  70                  75                  80

Asp Asp Ser Asp Asn Leu Pro Phe Arg Ser Arg Pro Glu Gly Val Asp
                85                  90                  95

Gln
```

<210> SEQ ID NO 10
<211> LENGTH: 36
<212> TYPE: PRT
<213> ORGANISM: Mus musculus

<400> SEQUENCE: 10

```
Tyr Pro Ala Lys Pro Glu Ala Pro Gly Glu Asp Ala Ser Pro Glu Glu
 1               5                  10                  15

Leu Ser Arg Tyr Tyr Ala Ser Leu Arg His Tyr Leu Asn Leu Val Thr
            20                  25                  30

Arg Gln Arg Tyr
        35
```

<210> SEQ ID NO 11
<211> LENGTH: 34
<212> TYPE: PRT
<213> ORGANISM: Mus musculus

<400> SEQUENCE: 11

```
Ala Lys Pro Glu Ala Pro Gly Glu Asp Ala Ser Pro Glu Glu Leu Ser
 1               5                  10                  15

Arg Tyr Tyr Ala Ser Leu Arg His Tyr Leu Asn Leu Val Thr Arg Gln
            20                  25                  30

Arg Tyr
```

<210> SEQ ID NO 12

```
<211> LENGTH: 18
<212> TYPE: DNA
<213> ORGANISM: artificial
<220> FEATURE:
<223> OTHER INFORMATION: synthetic oligonucleotide for amplifying probe
      A

<400> SEQUENCE: 12
agtgatttgc tcagaagc                                                 18

<210> SEQ ID NO 13
<211> LENGTH: 19
<212> TYPE: DNA
<213> ORGANISM: Artificial
<220> FEATURE:
<223> OTHER INFORMATION: synthetic oligonucleotide for amplifying probe
      A

<400> SEQUENCE: 13
ctagttctat agaccagac                                                19

<210> SEQ ID NO 14
<211> LENGTH: 19
<212> TYPE: DNA
<213> ORGANISM: Artificial
<220> FEATURE:
<223> OTHER INFORMATION: synthetic oligonucleotide for amplifying probe
      B

<400> SEQUENCE: 14
ctgccatggc tgaccatgc                                                19

<210> SEQ ID NO 15
<211> LENGTH: 18
<212> TYPE: DNA
<213> ORGANISM: Artificial
<220> FEATURE:
<223> OTHER INFORMATION: synthetic oligonucleotide for amplifying probe
      B

<400> SEQUENCE: 15
tggtggtggc atgcacac                                                 18

<210> SEQ ID NO 16
<211> LENGTH: 18
<212> TYPE: DNA
<213> ORGANISM: Artificial
<220> FEATURE:
<223> OTHER INFORMATION: synthetic oligonucleotide for amplifying Cre-
      EGFP fusion in mouse genomic DNA

<400> SEQUENCE: 16
ggacacgctg aacttgtg                                                 18

<210> SEQ ID NO 17
<211> LENGTH: 20
<212> TYPE: DNA
<213> ORGANISM: Artificial
<220> FEATURE:
<223> OTHER INFORMATION: synthetic oligonucleotide for amplifying Cre-
      EGFP fusion in mouse genomic DNA

<400> SEQUENCE: 17
ctgctcttta ctgaaggctc                                               20

<210> SEQ ID NO 18
<211> LENGTH: 18
<212> TYPE: DNA
```

```
<213> ORGANISM: Artificial
<220> FEATURE:
<223> OTHER INFORMATION: synthetic oligonucleotide for amplifying
      unfused Cre-EGFP in mouse genomic DNA

<400> SEQUENCE: 18
cctggtctgg acacagtg                                                    18

<210> SEQ ID NO 19
<211> LENGTH: 42
<212> TYPE: DNA
<213> ORGANISM: Artificial
<220> FEATURE:
<223> OTHER INFORMATION: synthetic oligonucleotide for detection of
      mouse NPY

<400> SEQUENCE: 19
gagggtcagt ccacacagcc ccattcgctt gttacctagc at                         42

<210> SEQ ID NO 20
<211> LENGTH: 40
<212> TYPE: DNA
<213> ORGANISM: Artificial
<220> FEATURE:
<223> OTHER INFORMATION: synthetic oligonucleotide for detection of
      mouse POMC

<400> SEQUENCE: 20
tggctgctct ccaggcacca gctccacaca tctatggagg                            40

<210> SEQ ID NO 21
<211> LENGTH: 45
<212> TYPE: DNA
<213> ORGANISM: Artificial
<220> FEATURE:
<223> OTHER INFORMATION: synthetic oligonucleotide for detection of
      mouse GHRH

<400> SEQUENCE: 21
gcttgtcctc tgtccacatg ctgtcttcct ggcggctgag cctgg                      45

<210> SEQ ID NO 22
<211> LENGTH: 44
<212> TYPE: DNA
<213> ORGANISM: Artificial
<220> FEATURE:
<223> OTHER INFORMATION: synthetic oligonucleotide for detection of
      mouse Vasopressin

<400> SEQUENCE: 22
tcagagatgg ccctcttgcc gcctcttggg cagttctgga agta                       44

<210> SEQ ID NO 23
<211> LENGTH: 34
<212> TYPE: DNA
<213> ORGANISM: Artificial
<220> FEATURE:
<223> OTHER INFORMATION: lambda phage P1 loxP site

<400> SEQUENCE: 23
ataacttcgt atagcataca ttatacgaag ttat                                  34

<210> SEQ ID NO 24
<211> LENGTH: 1032
<212> TYPE: DNA
<213> ORGANISM: Bacteriophage lambda
<220> FEATURE:
<221> NAME/KEY: CDS
```

<222> LOCATION: (1)..(1032)

<400> SEQUENCE: 24

```
atg tcc aat tta ctg acc gta cac caa aat ttg cct gca tta ccg gtc      48
Met Ser Asn Leu Leu Thr Val His Gln Asn Leu Pro Ala Leu Pro Val
1               5                   10                  15 gat gca acg agt gat gag gtt cgc aag aac ctg atg gac atg ttc agg      96
Asp Ala Thr Ser Asp Glu Val Arg Lys Asn Leu Met Asp Met Phe Arg
            20                  25                  30 gat cgc cag gcg ttt tct gag cat acc tgg aaa atg ctt ctg tcc gtt     144
Asp Arg Gln Ala Phe Ser Glu His Thr Trp Lys Met Leu Leu Ser Val
        35                  40                  45 tgc cgg tcg tgg gcg gca tgg tgc aag ttg aat aac cgg aaa tgg ttt     192
Cys Arg Ser Trp Ala Ala Trp Cys Lys Leu Asn Asn Arg Lys Trp Phe
    50                  55                  60 ccc gca gaa cct gaa gat gtt cgc gat tat ctt cta tat ctt cag gcg     240
Pro Ala Glu Pro Glu Asp Val Arg Asp Tyr Leu Leu Tyr Leu Gln Ala
65                  70                  75                  80 cgc ggt ctg gca gta aaa act atc cag caa cat ttg ggc cag cta aac     288
Arg Gly Leu Ala Val Lys Thr Ile Gln Gln His Leu Gly Gln Leu Asn
                85                  90                  95 atg ctt cat cgt cgg tcc ggg ctg cca cga cca agt gac agc aat gct     336
Met Leu His Arg Arg Ser Gly Leu Pro Arg Pro Ser Asp Ser Asn Ala
            100                 105                 110 gtt tca ctg gtt atg cgg cgg atc cga aaa gaa aac gtt gat gcc ggt     384
Val Ser Leu Val Met Arg Arg Ile Arg Lys Glu Asn Val Asp Ala Gly
        115                 120                 125 gaa cgt gca aaa cag gct cta gcg ttc gaa cgc act gat ttc gac cag     432
Glu Arg Ala Lys Gln Ala Leu Ala Phe Glu Arg Thr Asp Phe Asp Gln
    130                 135                 140 gtt cgt tca ctc atg gaa aat agc gat cgc tgc cag gat ata cgt aat     480
Val Arg Ser Leu Met Glu Asn Ser Asp Arg Cys Gln Asp Ile Arg Asn
145                 150                 155                 160 ctg gca ttt ctg ggg att gct tat aac acc ctg tta cgt ata gcc gaa     528
Leu Ala Phe Leu Gly Ile Ala Tyr Asn Thr Leu Leu Arg Ile Ala Glu
                165                 170                 175 att gcc agg atc agg gtt aaa gat atc tca cgt act gac ggt ggg aga     576
Ile Ala Arg Ile Arg Val Lys Asp Ile Ser Arg Thr Asp Gly Gly Arg
            180                 185                 190 atg tta atc cat att ggc aga acg aaa acg ctg gtt agc acc gca ggt     624
Met Leu Ile His Ile Gly Arg Thr Lys Thr Leu Val Ser Thr Ala Gly
        195                 200                 205 gta gag aag gca ctt agc ctg ggg gta act aaa ctg gtc gag cga tgg     672
Val Glu Lys Ala Leu Ser Leu Gly Val Thr Lys Leu Val Glu Arg Trp
    210                 215                 220 att tcc gtc tct ggt gta gct gat gat ccg aat aac tac ctg ttt tgc     720
Ile Ser Val Ser Gly Val Ala Asp Asp Pro Asn Asn Tyr Leu Phe Cys
225                 230                 235                 240 cgg gtc aga aaa aat ggt gtt gcc gcg cca tct gcc acc agc cag cta     768
Arg Val Arg Lys Asn Gly Val Ala Ala Pro Ser Ala Thr Ser Gln Leu
                245                 250                 255 tca act cgc gcc ctg gaa ggg att ttt gaa gca act cat cga ttg att     816
Ser Thr Arg Ala Leu Glu Gly Ile Phe Glu Ala Thr His Arg Leu Ile
            260                 265                 270 tac ggc gct aag gat gac tct ggt cag aga tac ctg gcc tgg tct gga     864
Tyr Gly Ala Lys Asp Asp Ser Gly Gln Arg Tyr Leu Ala Trp Ser Gly
        275                 280                 285 cac agt gcc cgt gtc gga gcc gcg cga gat atg gcc cgc gct gga gtt     912
His Ser Ala Arg Val Gly Ala Ala Arg Asp Met Ala Arg Ala Gly Val
    290                 295                 300
```

```
tca ata ccg gag atc atg caa gct ggt ggc tgg acc aat gta aat att      960
Ser Ile Pro Glu Ile Met Gln Ala Gly Gly Trp Thr Asn Val Asn Ile
305             310                 315                 320 gtc atg aac tat atc cgt aac ctg gat agt gaa aca ggg gca atg gtg     1008
Val Met Asn Tyr Ile Arg Asn Leu Asp Ser Glu Thr Gly Ala Met Val
                325                 330                 335 cgc ctg ctg gaa gat ggc gat tag                                     1032
Arg Leu Leu Glu Asp Gly Asp
                340
```

<210> SEQ ID NO 25
<211> LENGTH: 343
<212> TYPE: PRT
<213> ORGANISM: Bacteriophage lambda

<400> SEQUENCE: 25

```
Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320
```

```
Val Met Asn Tyr Ile Arg Asn Leu Asp Ser Glu Thr Gly Ala Met Val
            325                 330                 335
Arg Leu Leu Glu Asp Gly Asp
            340

<210> SEQ ID NO 26
<211> LENGTH: 4776
<212> TYPE: DNA
<213> ORGANISM: Mus musculus

<400> SEQUENCE: 26
aatggattaa gtttttagat ttgttacagt cctgttctaa aaggtactta gaaaccatct      60
cgttaaagac tgcccatccc tctctggtgt ctctgttttc actcagtatc tcttactttg     120
ggggaaatcc ctgcccagct ctgcatagac acgttaagca tcagggaccg tctgcagact     180
tatctcatcc tcttaaacgg aagacacgga gataaccaga gcttccaaac ctgccattac     240
cttgggttcc aggaacaacg gagccttgct ggctcattcc cagatgaggg caaccatcca     300
caagggtggg gcttgtaccc tggagaatga gtcaccatct cctgagaacc agcctgtctc     360
ctcaggtgac agggacgtct ttggacatct tgaagaattg aaactgagac tatggtcacc     420
agattatgcc ttgactaaat ctgcttgggt tcaattctgg tcatcagggt tggtggcaag     480
taccttttacc tgctgagcta ttttaccaga tttcctcttc tttccttccc ccacctctgg     540
cctttcatcc tttctagaca gggtctccat cctggctagt tttatgtcat cattatacaa     600
gctagaatca cctgaaagga gggaagctca attgagaaaa tgcctccata agatacatct     660
gtagcccatt ttcttcatta gtgattgaca gaggaggact caacccatct tgggtggtgc     720
tatccctggg ctggtggtcc tgggttttac aataaagcag gagaagttag ccatgaggag     780
caagccagta agcagcatcc ctccatggcc tctgcatcag ctcctgcctc caggttcttg     840
ccctgattca tttcctgtcc tgatgttctt tgagagttaa actgtgatgt ggaagtgtca     900
gccaaataaa gtctgcctcc ccaacttcct ttggttactg tgtttcatca tgccatagtg     960
accataatta agatatcctg ggatagcctc aagctcttaa tatagccaaa aacatacacg    1020
ctaaacttcc gatcttgctt ctacatctgg agtactgggg gttctagatg tgtggtgggg    1080
atccctgcta atgctggggg tcaatctctg agatctgtgc atgctaagta agaactagac    1140
ccgagacaca ccaccacttc ctcttgttat tttgttctga acaaggtgac attacatagc    1200
ccaggctggc ctggaacttg agatccctct agtgctggga ttacaggttg tgcacccacg    1260
tctgtaagga atgactcttt cctgccagtg actttgcttg ggaggagtc attggcaatg    1320
tcctgtctat cagaggtcct gttgtagata ctgggttcgg gtgaccactg gtatgttaca    1380
gaaggctaag tcacttagga taagtggact tgatatgact agacaaggcg agtgattttc    1440
cgaggttcag gtctctaacc tccttgacct gggttggttt ttattatgtc ctctgaggac    1500
gaagagcaat ggaatcccag caattctgtc tctgtatcct tcaaggagag gttggaggct    1560
ggtcctggtc tcaagtgcac agtaacaatt gttttggaag tttgccctca caggtgtcgt    1620
cacccagttt gcagacttgt ctcatggagg ctgagtcacc ggtcgatgat gatggggggc    1680
actcagtggg gccagccaag tctattgatc gaggctgaga catcctcccc actaatcaac    1740
agttaattaa gtcttttgatg aggggggtggt gattaatgac tagaaggcct gtcctgtaat    1800
tggggcatgg agggaatacc aagatgcaca gaggggcttt gtgaggatgg gggaggctgg    1860
ttcctggtcc acactgaggg acaccccctt gggctcagct tgctttcata cactgaatct    1920
aggcatctag gcctttcctt atatcctctg gcttctccac cctttcccct tttcttcttt    1980
```

```
ccttgaacct tgcattccct aagaccaggg ttgagggctg gggaggtagg ggggtaggga    2040
cattcaggca tggcagatcc tctgtgttcc tttttttttt ttaattaggt attttcctcg    2100
tttacatttt caatgctatc ccaaaggtcc cccatacccca ccccccaatc ccctccccccc   2160
cccccccactc tctgtgttcc tcttacaagc tcctttgtct ctgtctgggg ttggtgcacc    2220
tgcaacctcc tcactaccaa atgcccattc ccatctcctg tcccttgtag cctatagtgt    2280
ccttgtctat ctaggctcca gcctctgtga tcacacctgc cctagccagc acccaggtta    2340
tcctctcctg agcgagcacc tgtcatgtca tcccacgaca tttggttttc cctaaagggt    2400
tagaattctt gtacttctgt tatcttctct ccaaacagaa caccggctgg cctctctgta    2460
actgttctgg ggtcttttaa gactgggagt ccccgctggg tggtggtggc tcacaccttt    2520
gatcccagca cttgggaggc agaggcaggc ggatttcctg agttcaaggc cagcctggtc    2580
tacaaagtgg gttccaggac agccagggat atacagagaa accctgtctc aaaaatacca    2640
gaaaaaaaaa aaaagactg ggagtcccca tggatgtggc tctcctgaga tgagggtcct    2700
tggaggacaa agctgtgact tgacctccag atacaggctc cctaaggaga actgtgtctc    2760
tcttttctcc aaggctgggc tacatgtcct ctcatcctga tcttttccac ttccgtgctc    2820
agcaggatgt cccagttctt cttctgttac aggggggccc ctgtgggatc tggctggctg    2880
ataaggatcc atttccggag agtgcaggtg actgaaccca taaaaaaggt gattgaagaa    2940
gccctggatg ctccatcaca ggtgagttct aaaaatagca tccacagcca tctgtcctgg    3000
gaattggaag ggctggccca gaactagggg cctgggcaag atggtctccc tgtttccatg    3060
ggctagaagt ggtggagact ctggcagggc tgggagaagg acccagaaag ggttggactt    3120
cctatggtcc tctcttcttg gttaagcagg tgggtctgat agggctcttc cccatggggc    3180
tggtggtctg gggtccttcc ctctctcagc caatcagagt aggctgacac tgcccactcc    3240
tgcccccgag tgtaactcct gagcttccgg gtcacacgcc tatccactgt cagcactgag    3300
aagactgttc cctccggttt gtctgtcctt gtcccattag agccatggat ggcccctcag    3360
aacttctgct ttctcactga tgggacactc tggatattgt gcaggaattg atgtgttacg    3420
cagcacaaaa tccatgctaa ataatcattt atggttgccc ctcttctgca ggccttccct    3480
cgtgggcccc agagtccaga gatggctgta gtgggcttaa acagtgtcat gccctgtgtc    3540
accttggcat cagttgcaaa agacagctat gtcctgaagg tctcttggtc agagaagggc    3600
ttctgccttg ggagggcact ctgtcagggg tgtgtagctg gcccgtcccg agtctgactg    3660
ttctaagctg aactatgcaa gcagctgatg aagctgcttc tgcaaagtga actaggtttt    3720
tacctccctg tctctctttc aatggagaaa ggacacaatg gaatgtctgt ccagtgaagc    3780
ctcatcctta caatgtcata accaggttgg gaggcgagga cacatgatcc tatctctgcc    3840
ttcagcagaa aaagtcttcc cccacaggtc cagtcagcct gggaccttct ccaaacagaa    3900
gcacacaggg ctgcttccag aaaggagcta tccaggttg cacaggctgg aggaacggca    3960
tttcccatct ccatcccatc ctatgaacag gctaaggaag atgggatctc actcctggtt    4020
ttgccttgtt agtctagatc caaactctag attgccttag ggtgaacacc ggattccaggc   4080
aaggcaccct ttccagaagg accccagtcc gaagatggga ctgcccccctc agcttctgct    4140
gaggtggaga gacagcacgt actggctggg tgtaaagtca gcgattggca ggggtggagg    4200
gagggaggag acaagccctc ccctgctggc tcccctcccc tggactcccc cctcccttttc    4260
caagtgggat ataagcccccg cagggaagct ctgagcagag gccacggagt tcagtagctg    4320
tcgagccttc gagcttctcc caccttccat ctcctcctgc tcatcttgct tcggaagctg    4380
```

-continued

```
tagctgctgt gagtgactgg gatcaggaat agtctggtat catgatattt tgtggggaaa    4440
ctgaggtcgg gtctctggaa actgggactg agtggttgcg agctgggtgg cagggttta    4500 gctgaggtga gatggagaag ccggtggggc actcgggtgt catcgcagct ttcttccctc    4560
atctacctct ttgcgtatta gcgggagtgg ggaggcaagc aggacttaca gctgtctgac    4620
agatggggaa actgaggcta gagatggtgc aaggcggtag aagactaggt gaatcctgtg    4680
gttgggacaa acagattatt gagacgtggg cccgacgcct cccgccttgg aggatccagg    4740
ttcagaatga cccacccacc aaagctttcc tcctag                              4776
```

<210> SEQ ID NO 27
<211> LENGTH: 36
<212> TYPE: PRT
<213> ORGANISM: homo sapiens

<400> SEQUENCE: 27

```
Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35
```

<210> SEQ ID NO 28
<211> LENGTH: 34
<212> TYPE: PRT
<213> ORGANISM: homo sapiens

<400> SEQUENCE: 28

```
Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr
```

<210> SEQ ID NO 29
<211> LENGTH: 9
<212> TYPE: PRT
<213> ORGANISM: artificial
<220> FEATURE:
<223> OTHER INFORMATION: human PYY[1-9] peptide

<400> SEQUENCE: 29

```
Tyr Pro Ile Lys Pro Glu Ala Pro Gly
1               5
```

<210> SEQ ID NO 30
<211> LENGTH: 11
<212> TYPE: PRT
<213> ORGANISM: artificial
<220> FEATURE:
<223> OTHER INFORMATION: human PYY[3-13] peptide

<400> SEQUENCE: 30

```
Ile Lys Pro Glu Ala Pro Gly Glu Asp Ala Ser
1               5                   10
```

<210> SEQ ID NO 31
<211> LENGTH: 24
<212> TYPE: PRT
<213> ORGANISM: artificial
<220> FEATURE:
<223> OTHER INFORMATION: human PYY[13-36] peptide

```
<400> SEQUENCE: 31

Ser Pro Glu Glu Leu Asn Arg Tyr Tyr Ala Ser Leu Arg His Tyr Leu
1               5                   10                  15

Asn Leu Val Thr Arg Gln Arg Tyr
            20
```